US010082460B1

(12) United States Patent
Liu et al.

(10) Patent No.: US 10,082,460 B1
(45) Date of Patent: Sep. 25, 2018

(54) SYSTEM AND METHOD FOR IMAGE SPECIFIC ILLUMINATION OF IMAGE PRINTED ON OPTICAL WAVEGUIDE

(71) Applicant: Xerox Corporation, Norwalk, CT (US)

(72) Inventors: Chu-Heng Liu, Penfield, NY (US); David C. Craig, Pittsford, NY (US)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 15/630,198

(22) Filed: Jun. 22, 2017

(51) Int. Cl.
*F21V 7/04* (2006.01)
*G02B 6/42* (2006.01)
*G01N 21/47* (2006.01)
*G06K 9/20* (2006.01)
*F21V 8/00* (2006.01)

(52) U.S. Cl.
CPC ............ *G01N 21/47* (2013.01); *G02B 6/0043* (2013.01); *G02B 6/0065* (2013.01); *G06K 9/2063* (2013.01); *G02B 6/003* (2013.01); *G02B 6/006* (2013.01)

(58) Field of Classification Search
USPC ............................................. 385/5; 362/310
See application file for complete search history.

(56) References Cited

U.S. PATENT DOCUMENTS

| | | | |
|---|---|---|---|
| 6,288,700 B1 | 9/2001 | Mori | |
| 6,488,397 B1 | 12/2002 | Masutani et al. | |
| 7,507,012 B2 | 3/2009 | Aylward et al. | |
| 7,549,783 B2 | 6/2009 | Cassarly et al. | |
| 7,762,704 B2 | 7/2010 | Brychell | |
| 7,991,257 B1 * | 8/2011 | Coleman | B29D 11/0073 264/1.24 |
| 8,033,706 B1 | 10/2011 | Kelly et al. | |
| 8,282,260 B2 | 10/2012 | Kim et al. | |
| 8,511,884 B2 | 8/2013 | Donahue | |
| 8,657,480 B2 | 2/2014 | Lee et al. | |
| 8,891,918 B2 | 11/2014 | Li | |
| 8,915,640 B2 | 12/2014 | Park et al. | |
| 8,926,155 B2 | 1/2015 | Choi et al. | |
| 8,980,012 B2 | 3/2015 | Fuller | |
| 9,004,737 B2 | 4/2015 | Tsai et al. | |
| 9,086,516 B2 | 7/2015 | Gourlay | |
| 9,110,200 B2 | 8/2015 | Nichol et al. | |
| 9,188,711 B2 | 11/2015 | Hwang et al. | |
| 9,198,258 B2 | 11/2015 | Kim et al. | |
| 9,217,894 B2 | 12/2015 | Chung et al. | |
| 9,310,547 B2 | 4/2016 | Son et al. | |
| 9,377,574 B2 | 6/2016 | Li | |
| 9,632,218 B2 | 4/2017 | Liu et al. | |
| 2010/0142220 A1 | 6/2010 | Lee et al. | |
| 2010/0149788 A1 | 6/2010 | Kim et al. | |
| 2011/0317417 A1 | 12/2011 | Gourlay | |
| 2012/0011754 A1 | 1/2012 | Matyear | |
| 2013/0265754 A1 | 10/2013 | Tsai et al. | |
| 2013/0272022 A1 | 10/2013 | Choi et al. | |
| 2014/0185318 A1 | 7/2014 | Son et al. | |
| 2014/0279251 A1 | 9/2014 | Cheng et al. | |

(Continued)

*Primary Examiner* — Eric Wong
(74) *Attorney, Agent, or Firm* — Michael J. Nickerson; Basch & Nickerson LLP

(57) ABSTRACT

A display device component includes an optical waveguide having a surface; a first material formed on a portion of the surface of the optical waveguide; and a second material formed on a portion of the first material. The first material has light scattering properties.

25 Claims, 39 Drawing Sheets

(56) References Cited

U.S. PATENT DOCUMENTS

| | | |
|---|---|---|
| 2014/0319995 A1 | 10/2014 | Kim et al. |
| 2015/0279251 A1 | 10/2015 | Matyear |
| 2016/0041325 A1 | 2/2016 | Kim et al. |
| 2016/0306090 A1 | 10/2016 | Pu et al. |
| 2018/0086028 A1 | 3/2018 | Berard et al. |

* cited by examiner

SYSTEM AND METHOD FOR IMAGE SPECIFIC ILLUMINATION OF IMAGE PRINTED ON OPTICAL WAVEGUIDE

BACKGROUND

Various transparent materials have been conventionally used as optical waveguides for optical total internal reflection. Examples of such optical waveguides are optical fibers and sheets of acrylic or glass.

However, total internal reflection can be "frustrated" on an image-wise basis by engraving marks in the surface of the optical medium (optical waveguide) so that the internally reflecting light partially externally refracts and escapes the optical waveguide. Engraving marks in the surface of the optical medium enables the production of a variety of optical signs where the image appears to "hover" in space.

FIG. 1 shows a conventional edge lit sign wherein a piece of acrylic 10 is edge lit with a light source (LEDS) 20. The light is internally reflected within the acrylic 10 except where the light encounters engraved regions (11, 12, and 13) that introduce interface angles (as illustrated in FIG. 2), between acrylic 10 and air. The interface angles, formed by the engraving process, "frustrate" internal reflection and allow light to escape the acrylic 10 at these points (11, 12, and 13). The effect of this type of imaging is striking since the light seems to originate in the engraved images (11, 12, and 13).

As illustrated in FIG. 2, light 25 from a light source is totally reflected within the optical waveguide 10 until it encounters an engraved section 11. At the engraved section 11, a portion of the light 25 is frustrated and is refracted out of the optical waveguide as escaped light 27. This refraction at the engraved section 11 causes the light to appear to originate in the engraved image section 11.

However, there are disadvantages to this approach. First, since the color of the light is the color of the illumination source, the images tend to be monochromatic.

This limitation can be overcome, as illustrated in FIG. 3, by using several pieces of acrylic or optical waveguides (10, 16, and 18), each etched with an image (11, 125, and 135) associated with a specific color and illuminated with that a light source (20, 22, and 24) of that color.

This solution is complicated and requires several pieces of etched optical waveguides and several sources of edge illumination.

A second disadvantage is that laser engraving machines draw lines, not rasterized halftone patterns. Thus, laser engraving limits the engravings to line art and cannot provide shading and/or density levels that halftoning can provide.

A third disadvantage of utilizing laser engraving is that once the image is engraved, the optical waveguide cannot be re-used for other images.

Thus, it is desirable to provide a system or process that enables the emanation of an image having multiple distinct colors from a surface of single optical waveguide.

It is further desirable to provide a system or process that that enables the emanation of an image with variable shading or variable light density levels from a surface of single optical waveguide.

It is also desirable to provide a system or process that enables the emanation of an image having multiple distinct colors from a surface of single optical waveguide while maintaining the re-usability of the optical waveguide to emanation other images.

It is additionally desirable to provide a system or process that that enables the emanation of an image with variable shading or variable light density levels from a surface of single optical waveguide while maintaining the re-usability of the optical waveguide to emanation other images.

DETAILED DESCRIPTION OF THE DRAWINGS

Figure 1:
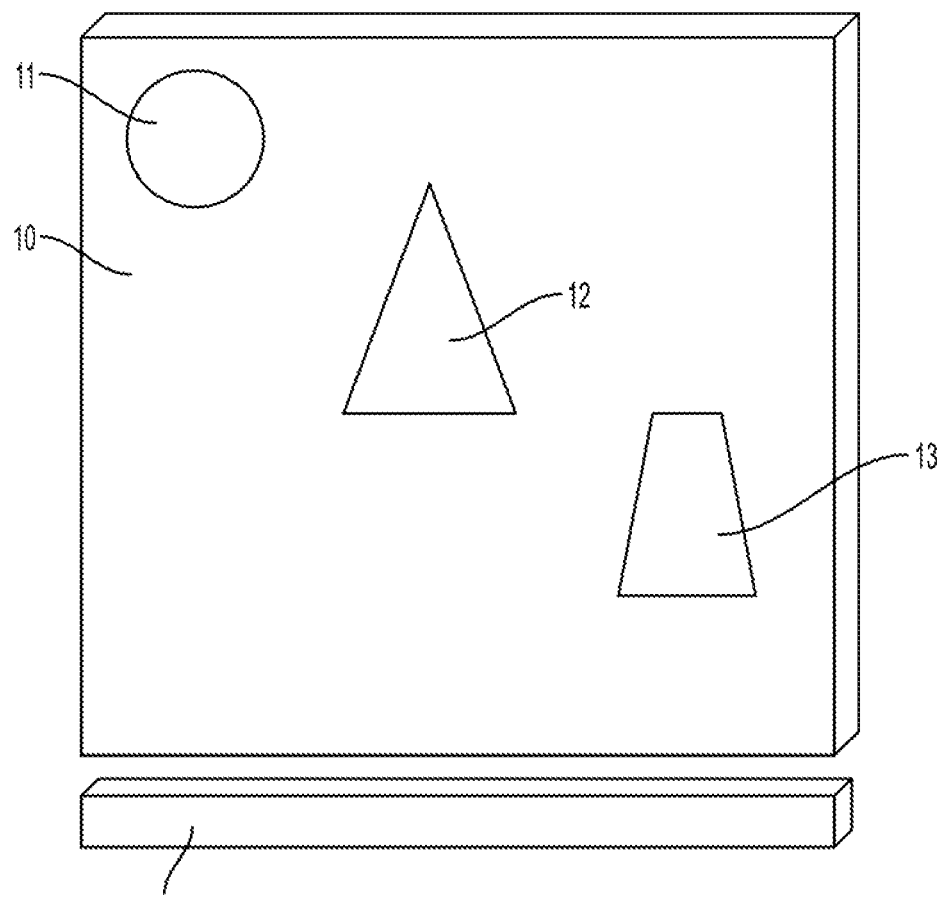
FIG. 1 illustrates a conventional engraved optical waveguide display system.
Figure 2:
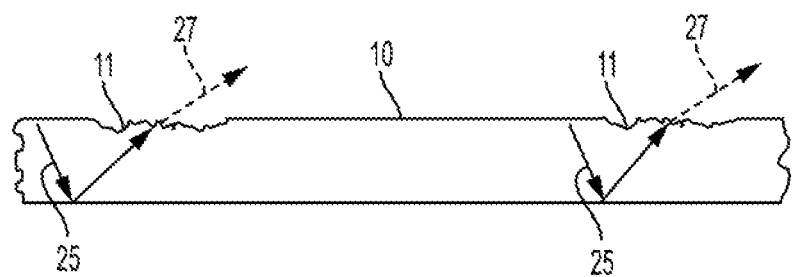
FIG. 2 illustrates an engraved area of the conventional engraved optical waveguide display device of FIG. 1.
Figure 3:
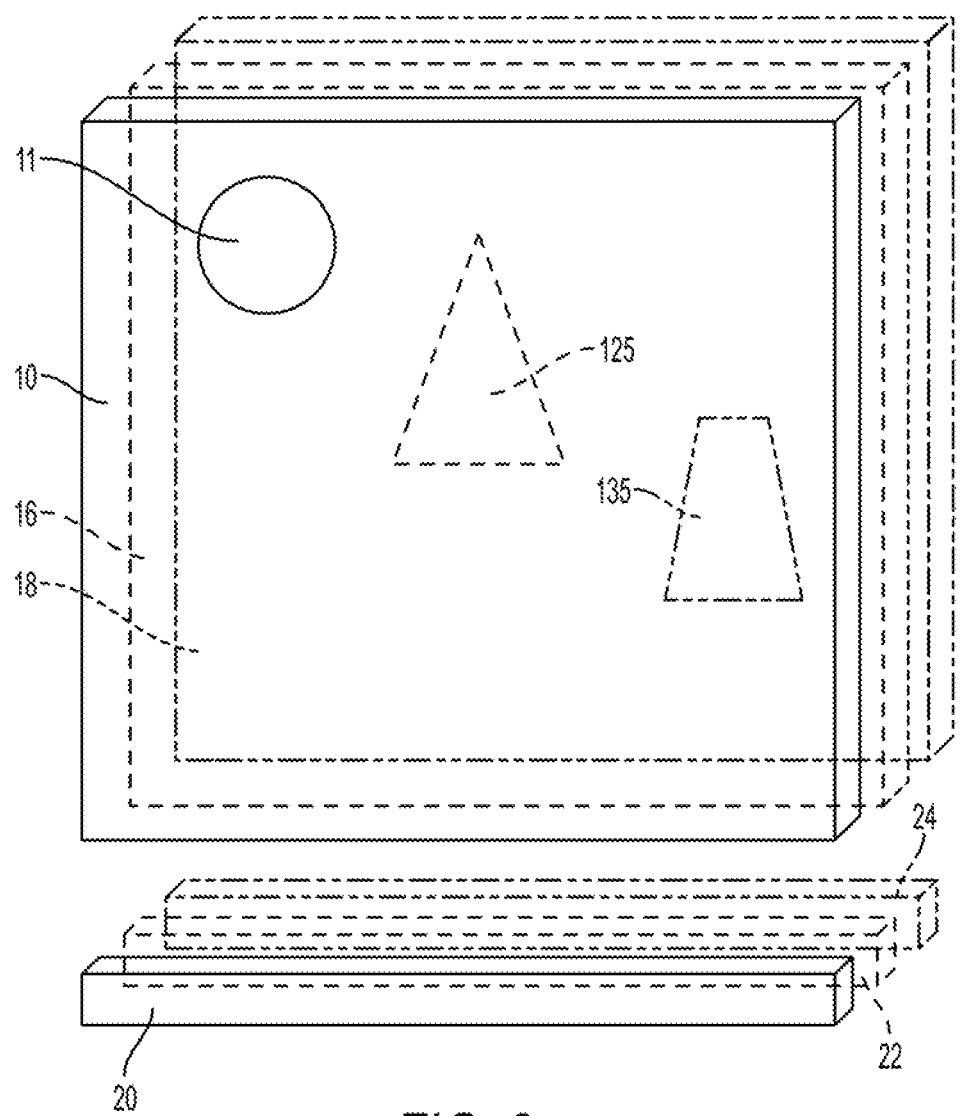
FIG. 3 illustrates a conventional multi-color engraved optical waveguide display system.

For a general understanding, reference is made to the drawings. In the drawings, in some instances, like references have been used throughout to designate identical or equivalent elements. It is also noted that the drawings may not have been drawn to scale and that certain regions may have been purposely drawn disproportionately so that the features and concepts may be properly illustrated.

As noted above, optical waveguides have been utilized to provide a vehicle to display images. The displaying of the images utilizes the principles of Snell's Law.

According to Snell's Law, the critical angle is the angle of incidence for which the angle of refraction is 90°. The angle of incidence is measured with respect to the normal (z-axis) at the refractive boundary, as illustrated in FIG. 4.

Figure 4:
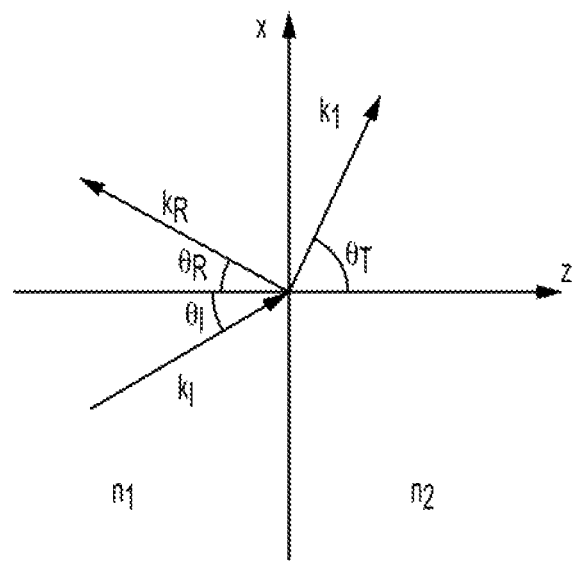
FIG. 4 is a graphical illustration of Snell's law of refraction.

As illustrated in FIG. 4, a light ray passes from glass ($n_1$) into air ($n_2$). The light emanating from the interface (x-axis) is bent (angle $\theta_t$) towards the glass ($n_1$). When the incident angle (angle $\theta_i$) is increased sufficiently, the transmitted angle (in air) reaches 90 degrees. It is at this point no light is transmitted into air. The critical angle $\theta_c$ is given by Snell's law:

$$n_1 \sin \theta_i = n_2 \sin \theta_t$$

To determine the angle of incidence for no refraction, Snell's Law is rearranged as follows:

$$\sin\theta_i = \frac{n_2}{n_1}\sin\theta_t$$

To find the critical angle, solve for the value for $\theta_i$ when $\theta_t = 90°$, and thus, sin $\theta_t = 1$ sin $\theta_t = 1$. The resulting value of $\theta_i$ is equal to the critical angle $\theta_c$.

Solving for $\theta_i$, the equation for the critical angle is as follows:

$$\theta_c = \theta_i = \arcsin\left(\frac{n_2}{n_1}\right) \theta_c = \theta_i = \arcsin\left(\frac{n_2}{n_1}\right)$$

If the incident ray is precisely at the critical angle $\theta_c$, the refracted ray is tangent to the boundary at the point of incidence (x-axis in FIG. 4).

For example, if light was traveling through an optical waveguide; such as acrylic or glass; (with an index of refraction of 1.55) into air (with an index of refraction of 1.00), the calculation would give the critical angle for light from the optical waveguide into air as follows:

$$\theta_c = \arcsin\left(\frac{1.00}{1.55}\right) = 41.8$$

In this example, light incident on the border (x-axis in FIG. 4) with an angle less than 41.8°, with respect to normal (z-axis in FIG. 4), will be partially transmitted, while light incident on the border at larger angles, with respect to normal (z-axis in FIG. 4), would be totally internally reflected.

It is noted that if the fraction $n_2/n_1$ is greater than 1, the arcsine is not defined, meaning that total internal reflection does not occur even at very shallow or grazing incident angles. The critical angle is only defined when $n_2/n_1$ is less than or equal to 1.

Figure 5:
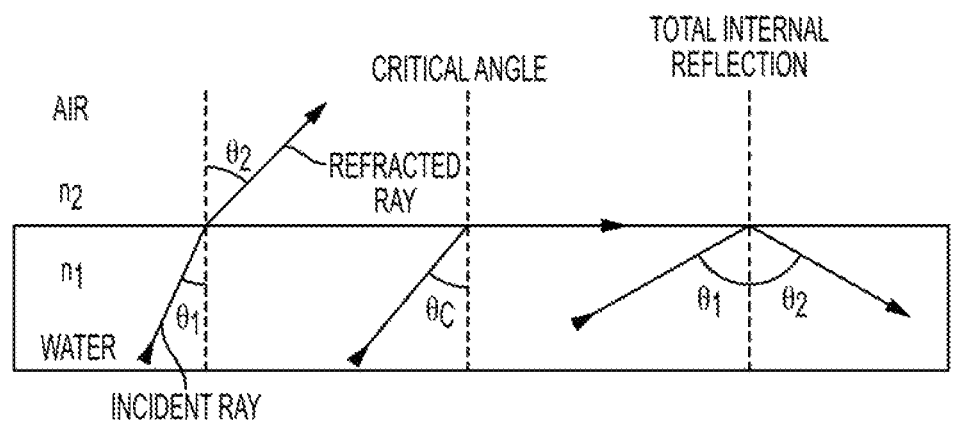
FIG. 5 illustrates refraction of light at the interface between two media.

FIG. 5 shows another example of refraction of light at the interface between two mediums (air and water). As illustrated in FIG. 5, when the incident angle $\theta_1$ of light travelling from water to air is less than the critical angle $\theta_c$, the light is refracted at angle $\theta_2$. On the other hand, as illustrated in FIG. 5, when the incident angle $\theta_1$ of light travelling from water to air is the critical angle $\theta_c$, the light is refracted to travel parallel to the water/air interface. Lastly, as illustrated in FIG. 5, when the incident angle $\theta_1$ of light travelling from water to air greater than the critical angle $\theta_c$, the light is reflected at angle $\theta_2$ to cause a total internal reflection of the incident light.

An alternative to the conventional engraving of an image on a transparent medium (optical waveguide) is to print directly onto the transparent medium (optical waveguide) with marking materials, such as liquid inks, UV curable inks, toners, solid inks, etc., using a printing system.

In the various embodiments described below, an optical waveguide having an index of refraction significantly different from the surrounding medium (such as air) is utilized. For example, an optical waveguide made of acrylic having an index of refraction of about 1.5 may be utilized when the surrounding medium is air, having an index of refraction of about 1.

Moreover, in the various embodiments described below, marking materials having an index of refraction substantially equal to the index of refraction of the optical waveguide is utilized.

For example, a marking material having an index of refraction of about 1.4 may be utilized when the underlying optical waveguide has an index of refraction of about 1.5.

Given the examples discussed above, there are certain angles of light incidence (such as light emanating from a LED source) that cause the incident light to be totally internally reflected at an optical waveguide-air boundary, but partially externally refracted at an optical waveguide-marking material(s) boundary.

These differences in indices of refraction enable the containment of the incident light within the optical waveguide in regions where there is(are) no marking material(s), while releasing light in regions where there is(are) marking material(s).

Upon having the light enter the marking material, to realize illumination of the image, the light or a portion thereof must exit the marking material so as to prevent the light from being totally internally reflected at the marking material-air interface.

More specifically, if the top surface of the marking material is smooth, the angles of incidence at the marking material-air interface are such that the light will internally reflect within the marking material and not exit into the air and towards the viewer.

Figure 6:
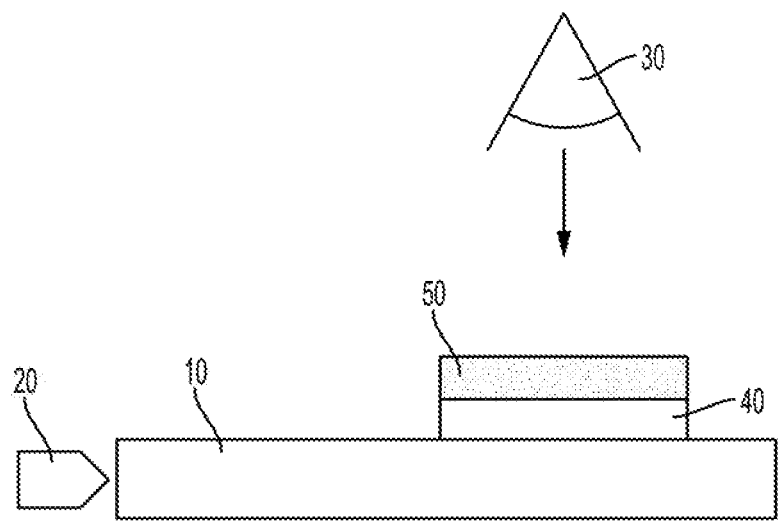
FIG. 6 illustrates an optical waveguide display system utilizing marking materials to display an image.

To enable the refraction of the light at the marking material-air interface to enable the light to exit the marking material, FIG. 6 illustrates an optical waveguide 10, wherein a white marking material 40 is printed on a viewing (30) surface of the optical waveguide 10. Thereafter, another (colored) marking material 50 is printed on top of the white marking material 40.

It is noted that the marking material 40 may be a clear marking material with light scattering properties or light scattering particles embedded therein.

It is further noted that the marking material 40 has light scattering properties or has light scattering particles embedded therein so that the incident light, from a light source 20, is scattered at multiple angles so that at least one of the angles of the scattered light will be incidence upon the marking material-air interface at an angle less than the critical angle so that the light may exit the marking material 50 into the air.

It is noted that the index of refraction of the white marking material 40 is substantially equal to the index of refraction of the optical waveguide 10 so that light will exit the optical waveguide 10 and penetrate the white marking material 40.

The white marking material 40 causes the entering light to scatter in all directions, some of which will exit the white marking material 40, travel in a straight line through the marking material 50 because the index of refraction of the white marking material 40 is substantially equal to the index of refraction of the marking material 50. Based upon the angle of incidence, some of the light entering the marking material 50 will externally refract at the marking material-air interface and travel towards the viewer (30).

Figure 7:
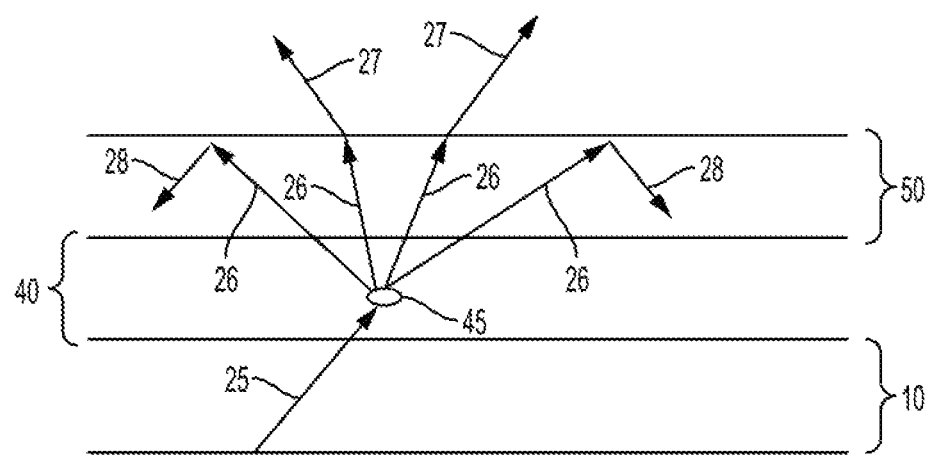
FIG. 7 illustrates the scattering and refracting characteristics of the optical waveguide display system utilizing marking material of FIG. 6.

FIG. 7 is a graphical illustration of the pathway of light in the printed on optical waveguide 10 of FIG. 6. As illustrated in FIG. 7, incidence light 25 is internally reflected within the optical waveguide 10. At the optical waveguide-white marking material interface, since the index of refraction of the white marking material 40 is substantially equal to the index of refraction of the optical waveguide 10, the incidence light 25 will exit the optical waveguide 10 and penetrate the white marking material 40.

Upon encountering an embedded scattering particle 45, the incidence light 25 is scattered at multiple angles to create scattered light 26. At the white marking material-marking material interface, since the index of refraction of the white marking material 40 is substantially equal to the index of refraction of the marking material 50, the scattered light 26 will exit the white marking material 40 and penetrate the marking material 50.

At the marking material-air interface, since the index of refraction of the marking material 50 is substantially different from the index of refraction of air, light 27 (refracted) will exit the marking material 50 into the air when the angle of incidence of the scattered light 26 is less than the critical angle of the marking material-air interface.

Figure 8:
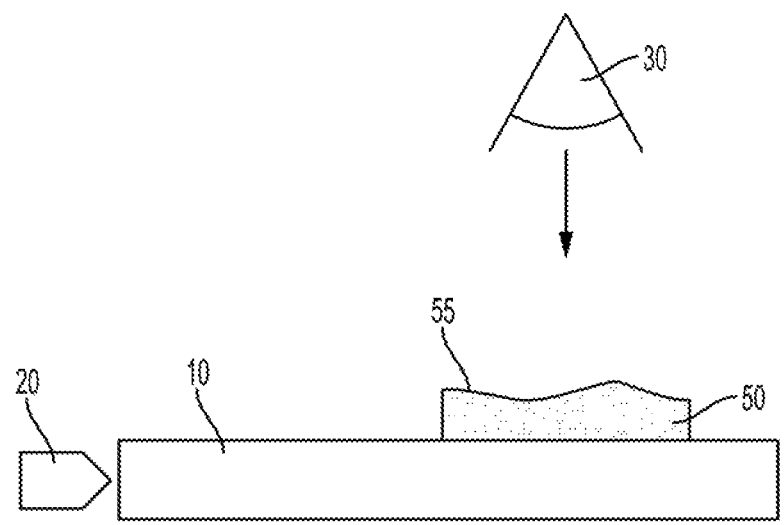
FIG. 8 illustrates an optical waveguide display system utilizing a marking material having a rough surface to display an image.

Moreover, to enable the refraction of the light at the marking material-air interface to enable the light to exit the marking material, FIG. 8 illustrates another example of an optical waveguide 10, wherein a (colored) marking material 50 is printed on a viewing (30) surface of the optical waveguide 10. In this embodiment, a top surface 55 of the marking material 50 is formed so that the top surface 55 is rough, emulating an engraved surface.

It is noted that the index of refraction of the marking material 50 is substantially equal to the index of refraction of the optical waveguide 10 so that light, from a light source 20, will exit the optical waveguide 10 and penetrate the marking material 50.

Thus, based upon the angle of incidence of the light interacting with the rough surface of the marking material-air interface, some of the light entering the marking material 50 will externally refract at the marking material-air interface and travel towards the viewer (30).

Figure 9:
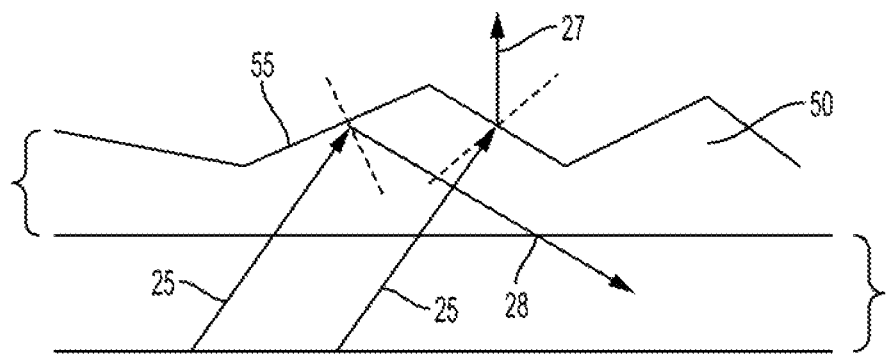
FIG. 9 illustrates the refracting characteristics of the optical waveguide display system utilizing marking material of FIG. 8.

FIG. 9 is a graphical illustration of the pathway of light in the printed on optical waveguide 10 of FIG. 8. As illustrated in FIG. 9, incidence light 25 is internally reflected within the optical waveguide 10.

At the optical waveguide-marking material interface, since the index of refraction of the marking material 50 is substantially equal to the index of refraction of the optical waveguide 10, the incidence light 25 will exit the optical waveguide 10 and penetrate the marking material 50.

At the marking material-air interface, since the index of refraction of the marking material 50 is substantially different from the index of refraction of air, light 27 (refracted) will exit the marking material 50 into the air when the angle of incidence of the light 25 is less than the critical angle of the encountered surface of the marking material-air interface.

Figure 10:
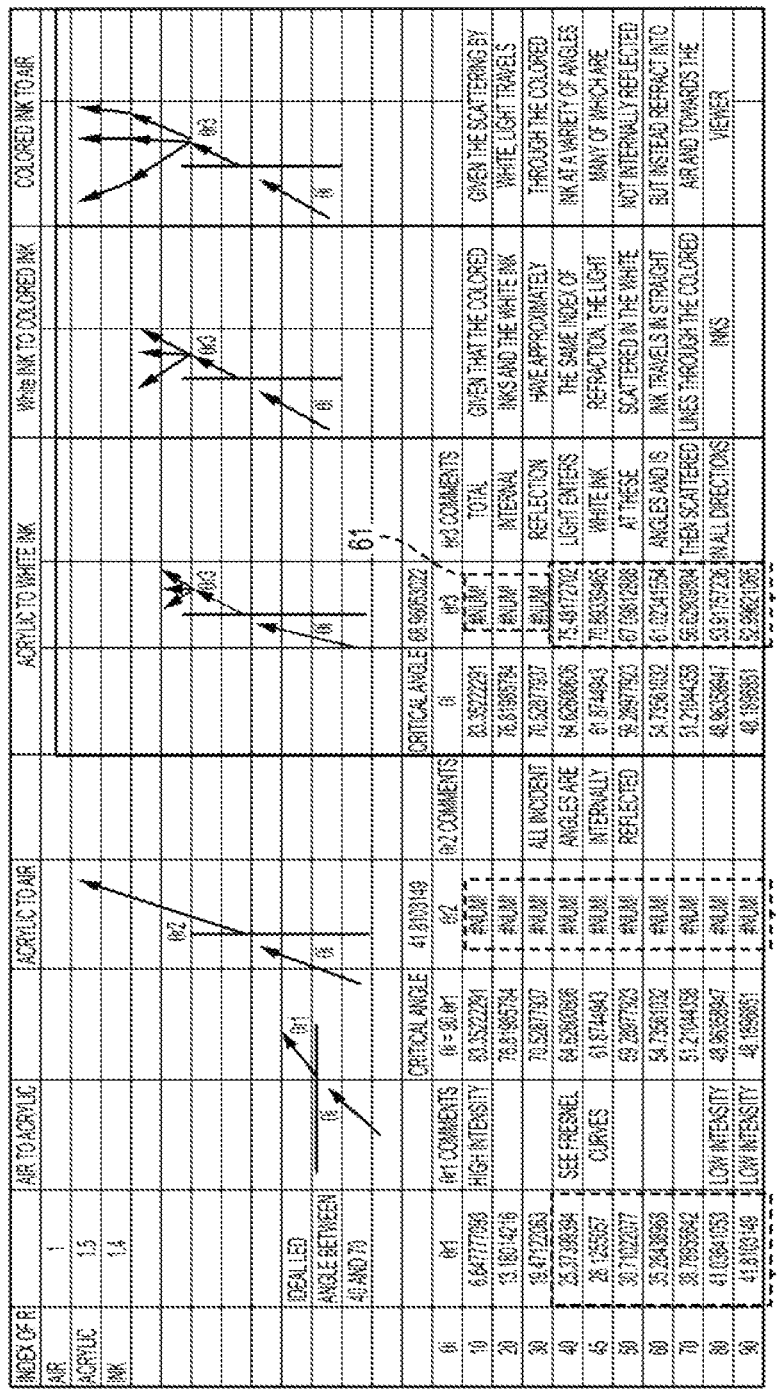
FIG. 10 is a table showing angle values for various optical paths for light travelling through the optical waveguide of FIG. 6.

FIG. 10 is a table providing a summary of the various optical paths through an optical waveguide, as illustrated in FIGS. 6 and 7. More specially, the optical path is defined as light entering the optical waveguide on the left from an illumination source (LED).

The light is then refracted at an air-optical waveguide interface and internally reflected at multiple optical waveguide-air interfaces for all angles. The light is partially externally refracted at the optical waveguide-white marking material interface, for some angles, and scattered by the scattering particles in the white marking material.

The scattered light travels straight through the colored marking material (since the marking materials have similar indices of refraction) and then, since the scattering created many angles of incidence at the colored marking material-air boundary, much of the light exits the colored marking material and travels towards the viewer.

As shown in FIG. 10, on the far left, light enters the optical waveguide (for example, from an LED) with angles of incidence $\theta_i$ ranging from 0 to 90 degrees. The shown refracted angles $\theta_{r1}$ are computed on the basis of Snell's law. The rays of light along the $\theta_{r1}$ paths strike an optical waveguide-air boundary such that for all possible $\theta_{r1}$, the light will be totally internally reflected within the optical waveguide (indicated by #NUM! in dashed boxes 61). The value, #NUM!, indicates that there is no solution for a refracted ray.

After bouncing back and forth within the optical waveguide, the light rays will strike the optical waveguide-white marking material boundary at the same angles as it had struck the optical waveguide-air boundary.

However, since the difference in index of refraction between air (1.0) and the white marking material (for example, 1.4) and depending on the angle of incidence, some of the light is externally refracted into the white marking material instead of being internally reflected within the optical waveguide. The cells within the dashed boxes 62 in FIG. 10 identify the light rays that will be completely internally reflected at the optical waveguide-air interface and partially externally refracted at the optical waveguide-white marking material interface. Thus, light will enter the white marking material.

Since the white marking material scatters light at a variety of angles, these rays of scattered light then travel directly through the colored marking material because the colored marking material and white marking material have similar indices of refraction. Due to the many angles of incidence on the colored marking material-air boundary, many rays will not internally reflect, but will be externally refracted and seen by the viewer.

Figure 11:
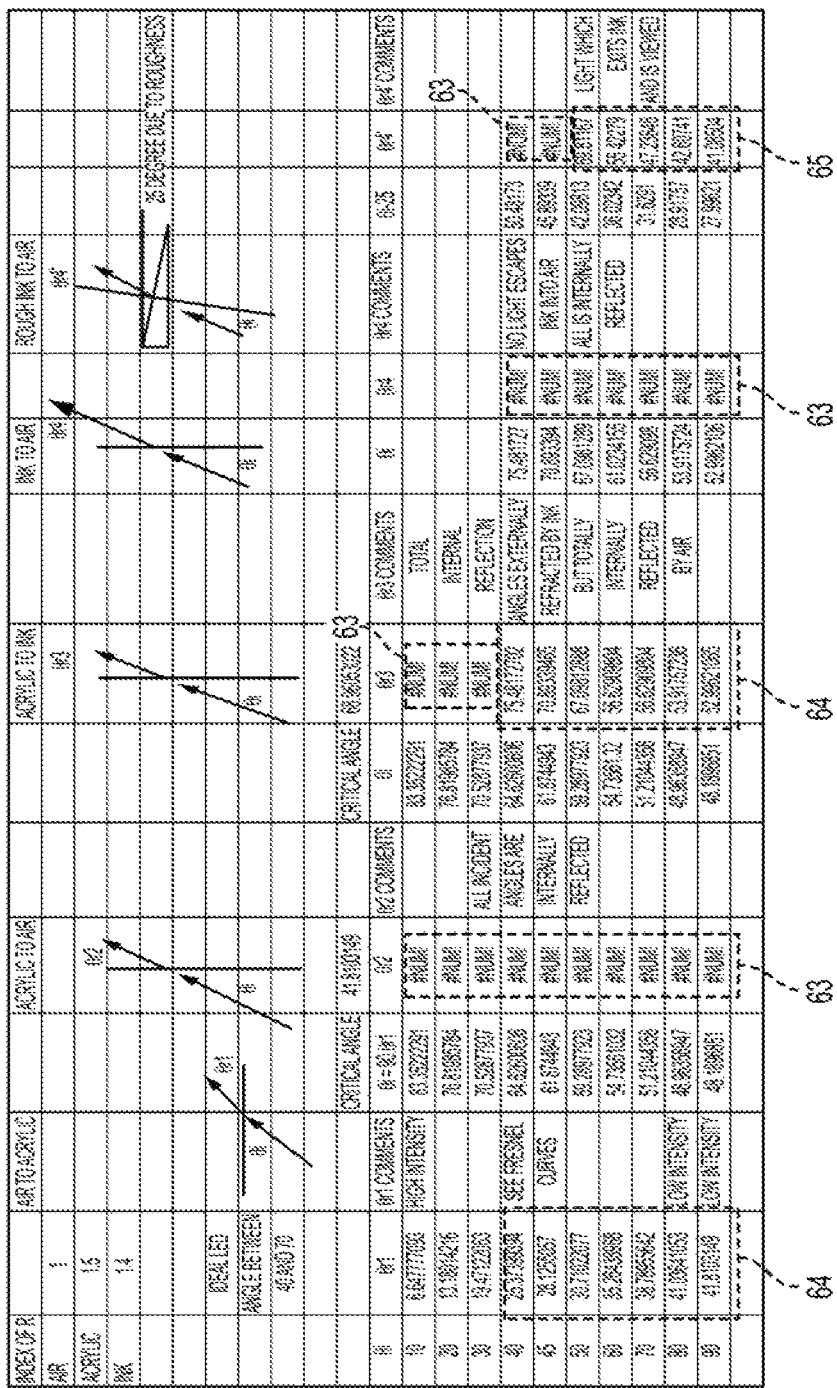
FIG. 11 is a table showing angle values for various optical paths for light travelling through the optical waveguide of FIG. 8.

FIG. 11 is a table providing a summary of the various optical paths through an optical waveguide, as illustrated in FIGS. 8 and 9. More specially, the optical path is defined as light entering the optical waveguide on the left from an illumination source (LED). The light is then refracted at an air-optical waveguide interface and internally reflected at multiple optical waveguide-air interfaces for all angles. The light is partially externally refracted at the optical waveguide-marking material interface for some angles.

The externally refracted light travels through the marking material, and then, since marking material has a rough surface, creating many angles of incidence at the marking material-air boundary, much of the light exits the marking material and travels towards the viewer.

As shown in FIG. 11, on the far left, light enters the optical waveguide (for example, from an LED) with angles of incidence $\theta_i$ ranging from 0 to 90 degrees. The shown refracted angles $\theta_{r1}$ are computed on the basis of Snell's law. The rays of light along the $\theta_{r1}$ paths strike an optical waveguide-air boundary such that for all possible $\theta_{r1}$, the light will be totally internally reflected within the optical waveguide (indicated by #NUM! in dashed boxes 63). The value, #NUM!, indicates that there is no solution for a refracted ray.

After bouncing back and forth within the optical waveguide, the light rays will strike the optical waveguide-marking material boundary at the same angles as it had struck the optical waveguide-air boundary.

However, since the difference in index of refraction between air (1.0) and the marking material (for example, 1.4) and depending on the angle of incidence, some of the light is externally refracted into the marking material instead of being internally reflected within the optical waveguide.

The cells within the dashed boxes 64 in FIG. 11 identify the light rays that will be completely internally reflected at the optical waveguide-air interface and partially externally refracted at the optical waveguide-marking material interface. Thus, light will enter the marking material.

Since the marking material has a rough surface, it produces a variety of angles of incidence. Due to the many angles of incidence on the marking material-air boundary, many rays will not internally reflect, but will be externally refracted and seen by the viewer.

In other words, if the top surface of the marking material is smooth, all of the light entering the marking material will be totally internally reflected at the marking material-air boundary. However, light will escape the marking material is if the angle of interface is modified due to surface roughness.

As illustrated in FIG. 11, the angle of incidence of the light rays (the cells within the dashed box 65) striking the marking material-air boundary quantify the effect of surface roughness.

Thus, the surface roughness causes some of the light to be externally refracted at the marking material-air boundary and exit the marking material towards the viewer.

These cells of dashed box 65 can be traced across the table, starting at a certain angle of incidence from the LED, internally reflected where there is no marking material, refracting into the marking material, and then refracting out of the marking material due to the surface roughness.

It is noted that surface roughness of the printed marking material can be enhanced through halftoning.

Figure 12:
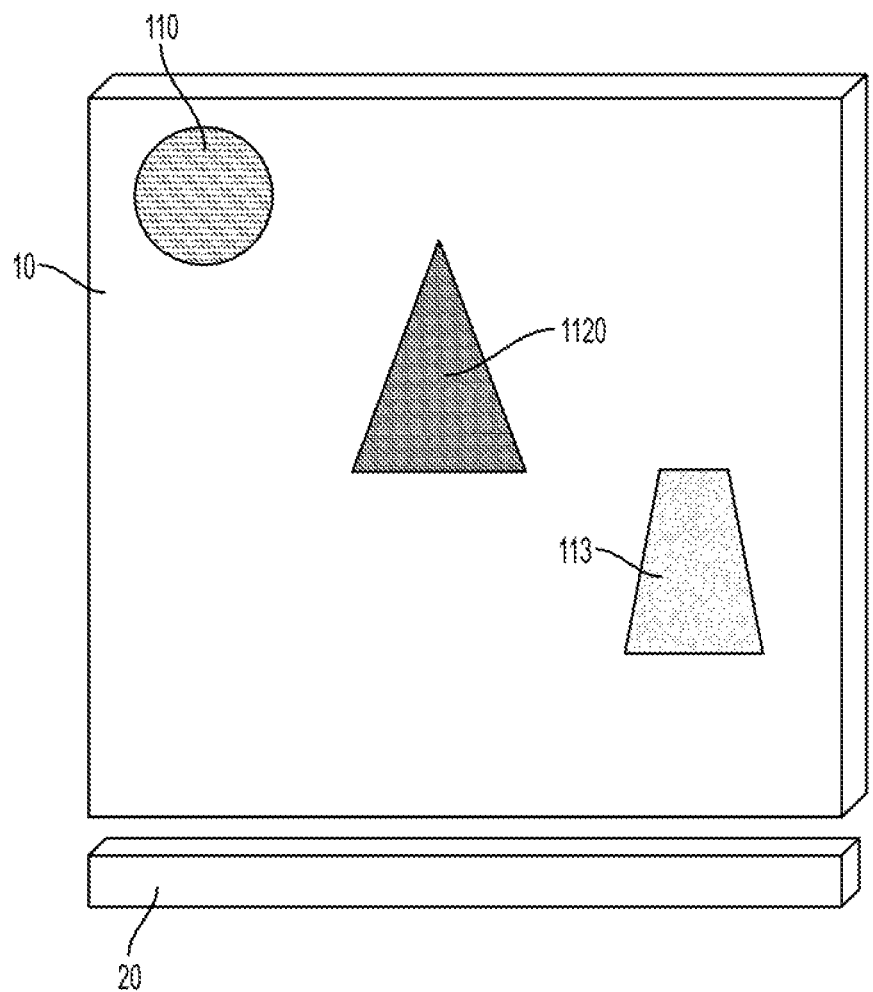
FIG. 12 illustrates an optical waveguide display system displaying an image having multiple distinct colors from a surface of a single optical waveguide.

FIG. 12 illustrates an optical waveguide display system, wherein an optical waveguide 10, when illuminated by a light source 20, displays printed on images 110, 1120, and 113. Since the images 110, 1120, and 113 are printed onto the optical waveguide 10, the images can be different colors and not rely upon the color of the light source 20 to define their color.

Moreover, the images 110, 1120, and 113 may comprise the dual marking material construction of FIGS. 6 and 7 or the marking material with rough surface construction of FIGS. 8 and 9.

Figure 13:
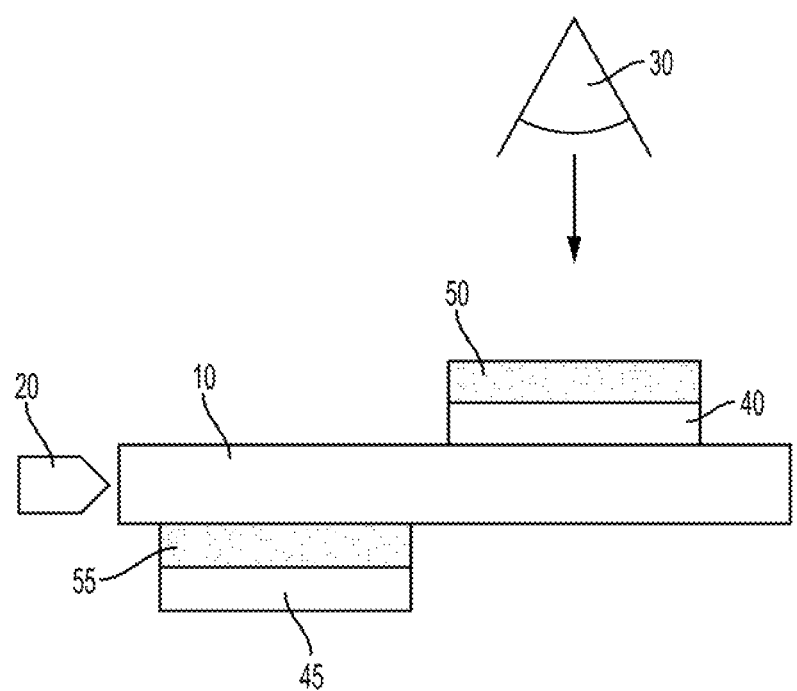
FIG. 13 illustrates an optical waveguide having a front side image and a backside image thereon.

FIG. 13 illustrates an optical waveguide display system, wherein an optical waveguide 10, when illuminated by a light source 20, displays images printed on both sides of the optical waveguide 10. Since the images are printed onto both sides of the optical waveguide 10, the images are constructed differently depending upon the surface side of the optical waveguide 10 with respect to a viewing side 30.

As illustrated in FIG. 13, on a front surface of the optical waveguide 10 (the viewing side 30), the image is constructed in the same manner as illustrated in FIG. 6, wherein a white marking material 40 is printed onto the front surface of the optical waveguide 10, followed by the printing of a marking material 50.

When the image on the front surface of the optical waveguide 10 is illuminated by a light source 20, the printed image (40 and 50) is viewed by the viewer 30.

As further illustrated in FIG. 13, on a back surface of the optical waveguide 10, the image is constructed in a different manner, wherein a marking material 55 is printed onto the back surface of the optical waveguide 10, followed by the printing of a white marking material 45.

When the image on the back surface of the optical waveguide 10 is illuminated by a light source 20, the printed image (45 and 55) is viewed by the viewer 30.

It is noted that the thickness of the optical waveguide 10 can be such to present the images at different depths, thereby making one image to appear to be floating in front of the other image.

Figure 14:
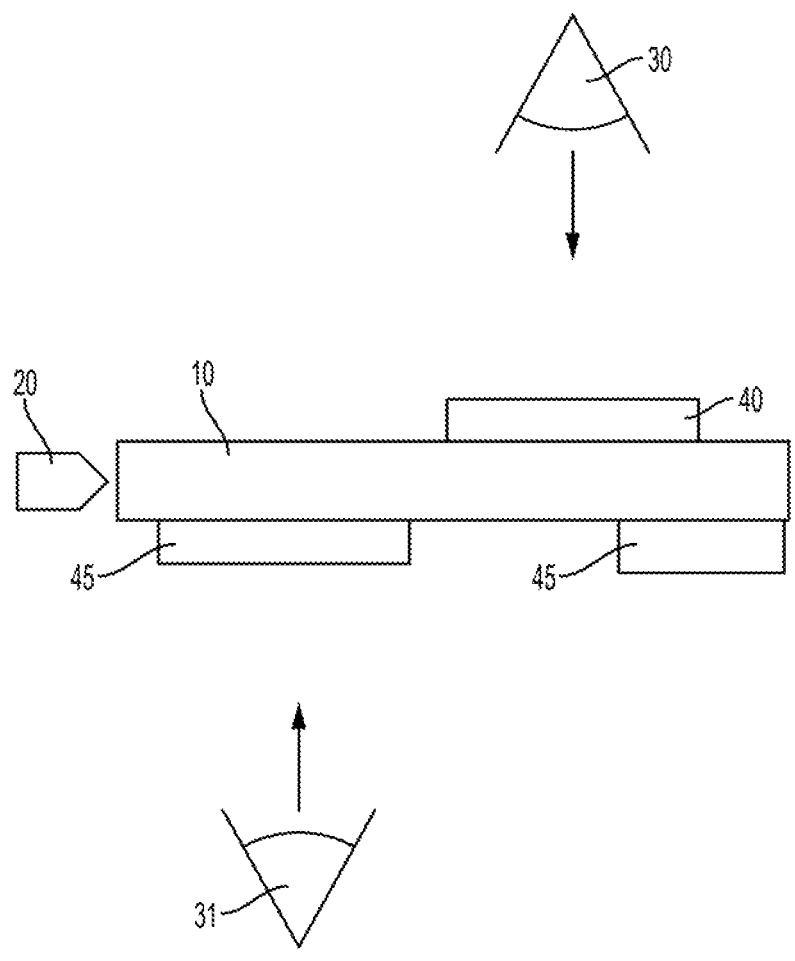
FIG. 14 illustrates another embodiment of an optical waveguide having a front side image and a backside image thereon.

FIG. 14 illustrates an optical waveguide display system, wherein an optical waveguide 10, when illuminated by a light source 20, displays images printed on both sides of the optical waveguide 10 and can be observed from both viewing sides (30 and 31). In this embodiment, the images are printed onto both sides of the optical waveguide 10 using the same construction.

As illustrated in FIG. 14, on a front surface of the optical waveguide 10 (the viewing side 30), the image is constructed of a white marking material 40 that is printed onto the front surface of the optical waveguide 10.

When the image on the front surface of the optical waveguide 10 is illuminated by a light source 20, the printed image (40) on the front surface of the optical waveguide 10 is viewed by the viewer 30 and viewer 31.

As further illustrated in FIG. 14, on a back surface of the optical waveguide 10, the image is also constructed of a white marking material 45 that is printed onto the back surface of the optical waveguide 10.

When the image on the back surface of the optical waveguide 10 is illuminated by a light source 20, the printed image (45) on the back surface of the optical waveguide 10 is viewed by the viewer 30 and viewer 31.

It is noted that the thickness of the optical waveguide 10 can be such to present the images at different depths, thereby making one image to appear to be floating in front of the other image.

Figure 15:
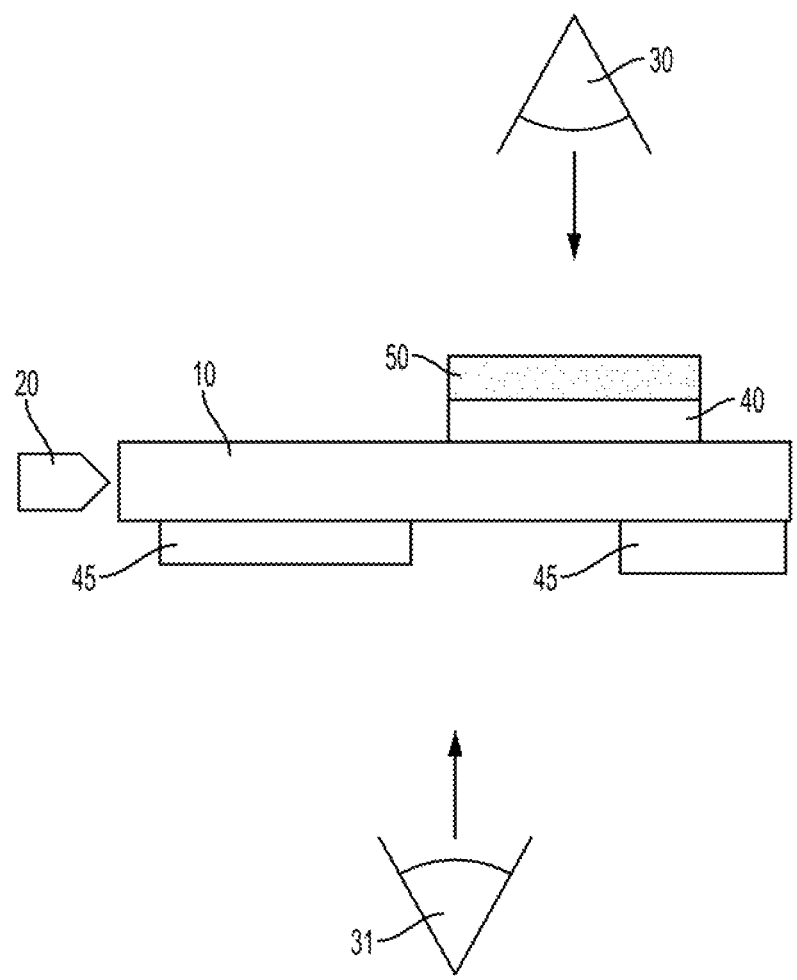
FIG. 15 illustrates an additional embodiment of an optical waveguide having a front side image and a backside image thereon.

FIG. 15 illustrates an optical waveguide display system, wherein an optical waveguide 10, when illuminated by a light source 20, displays images printed on both sides of the optical waveguide 10 and only one viewing side can view both images. In this embodiment, the images are printed onto both sides of the optical waveguide 10 using different constructions.

As illustrated in FIG. 15, on a front surface of the optical waveguide 10 (the viewing side 30), the image is constructed in the same manner as illustrated in FIG. 6, wherein a white marking material 40 is printed onto the front surface of the optical waveguide 10, followed by the printing of a marking material 50.

When the image on the front surface of the optical waveguide 10 is illuminated by a light source 20, the printed image (40 and 50) can only be viewed by the viewer 30.

As further illustrated in FIG. 15, on a back surface of the optical waveguide 10, the image is also constructed of a white marking material 45 that is printed onto the back surface of the optical waveguide 10.

When the image on the back surface of the optical waveguide 10 is illuminated by a light source 20, the printed image (45) on the back surface of the optical waveguide 10 can be viewed by the viewer 30 and viewer 31.

In other words, the embodiment of FIG. 15 enables both images to be viewed by viewer 30, but viewer 31 cannot view the image on the front surface of the optical waveguide 10.

Moreover, as illustrated in FIG. 15, the image printed on the front surface of the optical waveguide 10 can be a color image with a white background and it is only viewable as a color image by viewer 30. On the other hand, the image printed on the back surface of the optical waveguide 10 is a monochrome image, which is viewable by viewer 30 and viewer 31.

It is noted that the thickness of the optical waveguide 10 can be such to present the images at different depths, thereby making one image to appear to be floating in front of the other image.

Figure 16:
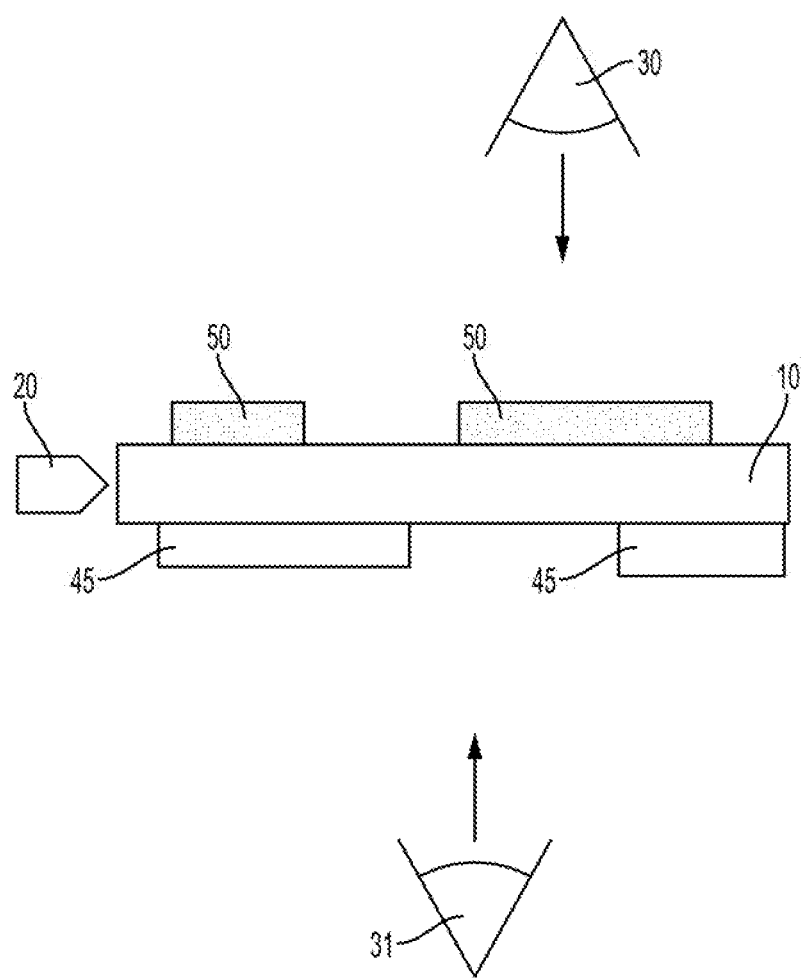
FIG. 16 illustrates a further embodiment of an optical waveguide having a front side image and a backside image thereon.

FIG. 16 illustrates an optical waveguide display system, wherein an optical waveguide 10, when illuminated by a light source 20, displays images printed on both sides of the optical waveguide 10. In this embodiment, the images are printed onto both sides of the optical waveguide 10 using different constructions.

As illustrated in FIG. 16, on a front surface of the optical waveguide 10 (the viewing side 30), the image is constructed, wherein a marking material 50 is printed onto the front surface of the optical waveguide 10.

As further illustrated in FIG. 16, on a back surface of the optical waveguide 10, the image is also constructed of a white marking material 45 that is printed onto the back surface of the optical waveguide 10.

The image on the front surface of the optical waveguide 10 is not viewable alone. The back side image is viewable through the panel by the viewer 30.

As illustrated in FIG. 16, the front image may be a color image without a white background. The color image is typically not viewable alone because there is no scattering. The back side image is a monochrome image created with white marking material 45, which is viewable by viewer 30 and viewer 31.

When the front image and the back image are assembled together, the front side image becomes visible in direction of viewer 30 when the backside image (white marking material 45) provides the scattering light.

When the image on the back surface of the optical waveguide 10 is illuminated by a light source 20, the printed image (45) on the back surface of the optical waveguide 10 can be viewed by the viewer 30 and viewer 31.

It is noted that the backside image should be viewable through the optical waveguide 10. The front side image can be a scattering viewable image or transparent non-viewable image.

The front side image may be sparse, such that there is plenty of transparent viewing area for the back side image.

It is noted that the thickness of the optical waveguide 10 can be such to present the images at different depths, thereby making one image to appear to be floating in front of the other image.

Figure 17:
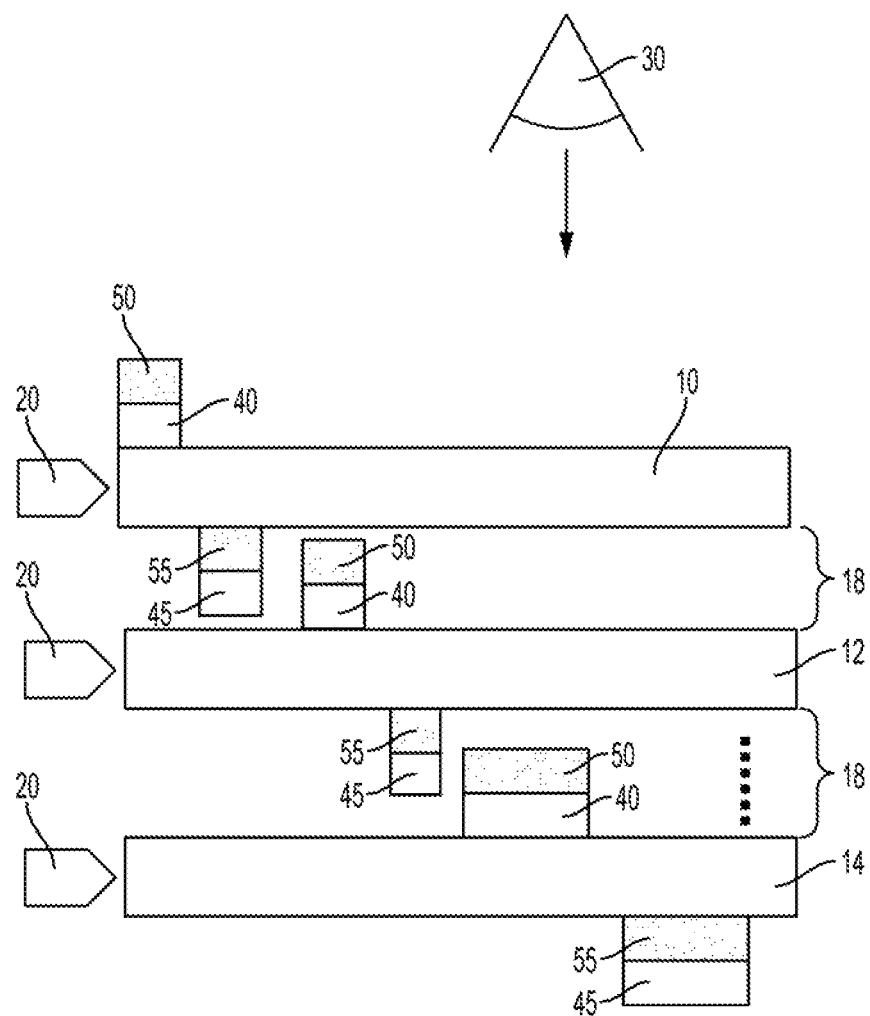
FIG. 17 illustrates an optical waveguide display system displaying a three-dimensional image.

FIG. 17 illustrates a display device for displaying three-dimensional images. As illustrated in FIG. 17, a plurality of optical waveguides (10, 12, and 14). Each optical waveguide has printed thereon images on both sides of the optical waveguide in the same manner as the dual sided images are constructed in the embodiment of FIG. 13.

More specifically, on a front surface of each optical waveguide (the viewing side 30), a white marking material 40 is printed onto the front surface of the optical waveguide, followed by the printing of a marking material 50.

When the image on the front surface of the optical waveguide is illuminated by a light source 20, the printed image (40 and 50) is viewed by the viewer 30.

As further illustrated in FIG. 17, on a back surface of each optical waveguide, a marking material 55 is printed onto the back surface of the optical waveguide, followed by the printing of a white marking material 45.

When the image on the back surface of the optical waveguide is illuminated by a light source 20, the printed image (45 and 55) is viewed by the viewer 30.

Figure 18:
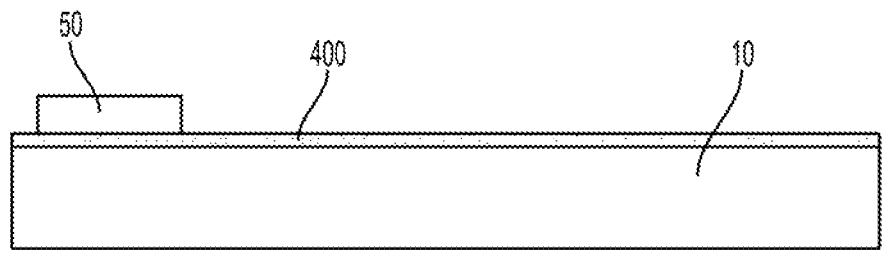
FIG. 18 illustrates an optical waveguide utilizing marking materials to create an image and a white background.

FIG. 18 illustrates an optical waveguide capable of providing a white background for an image printed thereon. As illustrated in FIG. 18, a white marking material 400 is printed over an entire image area. Thereafter, a marking material 50 is printed on the white marking material 400.

It is noted that the white marking material 400 has a varied light scattering particle volumetric density, wherein the light scattering particle volumetric density increases proportionally along the surface of the optical waveguide as a distance away from a light source interface of the optical waveguide increases.

If the light scattering particle volumetric density did not vary proportionally as the distance from the light source interface of the optical waveguide increases most of the light would escape the optical waveguide near the light source interface and there would be enough light to properly illuminate an image in the middle of the optical waveguide.

The light source interface is the interface (surface) of the optical waveguide that receives incident light from a light source.

An image is printed on the white marking material 400 using marking material 50.

Figure 19:
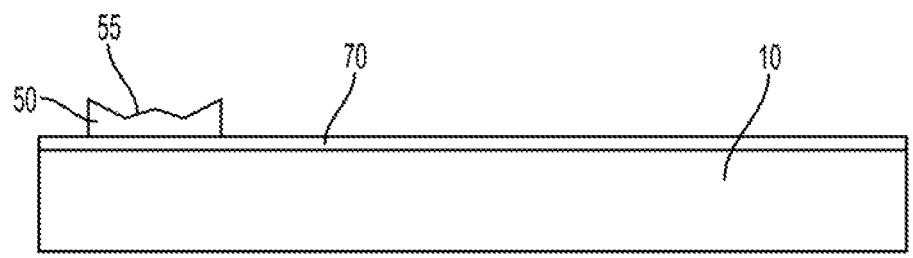
FIG. 19 illustrates an optical waveguide utilizing a marking material having a rough surface pre-printed on a transparent medium.

FIG. 19 illustrates an optical waveguide wherein an image is initially printed on a transparent medium 70, and the transparent medium 70 is attached to the optical waveguide 10. As illustrated in FIG. 19, a marking material 50 with a rough surface 55 is printed on the transparent medium 70.

It is noted that the transparent medium 70 should be attached to the optical waveguide 10 so that there are no air gaps between the transparent medium 70 and the optical waveguide 10.

For example, the transparent medium 70 may be bonded to the optical waveguide using a curable agent that can be rolled to remove the air gaps before curing.

It is noted that the transparent medium 70 may be an optical waveguide having an index of refraction substantially equal to the index of refraction of the optical waveguide 10.

Figure 20:
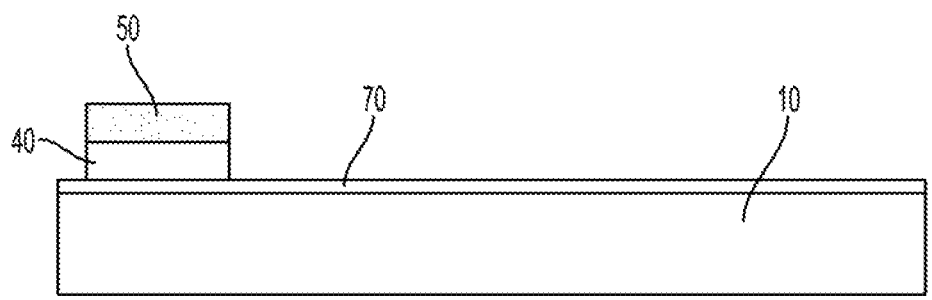
FIG. 20 illustrates an optical waveguide utilizing marking materials pre-printed on a transparent medium.

FIG. 20 illustrates an optical waveguide wherein an image is initially printed on a transparent medium 70, and the transparent medium 70 is attached to the optical waveguide 10. As illustrated in FIG. 20, a white marking material 40 is printed on the transparent medium 70, followed by the printing of a marking material 50.

It is noted that the transparent medium 70 should be attached to the optical waveguide 10 so that there are no air gaps between the transparent medium 70 and the optical waveguide 10.

For example, the transparent medium 70 may be bonded to the optical waveguide using a curable agent that can be rolled to remove the air gaps before curing.

It is noted that the transparent medium 70 may be an optical waveguide having an index of refraction substantially equal to the index of refraction of the optical waveguide 10.

Figure 21:
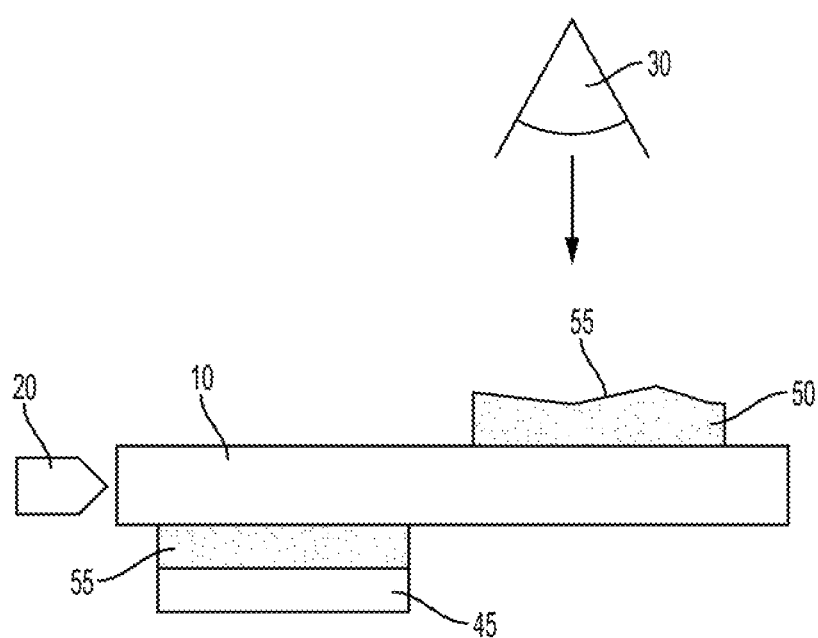
FIG. 21 illustrates an optical waveguide having a front side rough surface image and a backside two layer marking material image thereon.

FIG. 21 illustrates an optical waveguide display system, wherein an optical waveguide 10, when illuminated by a light source 20, displays images printed on both sides of the optical waveguide 10. Since the images are printed onto both sides of the optical waveguide 10, the images are constructed differently depending upon the surface side of the optical waveguide 10 with respect to a viewing side 30.

As illustrated in FIG. 21, on a front surface of the optical waveguide 10 (the viewing side 30), the image is constructed in the same manner as illustrated in FIG. 8, wherein a marking material 50 with a rough surface 55 is printed onto the front surface of the optical waveguide 10.

When the image on the front surface of the optical waveguide 10 is illuminated by a light source 20, the printed image (50 with rough surface 55) is viewed by the viewer 30.

As further illustrated in FIG. 21, on a back surface of the optical waveguide 10, the image is constructed in a different manner, wherein a marking material 55 is printed onto the back surface of the optical waveguide 10, followed by the printing of a white marking material 45.

When the image on the back surface of the optical waveguide 10 is illuminated by a light source 20, the printed image (45 and 55) is viewed by the viewer 30.

It is noted that the thickness of the optical waveguide 10 can be such to present the images at different depths, thereby making one image to appear to be floating in front of the other image.

Figure 22:
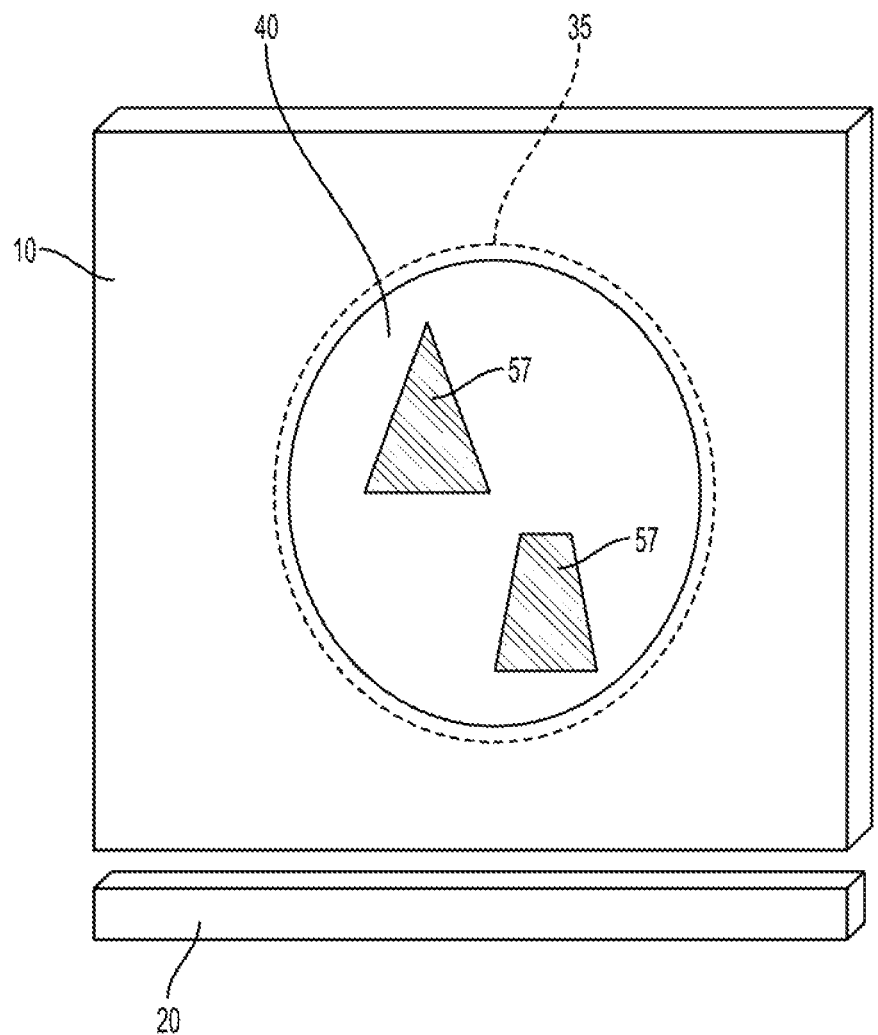
FIG. 22 illustrates an optical waveguide display system displaying an image having white background and a color or black image therein from a surface of a single optical waveguide.

FIG. 22 illustrates an optical waveguide 10 capable of providing a white background for an image area 35. As illustrated in FIG. 22, a white marking material 40 is printed over the image area 35 to create a paper-like uniform background.

It is noted that the white marking material 40 may be printed over the entire image area 35. Thereafter, a marking material 57 is printed on the white marking material 40.

It is noted that the marking material 57 may produce a black image, thereby providing a black/white image for displaying (illuminating) on the optical waveguide 10.

It is noted that the white marking material 40 may have a varied light scattering particle volumetric density, wherein the light scattering particle volumetric density increases proportionally along the surface of the optical waveguide as a distance away from a light source interface of the optical waveguide increases.

The light source interface is the interface (surface) of the optical waveguide that receives incident light from a light source.

With respect to FIG. 22, the light, which is trapped (internally reflected) in the optical waveguide 10, enters the white marking material 40 and gets scattered uniformly by the white marking material 40. The scattered light is then absorbed by the marking material 57, which may produce black or color, in an image-wise fashion. In essence, the image is created by absorption of light through the marking material 57.

Figure 23:
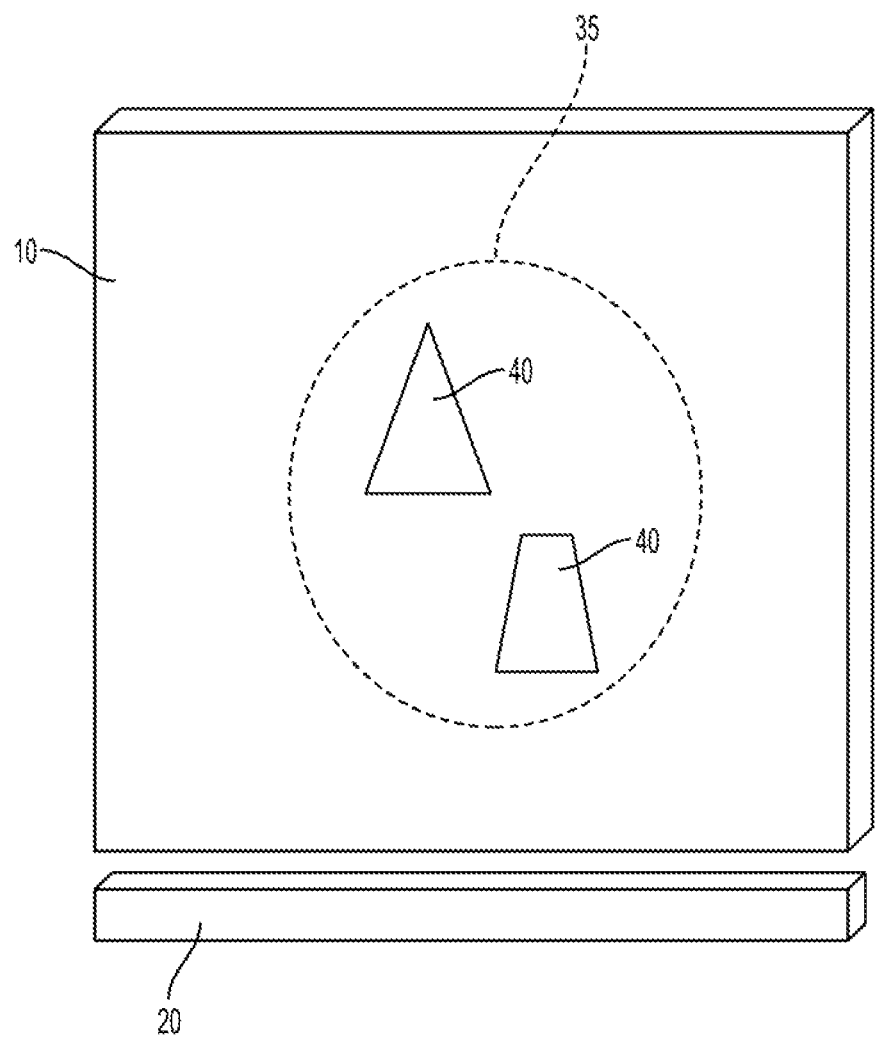
FIG. 23 illustrates an optical waveguide display system displaying a black and white image, printed using a white marking material, from a surface of a single optical waveguide.

FIG. 23 illustrates an optical waveguide 10 capable of providing a black/white image within an image area 35. As illustrated in FIG. 23, a white marking material 40 is printed, in an image-wise fashion, within the image area 35.

With respect to FIG. 23, the light, which is trapped (internally reflected) in the optical waveguide 10, enters the white marking material 40 and gets scattered, in an image-wise fashion, by the white marking material 40. A portion of the scattered light exits the white marking material 40 and is observed by a viewer. In essence, the image is created by scattering of light through scattering particles in the white marking material 40.

It is noted that shading within the image may be provided by the modulation of the amplitude/intensity of the scattering according the intended image.

For example, by controlling an amount of white marking material 40 printed in a specific region of the image area 35, the amount (amplitude/intensity) of scattering can be controlled. More specifically, the more scattering (higher amplitude/intensity), the brighter the image in that region will appear when illuminated with edge lighting.

In contrast, the less scattering (lower amplitude/intensity), the darker the image in that region will appear when illuminated with edge lighting.

The use of a white marking material 40 to create an image enables the effective creation of monochrome images. Also, the use of a white marking material 40 to create an image enables the effective creation of gray level images with large areas of darker areas.

Figure 24:
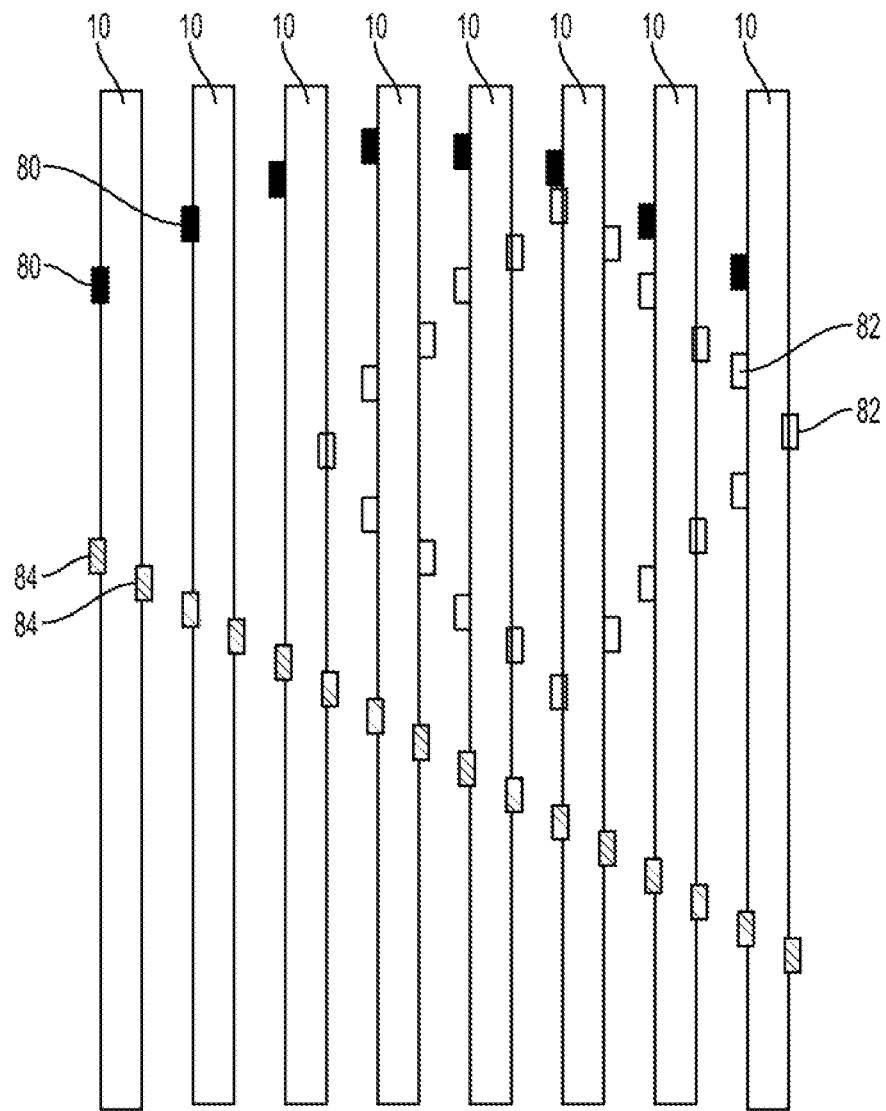
FIG. 24 illustrates multiple optical waveguides to create edge illuminated three-dimensional image/object display.

FIG. 24 illustrates multiple optical waveguides 10 used in creating a three-dimensional image. As illustrated in FIG. 24, each optical waveguide 10 has a portion of an image printed thereon.

For example, as illustrated in FIG. 24, a portion of image 80 is printed on one surface of each optical waveguide 10. Moreover, as illustrated in FIG. 24, a portion of image 82 is printed on both sides of a subset of the optical waveguides 10. Lastly, as illustrated in FIG. 24, a portion of image 84 is printed on both sides of each optical waveguide 10.

The images, in FIG. 24, may be created using any of the various printing processes (color, monochrome, surface roughness, bulk scattering, various color/white layering schemes, etc.) as described above.

Moreover, each optical waveguide 10 may be printed independently and may be printed on one surface or printed on both surfaces.

It is noted that optical waveguides 10 may be spaced uniformly. Moreover, if the images are printed on both surfaces of the optical waveguide, the spacing between the optical waveguides can be adjusted to optimize viewing and/or the thickness of the optical waveguides can be adjusted to optimize viewing.

It is further noted that the images should be sparse such that there is plenty of transparent viewing area for the images deep in the bulk to be visible.

As illustrated in FIG. 24, each image on each optical waveguide represents a slice of the three-dimensional image or object. The image or object can be the contour of the outer surface with full color. Moreover, the image or object can include inside structures to give an appearance of hollowness.

With respect to the various embodiments described above, the optical waveguides utilized in illuminating the printed on images can be readily re-used by removing the marking material from the optical waveguide.

In other words, an image on an optical waveguide intended for edge illumination can be first printed using various marking materials such as liquid inks, UV curable inks, toner, and/or solid inks.

Thereafter, the printed on image can be removed from the optical waveguide without degrading the optical quality of the surfaces. After the surface(s) of the optical waveguide is(are) refreshed, the optical waveguide can be reused for printing a new image.

For example, if UV curable ink is utilized as the marking material, a solvent or cleaning solution, such as acetone, which is not going to harm the optical waveguide material can be used with very little mechanical scrubbing to remove the printed on UV curable ink. If necessary, the optical waveguide can be repaired for minor scratches before being re-used.

In another example, if a hard glass is utilized as the optical waveguide, both chemical solvents, such as acetone, and mechanical agitation can be used to remove the marking material on the surface.

The above cleaning processes can also be used to remove only a portion of the marking material. Moreover, if the optical waveguide includes both engraved images and printed on images, the above cleaning processes can be used to remove the marking material without disturbing the engraved image.

Lastly, the above cleaning processes can be used to remove the marking material from a dual sided (surface) printed optical waveguide to remove the marking material from both surfaces or remove the marking material from one surface.

The re-usability of the optical waveguide surfaces enables (1) test printing processes for reliability and correctness; (2) preview an image with the optical waveguide and lighting before committing to utilization; (3) trial use wherein a user can print and make a temporary optical waveguide display, use it for a short period before making a permanent one; (4) renting, wherein a durable optical waveguide can be used to print custom images and allow a customer to rent; (5) reuse, wherein the content can be changed when desired; and (6) combining engraving with printing, wherein only the content that is not intended to be permanent is removed.

It is noted that in the various embodiment described above, the optical waveguide is provided with edge lighting to effectuate the illumination of the images printed thereon.

Edge lighting is the illumination of the optical waveguide at the optical waveguide side edge or optical waveguide light source interface. The optical waveguide side edge or optical waveguide light source interface is substantially normal to the surface upon which the images are printed.

The optical waveguide side edge or optical waveguide light source interface is preferably a smooth surface and the angle of incidence of the light upon the optical waveguide side edge or optical waveguide light source interface is greater than the critical angle of the air-optical waveguide boundary so that the light can be totally internally reflected within the optical waveguide.

The edge lighting may be provided by a single light source or multiple light sources.

Moreover, the edge lighting may be provided at multiple optical waveguide side edges or optical waveguide light source interfaces.

It is further noted that the optical waveguides may be flat planes, curved surfaces, or enclosed objects, which are suitable for displaying images.

It is also noted that the marking materials, described above, may be liquid inks, UV curable inks, toner, and/or solid inks.

It is additionally noted that the white marking material may be a white colored liquid ink, a white colored UV curable ink, a white colored toner, and/or a white colored solid ink that has light scattering properties.

Moreover, the white marking material may not have a white color, but the marking material being referred to a white marking material may have no discernible color and be a clear liquid ink, a clear UV curable ink, a clear toner, and/or a clear solid ink that has light scattering properties. In addition, the white marking material may be a clear liquid ink, a clear UV curable ink, a clear toner, and/or a clear solid ink that has light scattering particles embedded therein.

The non-white marking material may be a colored liquid ink, a colored UV curable ink, a colored toner, and/or a colored solid ink, or the non-white marking material may be a black liquid ink, a black UV curable ink, a black toner, and/or a black solid ink.

It is noted that the non-white marking material may have light absorption properties.

It is further noted that the non-white marking material may have include infrared material to provide infrared illumination, ultraviolet light material to provide ultraviolet illumination, or fluorescent material to provide non-white illumination.

It is also noted that, in the various embodiments described above, that the white marking material and the non-white marking material is printed or formed on the optical waveguide in an image-wise manner. In other words, the marking material is only printed formed in regions of the surface of the optical waveguide wherein an image is to be illuminated.

On the other hand, if a white background is to be created, the white marking material is printed or formed on the entire surface of the optical waveguide and only the non-white marking material is printed or formed in an image-wise manner.

Printing or forming in an image-wise manner means that the marking material is placed in accordance with the image data of the image to be illuminated.

It is also noted that, in the various embodiments described above and in the claims set forth below, an optical waveguide refers to a physical structure (planar, strip, or fiber), a transparent medium (planar, strip, or fiber), or a translucent medium (planar, strip, or fiber) that guides electromagnetic waves (light) in the optical spectrum.

Moreover, in the various embodiments described above and in the claims set forth below, an optical waveguide refers to a physical structure (planar, strip, or fiber), a transparent medium (planar, strip, or fiber), or a translucent medium (planar, strip, or fiber) that supports total internal reflection of light as the light propagates through the medium. Examples of optical waveguides may be glass, acrylic, fiber optics, etc.

Furthermore, in the various embodiments described above and in the claims set forth below, an optical waveguide refers to a physical structure (planar, strip, or fiber), a transparent medium (planar, strip, or fiber), or a translucent medium (planar, strip, or fiber) that supports total internal reflection of light as the light propagates through the medium. Examples of optical waveguides may be glass, acrylic, fiber optics, etc.

It is also noted that, in the various embodiments described above and in the claims set forth below, the forming of materials on the optical waveguide may be realized by depositing one or more marking materials using an inkjet printer, an inkjet printing process, a xerographic printer, a xerographic printing process, a screen printer, a screen printing process, a solid ink printer, a solid ink printing process, a three-dimensional printer, a three-dimensional printing process, a plotter, a brush or marking material applicator.

It is further noted that, in the various embodiments described above, the forming of materials may be realized by forming or depositing one or more marking materials on a thin, light transmissive substrate using an inkjet printer, an inkjet printing process, a xerographic printer, a xerographic printing process, a screen printer, a screen printing process, a solid ink printer, a solid ink printing process, a three-dimensional printer, a three-dimensional printing process, a plotter, a brush or marking material applicator, wherein the thin, light transmissive substrate is attached, by adhesive, electrostatic, or other means, to the optical waveguide to enable easy mechanical removal of the marking material by detaching the thin, light transmissive substrate from the optical waveguide.

Figure 25:
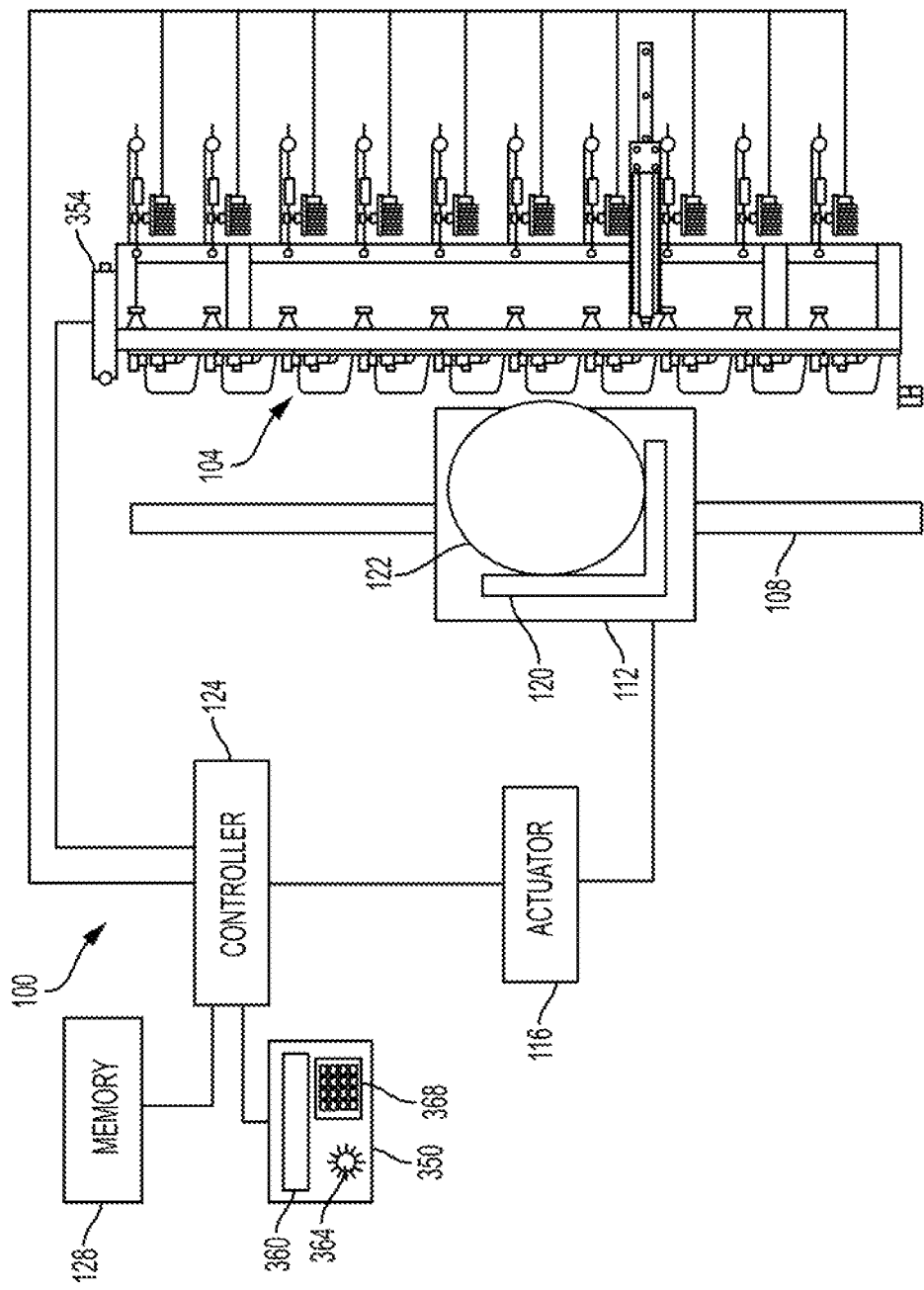
FIG. 25 illustrates an exemplary printing system configured to print on a three-dimensional object.

FIG. 25 illustrates an exemplary printing system 100 configured to print on a three-dimensional object or to print on an optical waveguide utilizing the processes described above. The printing system 100 includes an array of print heads 104, a support member 108, a member 112 movably mounted to the support member 108, an actuator 116 operatively connected to the movably mounted member 112, an object holder 120 configured to mount to the movably mounted member 112, and a controller 124 operatively connected to the plurality of print heads and the actuator.

As shown in FIG. 25, the array of print heads 104 is arranged in a two-dimensional array. Each print head is fluidly connected to a supply of marking material (not shown) and is configured to eject marking material received from the supply. Some of the print heads can be connected to the same supply or each print head can be connected to its own supply so each print head can eject a different marking material. The controller 124 is also operatively connected to an optical sensor 350.

The support member 108 is positioned to be parallel to a plane formed by the array of print heads and, as shown in the figure, is oriented so one end of the support member 108 is at a higher gravitational potential than the other end of the support member. This orientation enables the printing system 100 to have a smaller footprint than an alternative embodiment that horizontally orients the array of print heads and configures the support member, movably mounted member, and object holder to enable the object holder to pass objects past the horizontally arranged print heads so the print heads can eject marking material downwardly on the objects.

The member 112 is movably mounted to the support member 108 to enable the member to slide along the support member. In some embodiments, the member 112 can move bi-directionally along the support member. In other embodiments, the support member 108 is configured to provide a return path to the lower end of the support member to form a track for the movably mounted member.

The actuator 116 is operatively connected to the movably mounted member 112 so the actuator 116 can move the moveably mounted member 112 along the support member 108 and enable the object holder 120 connected to the moveably mounted member 112 to pass the array of print heads 104 in one dimension of the two-dimensional array of print heads. In the embodiment depicted in the figure, the object holder 120 moves an object 122 along the length dimension of the array of print heads 104.

The controller 124 is configured with programmed instructions stored in a memory 128 operatively connected to the controller so the controller can execute the programmed instructions to operate components in the printing system 100.

Thus, the controller 124 is configured to operate the actuator 116 to move the object holder 120 past the array of print heads 104 and to operate the array of print heads 104 to eject marking material onto objects held by the object holder 120 as the object holder passes the array of print heads 104. Additionally, the controller 124 is configured to operate the inkjets within the print heads of the array of print heads 104 so they eject drops with larger masses than the masses of drops ejected from such print heads.

In one embodiment, the controller 124 operates the inkjets in the print heads of the array of print heads 104 with firing signal waveforms that enable the inkjets to eject drops that produce drops on the object surfaces having a diameter of about seven to about ten mm. This drop size is appreciably larger than the drops that produced drops on the material receiving surface having a mass of about 21 ng.

Figure 28:
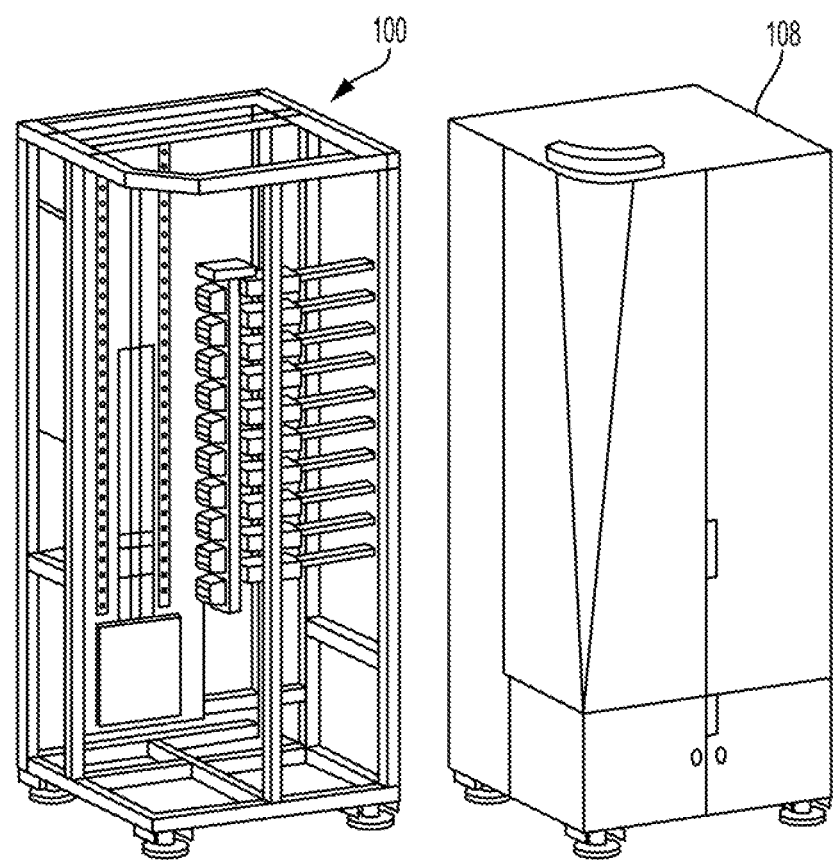
FIG. 28 illustrates a cabinet within which one of the embodiments shown in FIG. 26 or FIG. 27 can be installed.

The system configuration shown in FIG. 25 is especially advantageous in a number of aspects. For one, as noted above, the vertical configuration of the array of print heads 104 and the support member 108 enables the system 100 to have a smaller footprint than a system configured with a horizontal orientation of the array and support member. This smaller footprint of the system enables the system 100 to be housed in a single cabinet 180, as depicted in FIG. 28, and installed in non-production outlets. Once installed, various object holders, as described further below, can be used with the system to print a variety of goods that are generic in appearance until printed.

Another advantageous aspect of the system 100 shown in FIG. 25 is the gap presented between the objects carried by the object holder 120 and the print heads of the array of print heads 104.

Additionally, the controller 124 can be configured with programmed instructions to operate the actuator 116 to move the object holder at speeds that attenuate the air turbulence in the gap between the print head and the object surface used in the system 100.

Figure 26:
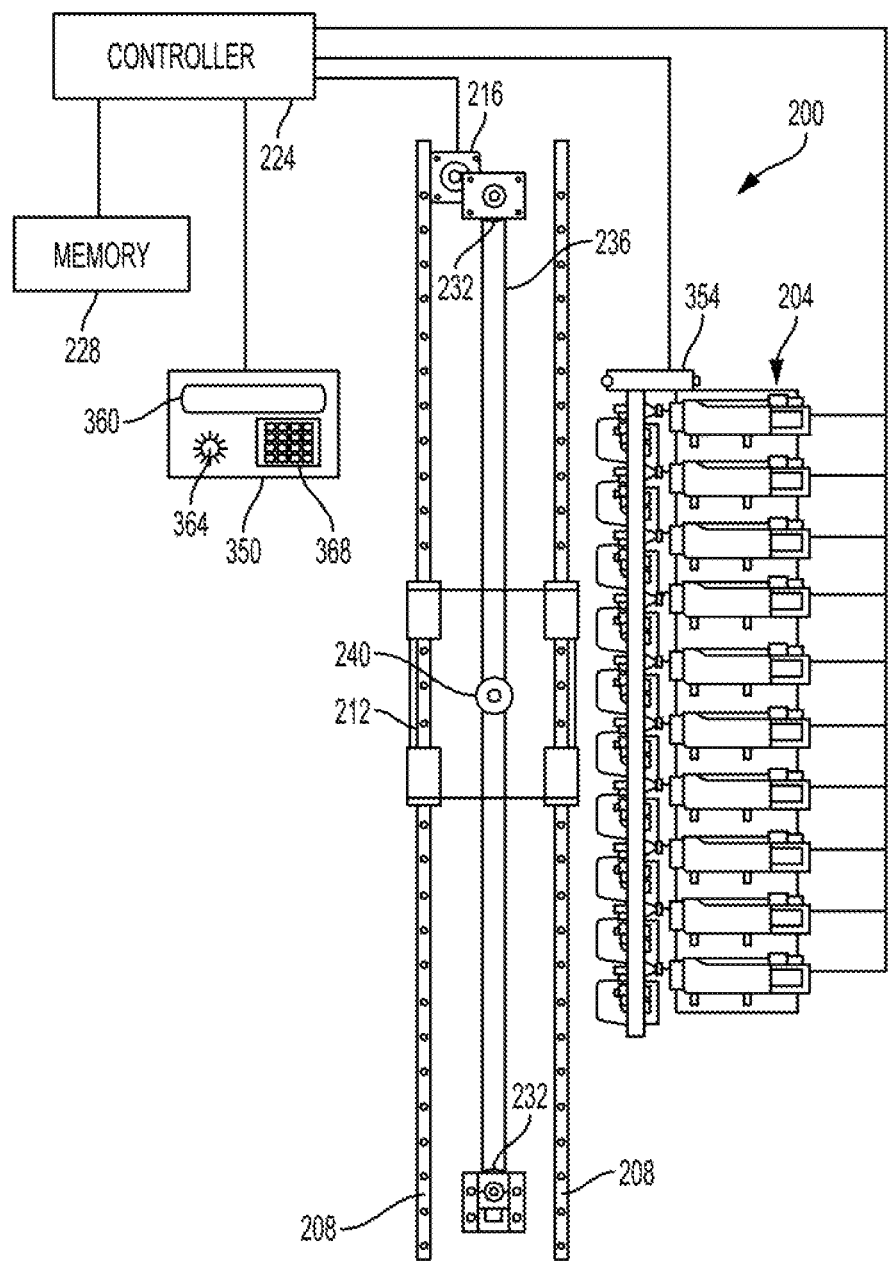
FIGS. 26 and 27 illustrate other embodiments of the printing system of FIG. 25 that use a double support member to enable movement of objects past an array of print heads.

An alternative embodiment of the system 100 is shown in FIG. 26. In this alternative embodiment 200, the support member is a pair of support members 208 about which the moveably mounted member 212 is mounted.

This embodiment includes a pair of fixedly positioned pulleys 232 and a belt 236 entrained about the pair of pulleys to form an endless belt. The moveably mounted member 212 includes a third pulley 240 that engages the endless belt to enable the third pulley 240 to rotate in response to the movement of the endless belt moving about the pair of pulleys 232 to move the moveably mounted member and the object holder 220.

In this embodiment, the actuator 216 is operatively connected to one of the pulleys 232 so the controller 224 can operate the actuator to rotate the driven pulley and move the endless belt about the pulleys 232. The controller 224 can be configured with programmed instructions stored in the memory 228 to operate the actuator 216 bi-directionally to rotate one of the pulleys 232 bi-directionally for bi-directional movement of the moveably mounted member 212 and the object holder 220 past the array of print heads 204.

Figure 27:
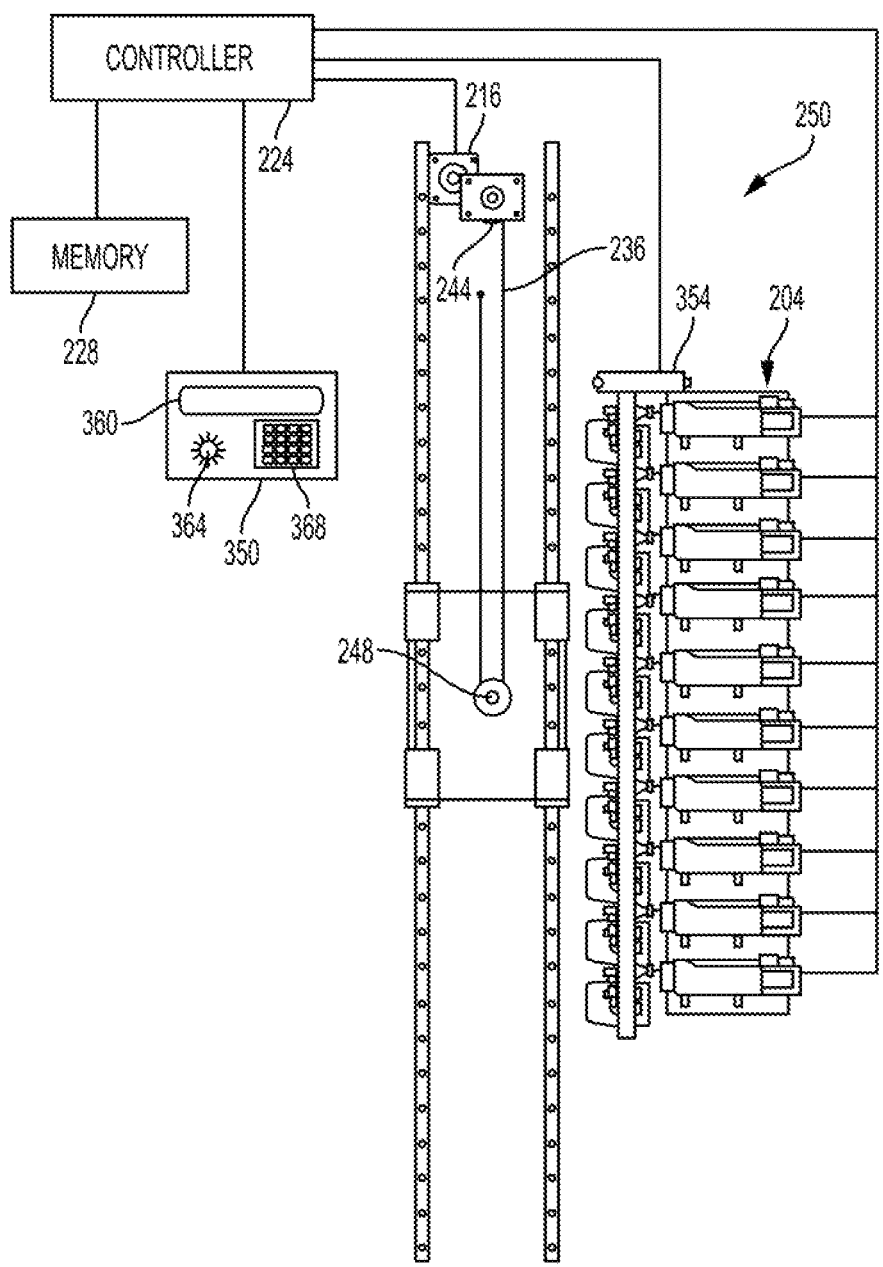

In another alternative embodiment shown in FIG. 27, one end of the belt 236 is operatively connected to a take-up reel 244 that is operatively connected to the actuator 216. The other end of the belt 236 is fixedly positioned. The controller 224 is configured with programmed instructions stored in the memory 228 to enable the controller 224 to operate the actuator 216 to rotate the take-up reel 244 and wind a portion of the length of the belt about the take-up reel 244.

The belt 244 also engages a rotatable pulley 248 mounted to the moveably mounted member 212. Since the other end of the belt 236 is fixedly positioned, the rotation of the reel 244 causes the moveably mounted member 212 to move the object holder past the array of print heads.

When the controller 224 operates the actuator 216 to unwind the belt from the reel 224, the moveably mounted member 212 descends and enables the object holder to descend past the array of print heads 204. This direction of movement is opposite to the direction in which the object holder moved when the actuator was operated to take up a length of the belt 236.

These configurations using a belt to move the moveably mounted member differ from the one shown in FIG. 25 in which the controller 124 operates a linear actuator to move the moveably mounted member 112 and the object holder 120 bi-directionally past the array of print heads.

With to the printing device described above, the printing systems may include a UV curing station below the array of print heads when UV curable inks are being utilized as a marking material. By including a UV curing station in the print system, a layer of UV curable ink can be deposited, cured, and thereafter, a subsequent layer of UV curable ink can be deposited, thereby building a three-dimensional layered body of cured ink. In other words, after each layer of UV curable ink is deposited, the deposited layer is cured, thereby enabling the depositing of another layer so as to build depth into the deposited UV curable ink so that a rough surface can be produced.

Figure 29:
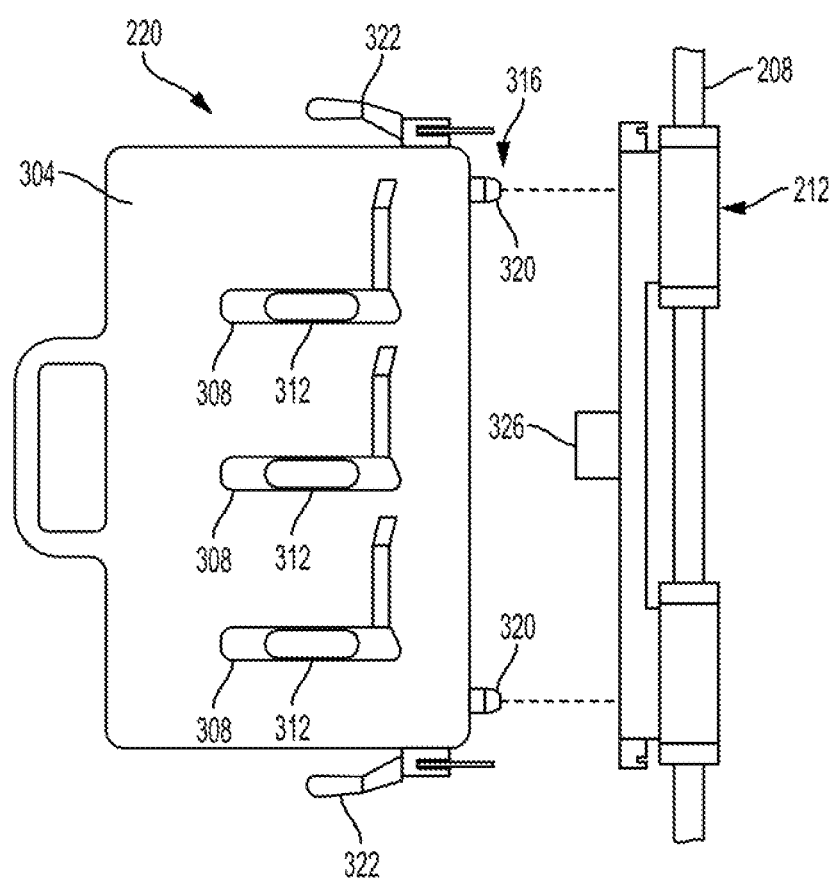
FIG. 29 through FIG. 32 illustrate the object holder and the moveably mounted member shown in FIG. 26 or FIG. 27.

An example of an object holder 220 is shown in FIG. 29. The object holder 220 includes a plate 304 having apertures 308 in which objects 312, which are golf club heads in the figure, are placed for printing. A latch 316 is configured for selectively mounting the object holder 220 to the movably mounted member 212. The latch 316 includes locating features 320 to aid in properly positioning the object holder 220 for securing the holder to the member 212, which is supported by members 208 as shown in FIG. 26.

Once properly positioned, levers 322 operate the latch 316 to secure the holder 220 to the member 212. As shown in the figure, member 212 includes an input device 326 for obtaining an identifier from the object holder 220 as further described below.

Figure 30:
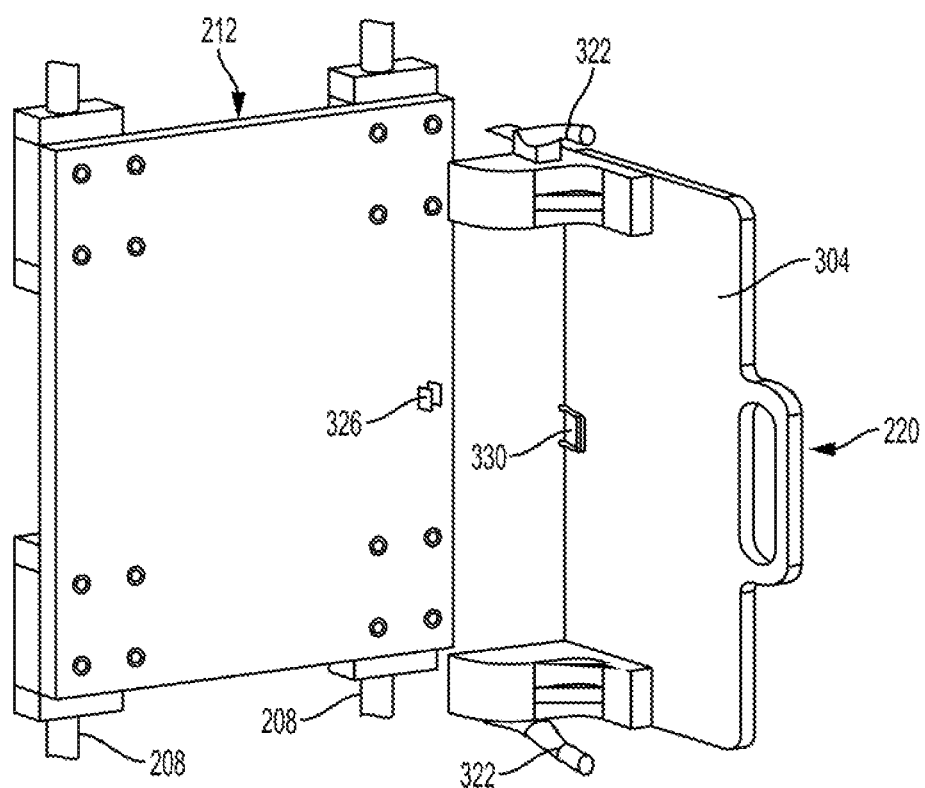

A perspective view of the object holder 220 is shown in FIG. 30. In FIG. 30, an identification tag 330 on a surface of the object holder 220 faces the input device 326 on the movably mounted member 212 when the holder is secured to the member 212. The input device 326 is operatively connected to the controller 224, shown in FIGS. 26 and 27, to communicate an identifier from the identification tag 330 to the controller. The controller is further configured to operate the array of print heads 204 and the actuator 216 (FIGS. 26 and 27) with reference to the identifier received from the input device 326 of the movably mounted member 212.

As used in this document, "identification tag" means machine-readable indicia that embody information to be processed by the printing system. The indicia can be mechanical, optical, or electromagnetic.

In one embodiment, the identification tag 330 is a radio frequency identification (RFID) tag and the input device 326 of the movably mounted member is a RFID reader.

In another embodiment, the identification tag 330 is a bar code and the input device 326 of the movably mounted member 212 is a bar code reader.

In another embodiment in which mechanical indicia are used for the identification tag, the indicia are protrusions, indentations, or combinations of protrusions and indentations in a material that can be read by a biased arm following the surface of the identification tag.

The input device 326 in such an embodiment can be a cam follower that converts the position of an arm that follows the mechanical features into electrical signals.

The controller 224 is further configured with programmed instructions stored in the memory 228 to compare the identifier received from the input device 326 of the movably mounted member 212 to identifiers stored in the memory 328 operatively connected to the controller. The controller disables operation of the actuator 216 in response to the identifier received from the input device 326 failing to correspond to one of the identifiers stored in the memory.

In another embodiment, the controller 224 is further configured with programmed instructions stored in the memory 328 to compare the identifier received from the input device 326 of the movably mounted member 212 to identifiers stored in the memory 328.

In this embodiment, the controller 224 disables operation of the print heads in the array of print heads in response to the identifier received from the input device 326 failing to correspond to one of the identifiers stored in the memory 328.

In some embodiments, the controller 224 is configured to disable both the actuator 216 and the array of print heads 204 in response to the identifier received from the input device 326 failing to match one of the identifiers stored in the memory 328.

In all of these embodiments, the controller 224 is operatively connected to a user interface 350 as shown in FIGS. 25 through 27. The interface 350 includes a display 360, an annunciator 364, and an input device 368, such as a keypad.

The controller 224 is configured with programmed instructions to operate the user interface to notify an operator of the failure of the identifier received from the input device 326 to correspond to one of the identifiers in memory. Thus, the operator is able to understand the reason for the disabling of the system.

Additionally, the controller 224 is configured with programmed instructions to operate the user interface 350 to inform the operator of a system status that is incompatible with the identifier received from the input device 326.

For example, the controller 224 monitors the system to detect the configuration of the print heads in the system and the inks being supplied to the print heads. If the inks or the print head configuration is unable to print the objects corresponding to the object holder accurately and appropriately, then the user interface 350 is operated by the controller 224 to generate a message on the display 360 for the operator that inks need to be changed or that the print head array needs to be reconfigured.

The controller 224 is also configured with programmed instructions to operate the user interface 350 to inform the operator of processing that needs to be performed. For example, some identifiers received from the input device 326 indicate that an object requires pre-coating prior to printing or post-coating after the object is printed. The controller 224 in this example operates the user interface 350 to provide a message on the display 360 to the operator regarding either or both of the conditions.

The user interface 350 includes a display 360 for alphanumeric messages, a keypad 368 for entry of data by an operator, and an annunciator 364, such as a warning light or audible alarm, to attract attention to displayed messages.

Figure 31:
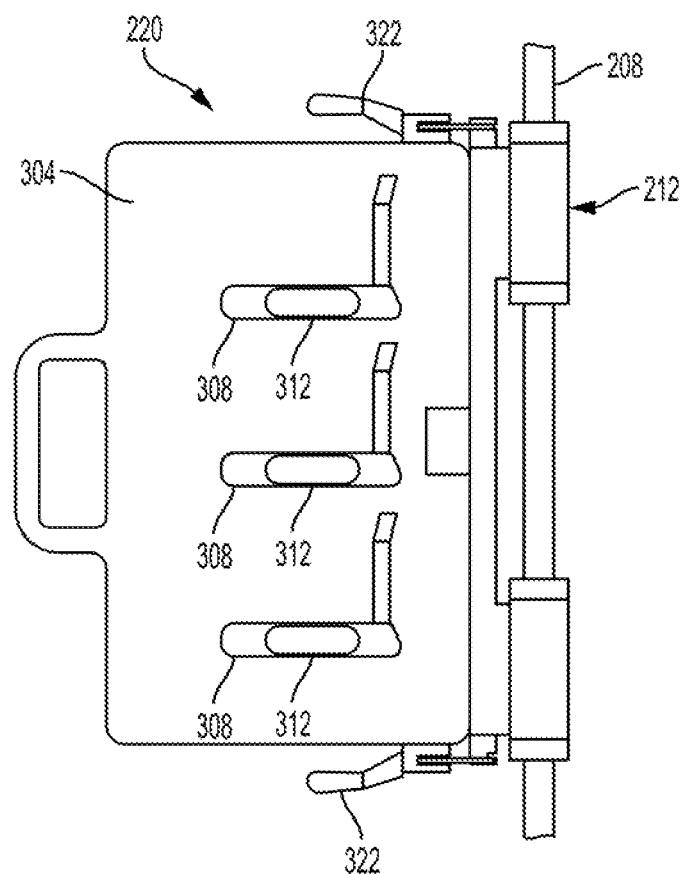
Figure 32:
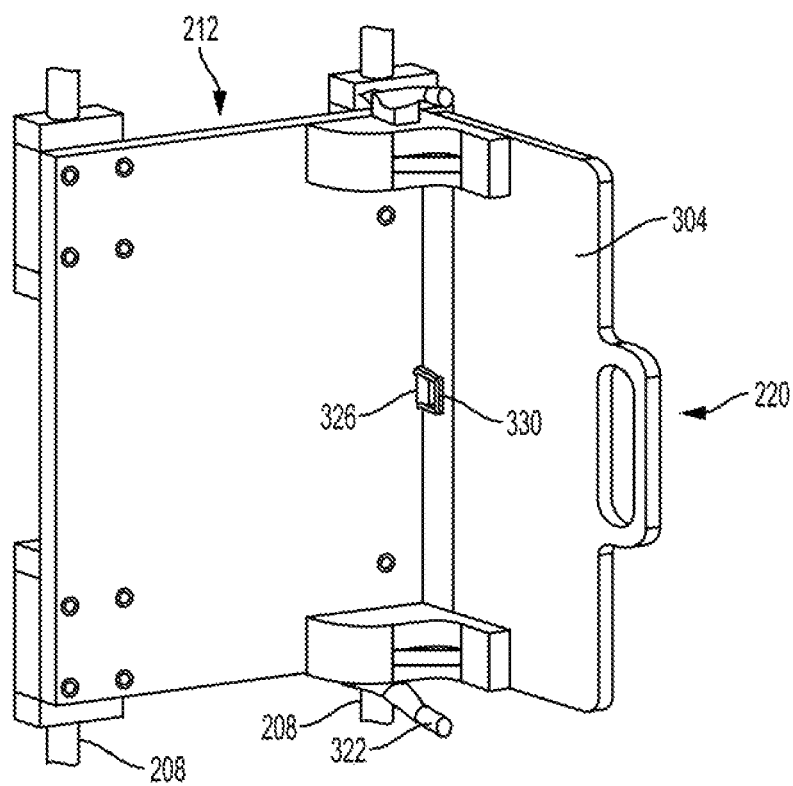

FIG. 31 shows a front view of the object holder 220 secured to the movably mounted member 212, and FIG. 32 shows a rear view of the object holder 220 to the moveably mounted member 212.

Additionally, the controller 224 can be configured to accumulate a count of the number of times an object holder is mounted and dismounted to the movably mounted member 212. This count can be used to obtain and store a number of objects printed by the system 100. This count of printed objects can then be used to order supplies for the continued operation of the system before the supplies are exhausted or to render an accounting of the throughput of the system for various purposes.

FIGS. 33 through 41 depict object holders 220 in various configurations for holding different types of articles and the holders 220 are secured to the movably mounted member 212. The object holders in FIGS. 33, 34, 35, 37, 38, 40 and 41 include at least one aperture that is configured to hold an object for printing by the array of print heads.

Figure 33:
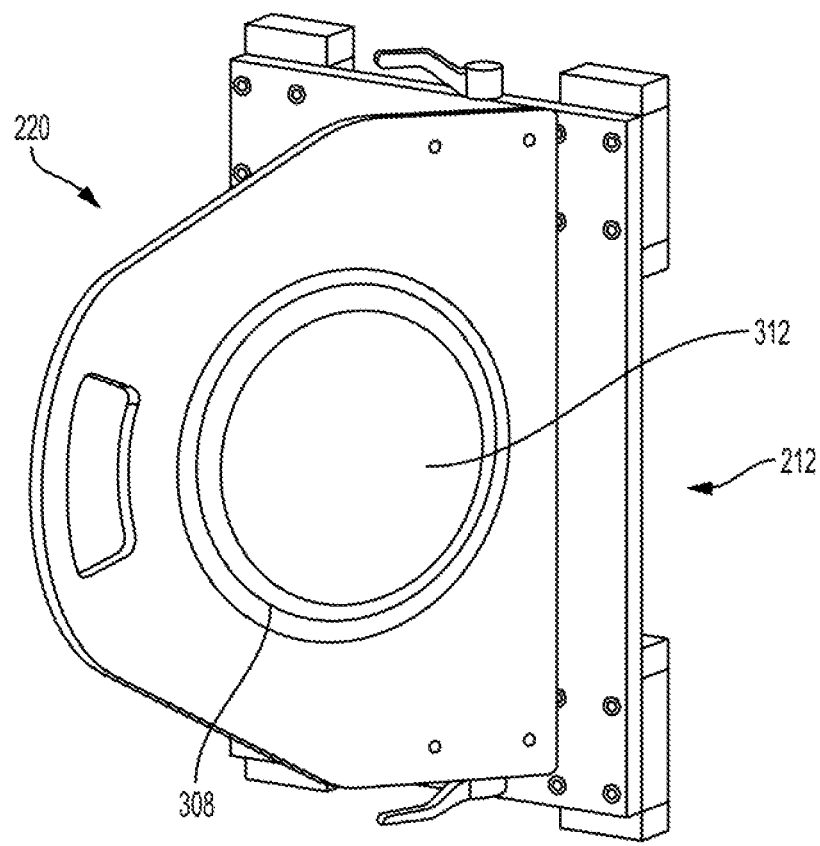
FIG. 33 through FIG. 41 illustrate various configurations of object holders shown in FIG. 26 or FIG. 27 for holding different types of objects.
Figure 34:
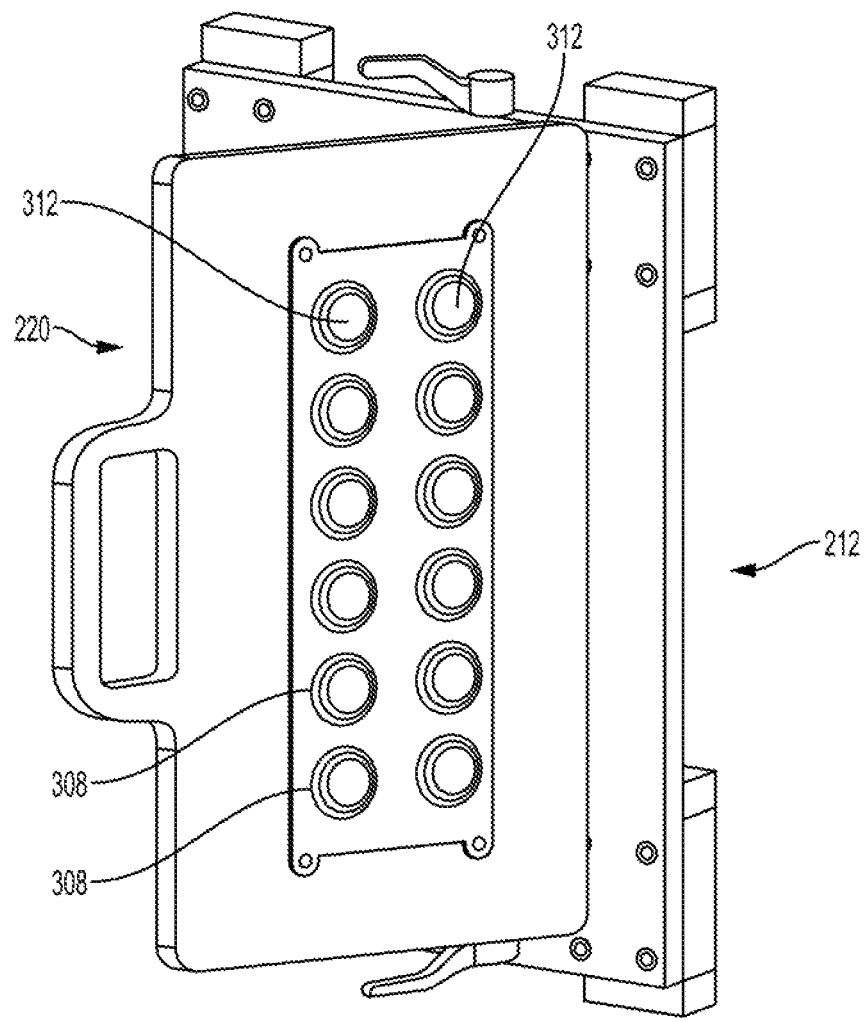
Figure 35:
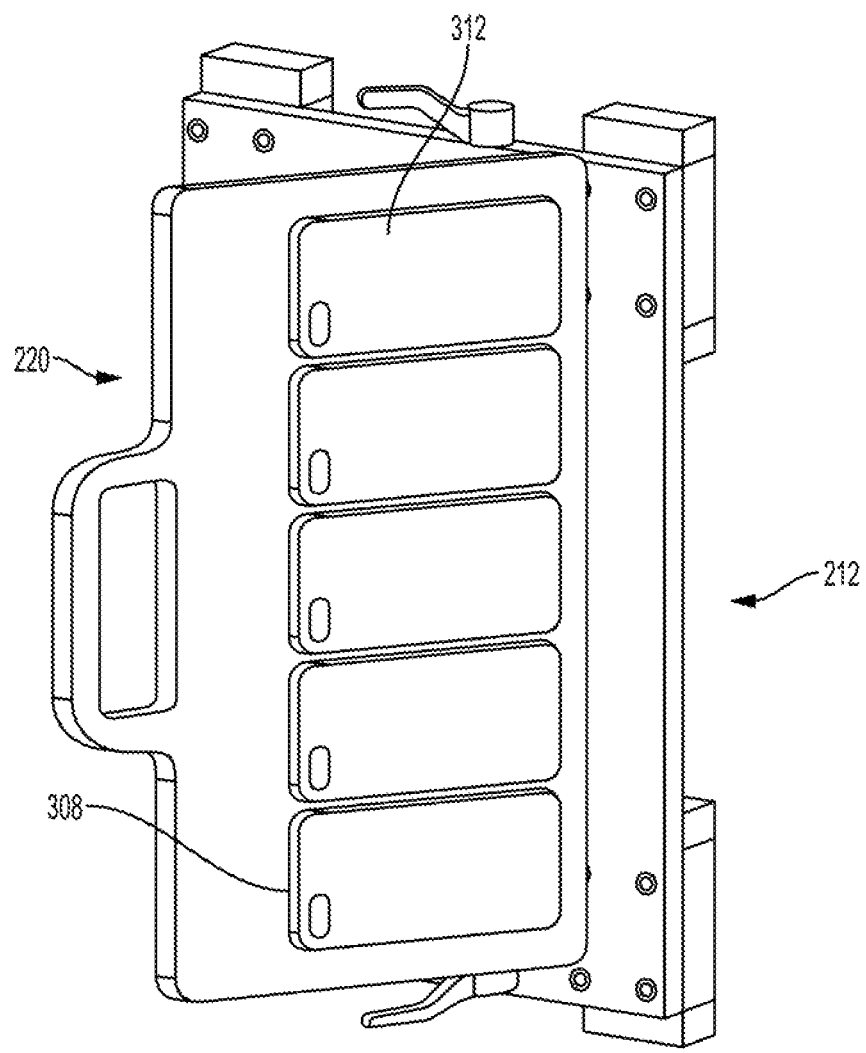
Figure 37:
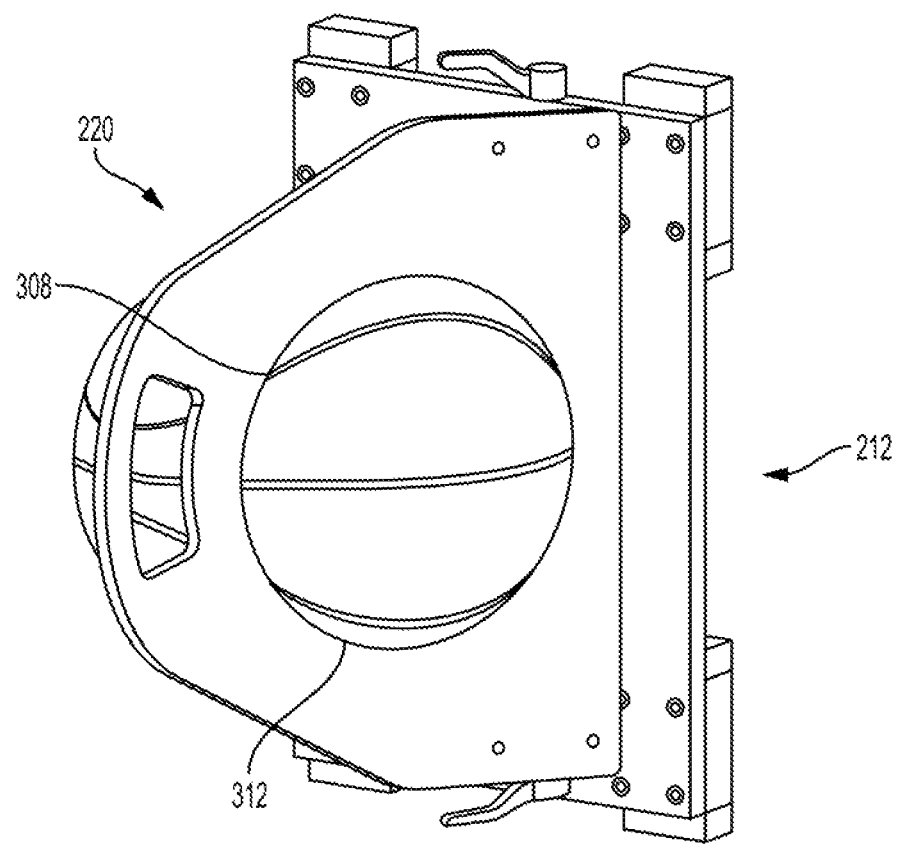
Figure 38:
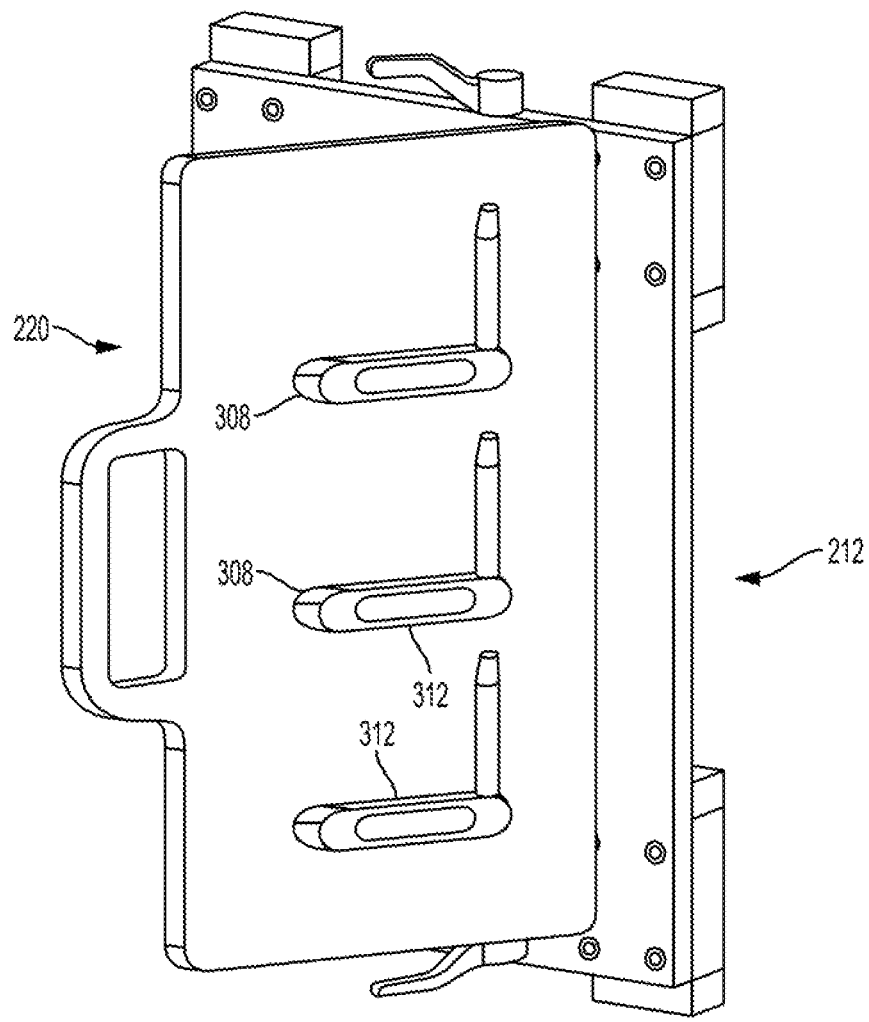

In FIG. 33, the aperture 308 is configured to hold a disk-shaped object 312. In FIG. 34, each aperture 308 in a plurality of apertures is configured to hold a plurality of cap-shaped objects 312. In FIG. 35, each aperture 308 in a plurality of apertures is configured to hold a plurality of cases 312, such as the depicted mobile telephone cases. In FIG. 37, the aperture 308 is configured to hold a spherically shaped object 312. In FIG. 38, each aperture 308 in a plurality of apertures is configured to hold a golf club head 312.

Figure 41:
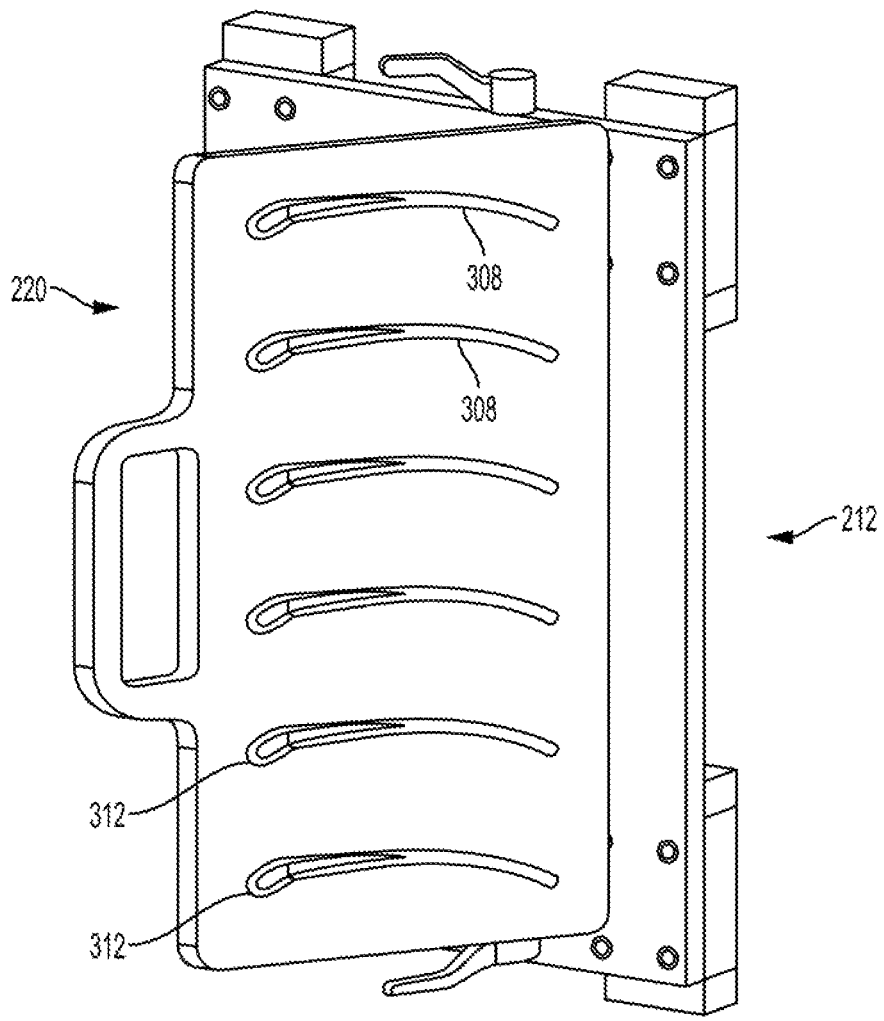

In FIG. 41, each aperture 308 in a plurality of apertures is configured to hold an ear piece 312 of an eyeglasses frame.

Figure 36:
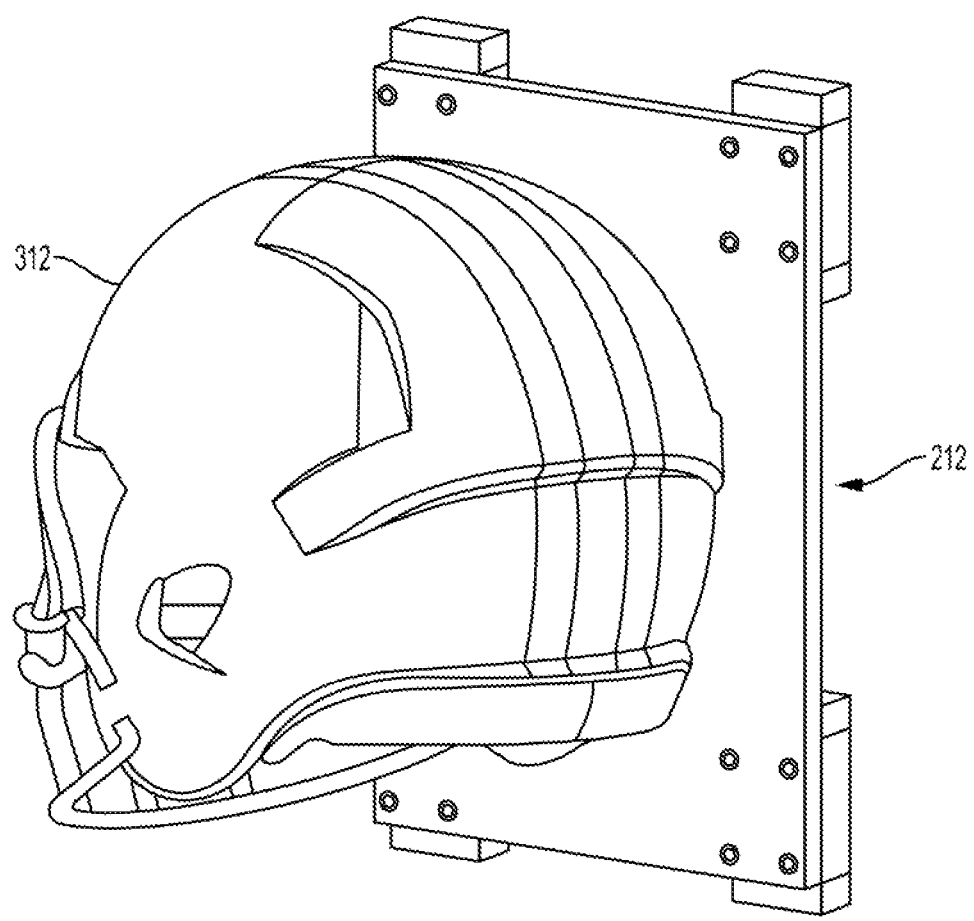
Figure 39:
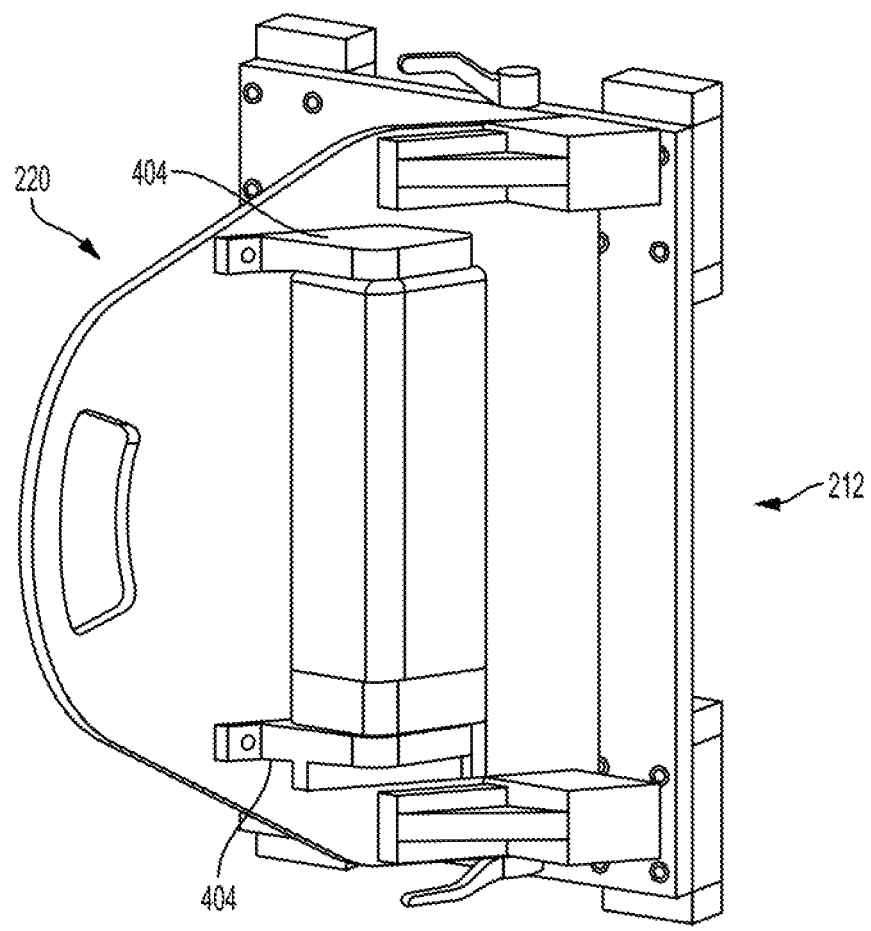

In FIG. 36, the object holder (not visible) is configured to hold head gear. In FIG. 39, the object holder 220 includes a pair of arms 404 configured to secure a rectangular or cylindrical object 312 between them.

As used in this document, the term "arm" refers to a member having two ends with one end being mounted to the object holder and the remainder of the member is configured to hold the object with reference to the object holder.

Figure 40:
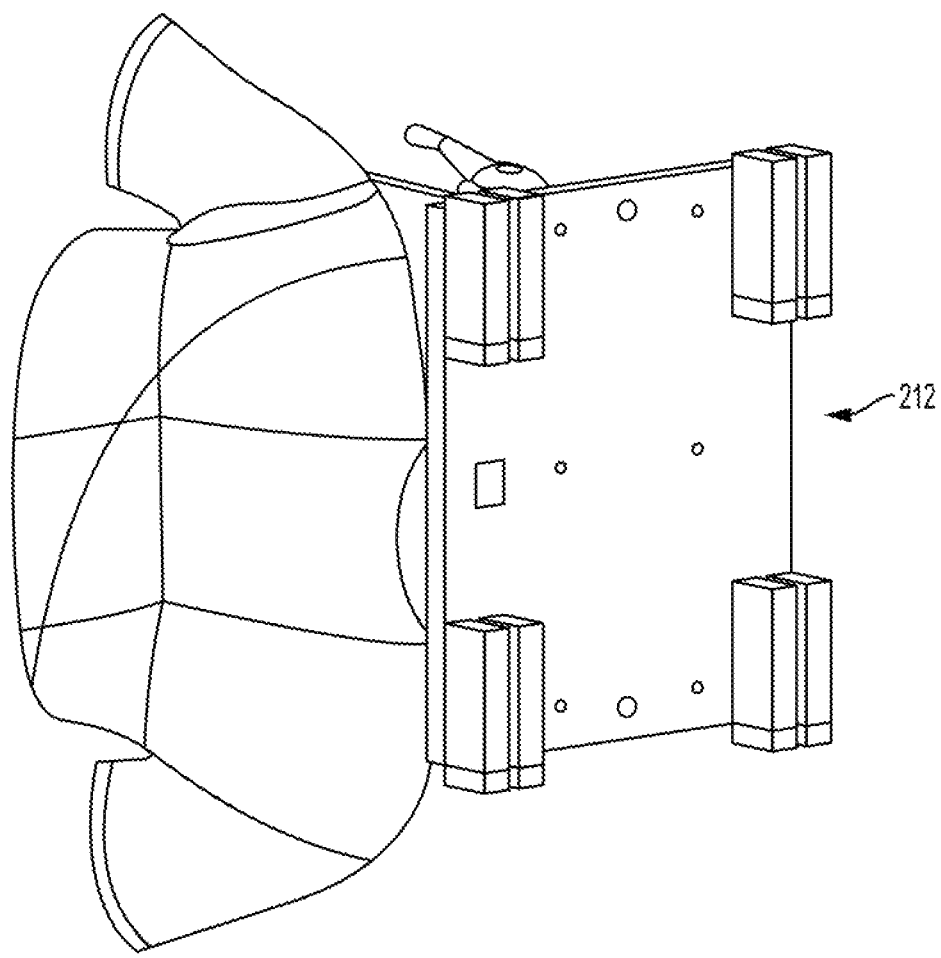

In FIG. 40, the rear side of the moveably mounted member 212 is shown to depict the orientation at which an object holder (not visible) would hold an article of clothing to enable printing of a surface of the article.

Figure 42:
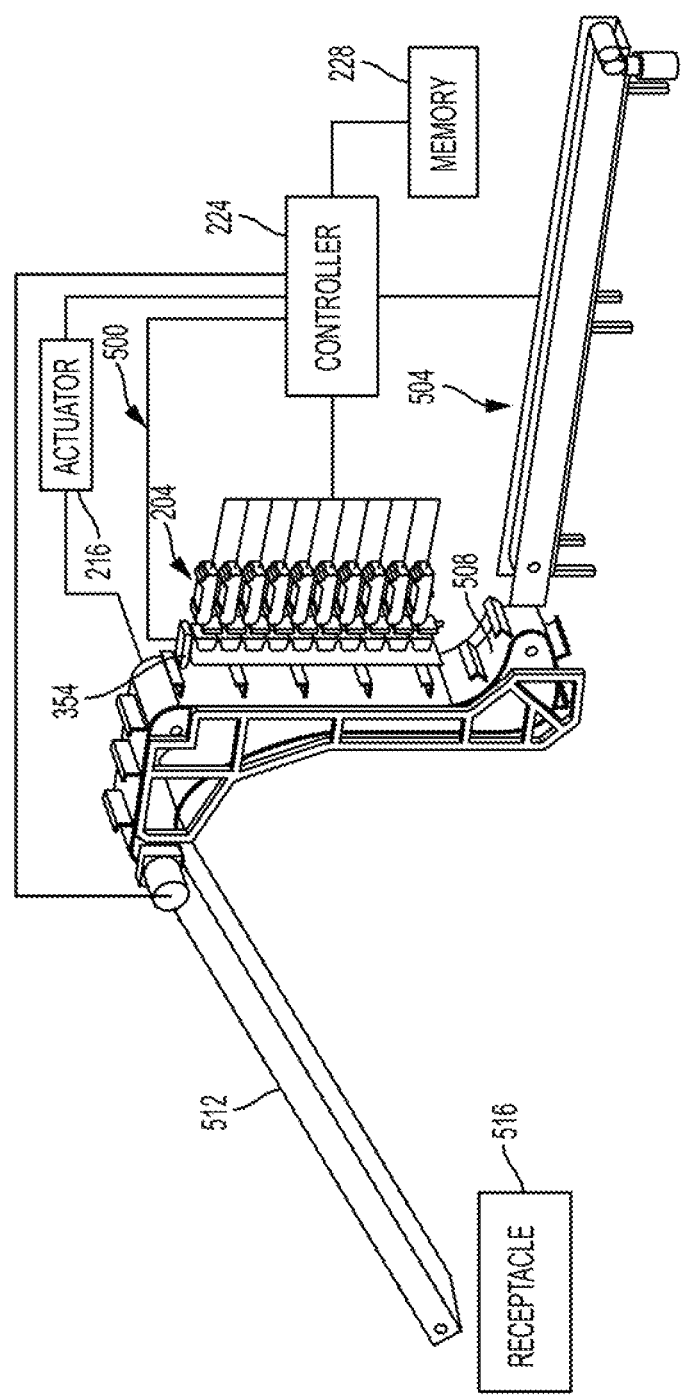
FIG. 42 illustrates an embodiment of the printing system that is useful in a manufacturing environment.

While the printing system 100 described above is especially advantageous in non-production environments, the system 500 depicted in FIG. 42 is more robust and useful in manufacturing environments.

In system 500, a conveyor 504 is configured to deliver objects from a supply of objects (not shown) to an object holder 508. The object holder 508 is configured to receive objects from the conveyor 504. The controller 224 is operatively connected to the conveyor 504, the actuator 216, and the array of print heads 204. The controller 224 is further configured with programmed instructions stored in the memory 228 to operate the conveyor 504 to deliver objects to the object holders 508 and to operate the actuator 216 to move the objects held by the object holders past the array of print heads.

This operation enables the print heads to print the objects as the objects pass the array of print heads 204. A bin can be provided to receive the objects from the object holders 508 after the objects have been printed.

In another embodiment, another conveyor 512 is configured to receive objects from the object holders 508 after the objects held by the object holders are printed by the print heads in the array of print heads 204. The controller 224 is operatively connected to the conveyor 512 and operates the conveyor 512 to transport the printed objects to a location away from the printing system, such as a receptacle 516.

Figure 43:
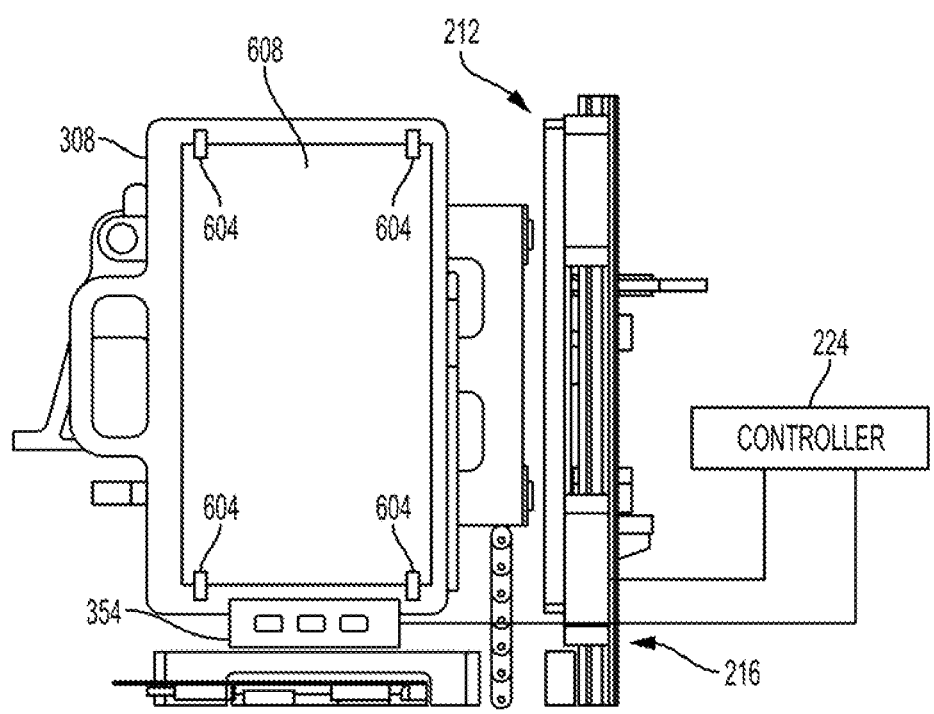
FIG. 43 illustrates an embodiment of an object holder in the printing system of FIG. 25 that enables a media sheet to be printed with a test pattern to verify configuration of the system.

FIG. 43 illustrates shows the object holder 308 of FIG. 35 configured with biased members 604. The biased members can be resilient members formed with a crook at an unattached end of the member that presses downwardly on the surface of the holder 308.

Portions of a sheet of media 608 can be inserted between the biased members and the surface of the holder 308 to enable the sheet to be held against the surface of the holder. An operator can initiate a test or setup mode through the input device of the user interface 350 once the media sheet is installed. In response, the controller 224 operates the actuator 216 to move the media sheet attached to the object holder past the print heads as the controller operates the print heads to eject one or more test patterns onto the media sheet.

The system can include an optical sensor 354, such as a digital camera, that is positioned to generate image data of the test pattern and media sheet after the test pattern has been printed onto the sheet.

The controller 224 executing programmed instructions analyzes the image data of the test pattern on the media sheet to identify maintenance issues, such as print head alignments and inoperative ejectors within print heads. Additionally, the controller 224 verifies the system is appropriately configured to print the objects corresponding to the identifier received from the input device 326 that was read from the identification tag on the object holder.

Figure 44:
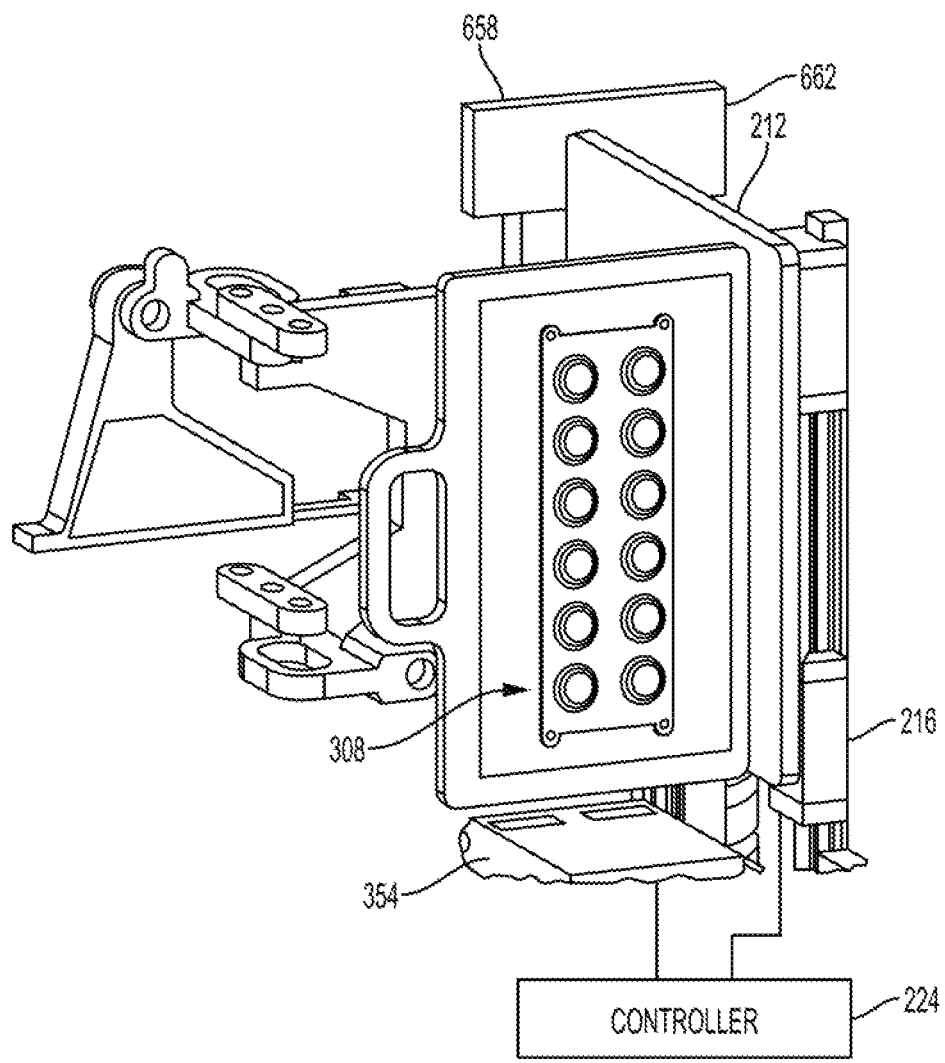
FIG. 44 illustrates an embodiment of a member that is selectively attachable to an object holder in the printing system of FIG. 25 to enable a test pattern to be printed on a surface of the member to verify configuration of the system.

Alternatively, as depicted in FIG. 44, an object holder, such as holder 308, can include a member 658 that is detachably mounted to the object holder and that has a test area 662. The test area 662 of the member 658 is a planar area of a material, such as Mylar, that can be printed by the system, imaged by the optical sensor 354, and analyzed by the controller 224 to identify issues with the configuration of the system.

The systems used in commercial environments print objects in non-production environments. Some of these objects can be quite expensive and the distributor does not want to waste objects by printing test patterns on them. Since some of these objects have curved or intricate geometries, forms replicated the shape and geometry of an object are provided for test runs through the system. These forms are shaped to conform to the general outline of the object, but are made from a material, such as Mylar or the like, that enable images to be printed on the form, imaged, and analyzed to identify maintenance issues or to verify the configuration of the system to print the objects. Once the system has been confirmed as being ready to print objects, the form can be removed and wiped clean so it can used at a later time. As an alternative to the form, a media sheet can be wrapped about an object so it can be printed and the image data analyzed without permanently forming an image on the object since the sheet can be removed before printing the object.

Figure 45:
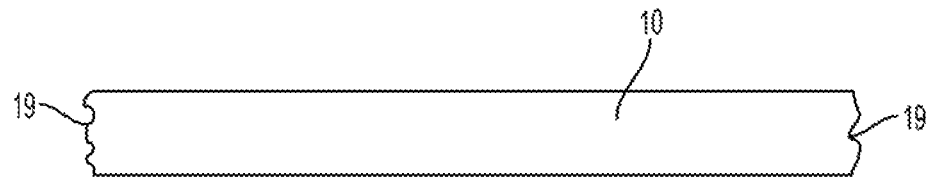
FIG. 45 illustrates a conventional optical waveguide having a rough cut edge.

FIG. 45 illustrates an optical waveguide 10 having cut edges 19, wherein the cut edges 19 are rough. More specifically, a raw panel of optical waveguide material is usually cut from a bigger panel of optical waveguide material. During this cutting process, the edges are very rough after cutting.

One requirement for a good edge illuminated display panel is a clear (optically transparent) edge or smooth edge to enable the illuminating light to enter the panel efficiently. To achieve a clear (optically transparent) edge or smooth edge, conventionally, the edges are polished (especially for glass) or hot melted (using a torch for plastic materials such as acrylic) to create a smooth interface. These methods of edge treatments are slow and typically not conveniently available around a print shop.

Figure 46:
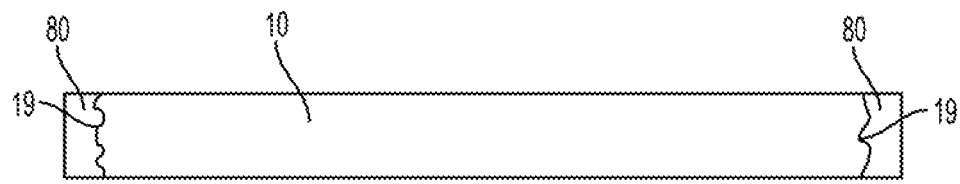
FIG. 46 illustrates an optical waveguide having a conventional rough cut edge smoothed with a marking material to create a smooth optical waveguide light source interface.

Alternatively to the conventional process, the rough edges can be made smooth by flood coating the edge with a clear curable ink 80, as illustrated in FIG. 46, and then the ink is cured. This application and curing of a clear curable ink, smooths the edge so that the edge is a clear (optically transparent) edge.

In a preferred embodiment, the curable ink is a UV curable ink.

It is noted that a curable colored ink may be utilized if color light is desired in illuminating the optical waveguide.

Moreover, it is noted that the multiple curable colored inks may be applied in bands so that based upon the position of the incidence light impinging upon the edge, a variety of colors can be utilized to illuminate the optical waveguide.

By using a clear UV curable fluid (ink) to flood coat the cut edges (19) and curing the clear UV curable fluid (ink) with a UV source, the resulting edge will be smooth and enable good edge illumination.

As noted above, the fluid (ink) fills the roughness of the base material edge due to wetting. The UV/air interface is smooth due to surface tension. Since the UV materials have index of refraction similar to that of the optical waveguide materials, the UV/optical waveguide material interface will not generate substantial back reflection despite the roughness of the interface between the fluid (ink) coating and the optical waveguide material.

Figure 47:
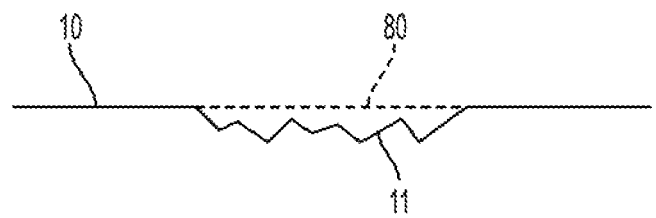
FIG. 47 illustrates an optical waveguide having a conventional engraved image smoothed with a marking material to create a smooth optical waveguide surface.

FIG. 47 illustrates an optical waveguide 10 having an engraved area 11, wherein the engraved area 11 is a rough surface. Due to the engraved area 11, the optical waveguide cannot be re-used in its current condition for illuminating a different image because the engraved area 11 will also illuminate.

To enable the re-usability of the optical waveguide, as illustrated in FIG. 47, the engraved area 11 is flood coated with a clear curable ink 80 and then the ink is cured. This application and curing of a clear curable ink, smooths the surface of the optical waveguide so that the optical waveguide can be re-used to illuminate a different image.

In a preferred embodiment, the curable ink is a UV curable ink.

By using a clear UV curable fluid (ink) to flood coat the engrave area 11 and curing the clear UV curable fluid (ink) with a UV source, the resulting surface will be smooth, thereby enabling total internal reflection at the previously engraved area (11).

In summary, a display device component comprises an optical waveguide having a surface; a first material formed on a portion of the surface of the optical waveguide; and a second material formed on a portion of the first material; the first material having light scattering properties.

The second material may be formed on all of the first material.

The display device component may further comprise being a third material formed on a portion of the first material, the portion of the first material having the second material formed thereon being distinct from the portion of the first material having the third material formed thereon.

The display device component may further comprise being a third material formed on a portion of the second material.

The first material may be a marking material and the second material may be a marking material.

The first material may be a white marking material.

The second material may be a non-white colored marking material.

The third material may be a non-white colored marking material having a color distinct from a color of the second material.

The first material may be a white marking material; the second material may be a first non-white colored marking material; and the third material may be a second non-white colored marking material, the first non-white colored marking material having a color distinct from a color of the second non-white colored marking material.

The first material and the second materials are inks.

The first material and the second materials are toners.

A display device component comprises an optical waveguide having a surface; a first material formed on a portion of the surface of the optical waveguide; and a second material formed on a portion of the first material; the first material having light scattering particles embedded therein.

The display device component may further comprise being a third material formed on a portion of the first material, the portion of the first material having the second material formed thereon being distinct from the portion of the first material having the third material formed thereon.

The display device component may further comprise being a third material formed on a portion of the second material.

The first material may be a white marking material.

The second material may be a non-white colored marking material.

The third material may be a non-white colored marking material having a color distinct from a color of the second material.

The first material may be a white marking material; the second material may be a first non-white colored marking material; and the third material may be a second non-white colored marking material, the first non-white colored marking material having a color distinct from a color of the second non-white colored marking material.

A display device component comprises an optical waveguide having a surface and a light source interface surface; a first material formed on the surface of the optical waveguide; and a second material formed on a portion of the first material; the first material having light scattering particles embedded therein; the first material having a varied light scattering particle volumetric density; the light scattering particle volumetric density increasing proportionally along the surface of the optical waveguide as a distance away from the light source interface surface increases.

The display device component may further comprise being a third material formed on a portion of the first material, the portion of the first material having the second material formed thereon being distinct from the portion of the first material having the third material formed thereon.

A display device component comprises an optical waveguide having a surface; a first material formed on a portion of the surface of the optical waveguide; and a second material formed on the first material; the second material having light scattering properties.

The display device component may further comprise being a third material formed on a portion of the surface of the optical waveguide, the portion of the surface of the optical waveguide having the first material formed thereon being distinct from the portion of the surface of the optical waveguide having the third material formed thereon; the second material being formed on the third material.

The display device component may further comprise being a third material formed between the first material and the second material.

The first material may be a marking material and the second material may be a marking material.

The second material may be a white marking material.

The first material may be a non-white colored marking material.

The third material may be a non-white colored marking material having a color distinct from a color of the first material.

The second material may be a white marking material; the first material may be a first non-white colored marking material; and the third material may be a second non-white colored marking material, the first non-white colored marking material having a color distinct from a color of the second non-white colored marking material.

The first material and the second materials may be inks.

The first material and the second materials may be toners.

A display device component comprises an optical waveguide having a surface; a first material formed on a portion of the surface of the optical waveguide; and a second material formed on a portion of the first material; the second material having light scattering particles embedded therein.

The display device component may further comprise being a third material formed on a portion of the surface of the optical waveguide, the portion of the surface of the optical waveguide having the first material formed thereon being distinct from the portion of the surface of the optical waveguide having the third material formed thereon.

The display device component may further comprise being a third material formed between the first material and the second material.

The second material may be a white marking material.

The first material may be a non-white colored marking material.

The third material may be a non-white colored marking material having a color distinct from a color of the first material.

The second material may be a white marking material; the first material may be a first non-white colored marking material; and the third material may be a second non-white colored marking material, the first non-white colored marking material having a color distinct from a color of the second non-white colored marking material.

A display device component comprises an optical waveguide having a first surface and a second surface; a first material formed on a portion of the first surface of the optical waveguide; a second material formed on a portion of the first material; a third material formed on a portion of the second surface of the optical waveguide; and a fourth material formed on the third material; the first material having light scattering properties; the fourth material having light scattering properties.

The optical waveguide has a first index of refraction and the first material has a second index of refraction, the first index of refraction being substantially equal to the second index of refraction.

The optical waveguide has a first index of refraction and the third material has a second index of refraction, the first index of refraction being substantially equal to the second index of refraction.

The first material may be a marking material and the fourth material may be a marking material.

The first material may be a white marking material and the fourth material may be a white marking material.

The white marking material may be ink.

The white marking material may be toner.

The second material may be a marking material and the third material may be a marking material.

The second material may be a non-white colored marking material and the third material may be a non-white colored marking material.

The non-white colored marking material may be ink.

The non-white colored marking material may be toner.

A display device component comprises an optical waveguide having a first surface and a second surface; a first material formed on a portion of the first surface of the optical waveguide; a second material formed on the first material; a third material formed on a portion of the second surface of the optical waveguide; and a fourth material formed on the third material; the first material having light scattering particles embedded therein; the fourth material having light scattering particles embedded therein.

The optical waveguide has a first index of refraction and the first material has a second index of refraction, the first index of refraction being substantially equal to the second index of refraction.

The optical waveguide has a first index of refraction and the third material has a second index of refraction, the first index of refraction being substantially equal to the second index of refraction.

The first material may be a marking material and the fourth material may be a marking material.

The first material may be a white marking material and the fourth material may be a white marking material.

The second material may be a marking material and the third material may be a marking material.

The second material may be a non-white colored marking material and the third material may be a non-white colored marking material.

A display device comprises an optical waveguide having a surface and a light source interface surface; a light source, the light source directing light upon the light source interface surface at an angle of incidence to provide total internal reflection of the incident light within the optical waveguide; a first material formed on a portion of the surface of the optical waveguide; and a second material formed on the first material; the first material having light scattering properties to frustrate a portion of the total internal reflection of the incident light within the optical waveguide.

The optical waveguide has a first index of refraction and the first material has a second index of refraction, the first index of refraction being substantially equal to the second index of refraction.

The second material has a third index of refraction, the second index of refraction being substantially equal to the third index of refraction.

The first material may be a marking material.

The first material may be a white marking material.

The white marking material may be ink.

The white marking material may be toner.

The second material may be a marking material.

The second material may be a non-white colored marking material.

The non-white colored marking material may be ink.

The non-white colored marking material may be toner.

A display device comprises an optical waveguide having a surface and a light source interface surface; a light source, the light source directing light upon the light source interface surface at an angle of incidence to provide total internal reflection of the incident light within the optical waveguide; a first material formed on a portion of the first surface of the optical waveguide; and a second material formed on the first material; the first material having light scattering particles embedded therein to frustrate a portion of the total internal reflection of the incident light within the optical waveguide.

The optical waveguide has a first index of refraction and the first material has a second index of refraction, the first index of refraction being substantially equal to the second index of refraction, the second material having a third index of refraction, the second index of refraction being substantially equal to the third index of refraction.

The first material may be a marking material.

The first material may be a white marking material.

The second material may be a marking material.

The second material may be a non-white colored marking material.

A display device comprises an optical waveguide having a surface and a light source interface surface; a light source, the light source directing light upon the light source interface surface at an angle of incidence to provide total internal reflection of the incident light within the optical waveguide; a first material formed on of a portion the surface of the optical waveguide; and a second material formed on the first material; the first material having light scattering particles embedded therein to frustrate a portion of the total internal reflection of the incident light within the optical waveguide; the first material having a varied light scattering particle volumetric density; the light scattering particle volumetric density increasing proportionally along the surface of the optical waveguide as a distance away from the light source interface increases.

The first material may be a white marking material.

The second material may be a non-white colored marking material.

A display device comprises an optical waveguide having a surface and a light source interface surface; a light source, the light source directing light upon the light source interface surface at an angle of incidence to provide total internal reflection of the incident light within the optical waveguide; a first material formed on a portion of the first surface of the optical waveguide; and a second material formed on the first material; the second material having light scattering properties to frustrate a portion of the total internal reflection of the incident light within the optical waveguide.

The optical waveguide has a first index of refraction and the first material has a second index of refraction, the first index of refraction being substantially equal to the second index of refraction.

The second material has a third index of refraction, the second index of refraction being substantially equal to the third index of refraction.

The second material may be a marking material.

The second material may be a white marking material.

The white marking material may be ink.

The white marking material may be toner.

The first material may be a marking material.

The first material may be a non-white colored marking material.

The non-white colored marking material may be ink.

The non-white colored marking material may be toner.

A display device comprises an optical waveguide having a surface and a light source interface surface; a light source, the light source directing light upon the light source interface surface at an angle of incidence to provide total internal reflection of the incident light within the optical waveguide; a first material formed on a portion of the surface of the optical waveguide; and a second material formed on the first material; the second material having light scattering particles embedded therein to frustrate a portion of the total internal reflection of the incident light within the optical waveguide.

The optical waveguide has a first index of refraction and the first material has a second index of refraction, the first index of refraction being substantially equal to the second index of refraction, the second material having a third index of refraction, the second index of refraction being substantially equal to the third index of refraction.

The second material may be a marking material.

The second material may be a white marking material.

The first material may be a marking material.

The first material may be a non-white colored marking material.

A display device comprises an optical waveguide having a first surface, a second surface, and a light source interface surface; a light source, the light source directing light upon the light source interface surface at an angle of incidence to provide total internal reflection of the incident light within the optical waveguide; a first material formed on a portion of the first surface of the optical waveguide; a second material formed on the first material; a third material formed on a portion of the second surface of the optical waveguide; and a fourth material formed on the third material; the first material having light scattering properties to frustrate a portion of the total internal reflection of the incident light within the optical waveguide; the fourth material having light scattering properties to frustrate a portion of the total internal reflection of the incident light within the optical waveguide.

The optical waveguide has a first index of refraction and the first material has a second index of refraction, the first index of refraction being substantially equal to the second index of refraction.

The optical waveguide has a first index of refraction and the third material has a second index of refraction, the first index of refraction being substantially equal to the second index of refraction.

The first material may be a marking material and the fourth material may be a marking material.

The first material may be a white marking material and the fourth material may be a white marking material.

The white marking material may be ink.

The white marking material may be toner.

The second material may be a marking material and the third material may be a marking material.

The second material may be a non-white colored marking material and the third material may be a non-white colored marking material.

The non-white colored marking material may be ink.

The non-white colored marking material may be toner.

A display device comprises an optical waveguide having a first surface, a second surface, and a light source interface surface; a light source, the light source directing light upon the light source interface surface at an angle of incidence to provide total internal reflection of the incident light within the optical waveguide; a first material formed on a portion of the first surface of the optical waveguide; a second material formed on the first material; a third material formed on a portion of the second surface of the optical waveguide; and a fourth material formed on the third material; the first material having light scattering particles embedded therein to frustrate a portion of the total internal reflection of the incident light within the optical waveguide; the fourth material having light scattering particles embedded therein to frustrate a portion of the total internal reflection of the incident light within the optical waveguide.

The optical waveguide has a first index of refraction and the first material has a second index of refraction, the first index of refraction being substantially equal to the second index of refraction.

The optical waveguide has a first index of refraction and the third material has a second index of refraction, the first index of refraction being substantially equal to the second index of refraction.

The first material may be a marking material and the fourth material may be a marking material.

The first material may be a white marking material and the fourth material may be a white marking material.

The second material may be a marking material and the third material may be a marking material.

The display device as claimed in claim 12, wherein the second material may be a non-white colored marking material and the third material may be a non-white colored marking material.

A process for making a display device component to enable image specific illumination of an image printed on an optical wave, comprises (a) forming a first material on a portion of an optical waveguide having a surface, the first material having light scattering properties; and (b) forming a second material on the first material.

The optical waveguide has a first index of refraction and the first material has a second index of refraction, the first index of refraction being substantially equal to the second index of refraction.

The second material has a third index of refraction, the second index of refraction being substantially equal to the third index of refraction.

The first material may be a white marking material.

The first material may be formed by an inkjet printing device.

The first material may be formed by a xerographic toner printing device.

The first material may be formed by a solid ink printing device.

The second material may be a non-white colored marking material.

The second material may be formed by an inkjet printing device.

The second material may be formed by a xerographic toner printing device.

The second material may be formed by a solid ink printing device.

A process for making a display device component to enable image specific illumination of an image printed on an optical wave, comprises (a) forming a first material on a portion of an optical waveguide having a surface, the first material having light scattering particles embedded therein; and (b) forming a second material on the first material.

The optical waveguide has a first index of refraction and the first material has a second index of refraction, the first index of refraction being substantially equal to the second index of refraction.

The first material may be a white marking material.

The first material may be formed by an inkjet printing device.

The second material may be a non-white colored marking material.

The second material may be formed by an inkjet printing device.

A process for making a display device component to enable image specific illumination of an image printed on an optical wave comprises (a) forming a first material on an optical waveguide having a surface and a light source interface surface, the first material having light scattering particles embedded therein, the first material having a varied light scattering particle volumetric density, the light scattering particle volumetric density increasing proportionally on the surface as a distance away from the light source interface increases; and (b) forming a second material on the first material.

The first material may be a white marking material.

The second material may be a non-white colored marking material.

A process for making a display device component to enable image specific illumination of an image printed on an optical wave comprises (a) forming a first material on a portion of an optical waveguide having a surface; and (b) forming a second material on the first material, the second material having light scattering properties.

The optical waveguide has a first index of refraction and the first material has a second index of refraction, the first index of refraction being substantially equal to the second index of refraction.

The second material has a third index of refraction, the second index of refraction being substantially equal to the third index of refraction.

The second material may be a white marking material.

The second material may be formed by an inkjet printing device.

The second material may be formed by a xerographic toner printing device.

The second material may be formed by a solid ink printing device.

The first material may be a non-white colored marking material.

The first material may be formed by an inkjet printing device.

The first material may be formed by a xerographic toner printing device.

The first material may be formed by a solid ink printing device.

A process for making a display device component to enable image specific illumination of an image printed on an optical wave comprises (a) forming a first material on a portion of an optical waveguide having a surface; and (b) forming a second material on the first material, the second material having light scattering particles embedded therein.

The optical waveguide has a first index of refraction and the first material has a second index of refraction, the first index of refraction being substantially equal to the second index of refraction.

The second material may be a white marking material.

The second material may be formed by an inkjet printing device.

The first material may be a non-white colored marking material.

The first material may be formed by an inkjet printing device.

A process for making a display device component to enable image specific illumination of an image printed on an optical wave having a first surface and a second surface, comprises (a) forming a first material on a portion of a first surface of an optical waveguide, the first material having light scattering properties; (b) forming a second material on the first material; (c) forming a third material on a portion of a second surface of the optical waveguide; and (d) forming a fourth material on the third material, the fourth material having light scattering properties.

The optical waveguide has a first index of refraction and the first material has a second index of refraction, the first index of refraction being substantially equal to the second index of refraction.

The second material has a third index of refraction, the second index of refraction being substantially equal to the third index of refraction.

The first material may be a white marking material and the fourth material may be a white marking material.

The first material may be formed by an inkjet printing device and the fourth material may be formed by an inkjet printing device.

The first material may be formed by a xerographic toner printing device and the fourth material may be formed by a xerographic toner printing device.

The first material may be formed by a solid ink printing device and the fourth material may be formed by a solid ink printing device.

The second material may be a non-white colored marking material and the third material may be a non-white colored marking material.

The second material may be formed by an inkjet printing device and the third material may be formed by an inkjet printing device.

The second material may be formed by a xerographic toner printing device and the third material may be formed by a xerographic toner printing device.

The second material may be formed by a solid ink printing device and the third material may be formed by a solid ink printing device.

A process for making a display device component to enable image specific illumination of an image printed on an optical wave, comprises (a) forming a first material on a portion of a first surface of an optical waveguide, the first material having light scattering particles embedded therein; (b) forming a second material on the first material; (c) forming a third material on a portion of a second surface of the optical waveguide; and (d) forming a fourth material on the third material, the fourth material having light scattering particles embedded therein.

The optical waveguide has a first index of refraction and the first material has a second index of refraction, the first index of refraction being substantially equal to the second index of refraction.

The first material may be formed by an inkjet printing device and the fourth material may be formed by an inkjet printing device.

The first material may be formed by a xerographic toner printing device and the fourth material may be formed by a xerographic toner printing device.

The first material may be formed by a solid ink printing device and the fourth material may be formed by a solid ink printing device.

The second material may be formed by an inkjet printing device and the third material may be formed by an inkjet printing device.

The second material may be formed by a xerographic toner printing device and the third material may be formed by a xerographic toner printing device.

The second material may be formed by a solid ink printing device and the third material may be formed by a solid ink printing device.

A display device component comprises an optical waveguide having a surface; and a first material formed on a portion of the surface of the optical waveguide; the first material having a first surface adjacent to the surface of the optical waveguide and a second surface away from the surface of the optical waveguide; the second surface being non-smooth to frustrate a portion of light being internally reflected within the optical waveguide.

The display device component may further comprise being a second material formed on a portion of the surface of the optical waveguide; the second material having a third surface adjacent to the surface of the optical waveguide and a fourth surface away from the surface of the optical waveguide and a second surface away; the fourth surface being non-smooth to frustrate a portion of light being internally reflected within the optical waveguide.

The first material may be a marking material.

The second material may be a marking material.

The first material may be a non-white colored marking material.

The second material may be a non-white colored marking material having a color distinct from a color of the first material.

The first material may be a first non-white colored marking material and the second material may be a second non-white colored marking material, the first non-white colored marking material having a color distinct from a color of the second non-white colored marking material.

The first material may be an ink.

The first material may be a toner.

A display device comprises an optical waveguide having a surface and a light source interface surface; a light source, the light source directing light upon the light source interface surface at an angle of incidence to provide total internal reflection of the incident light within the optical waveguide; and a first material formed on a portion of the surface of the optical waveguide; the first material having a first surface adjacent to the surface of the optical waveguide and a second surface away from the surface of the optical waveguide; the second surface being non-smooth to frustrate a portion of the incident light being totally internally reflected within the optical waveguide.

The display device may further comprise being a second material formed on a portion of the surface of the optical waveguide; the second material having a third surface adjacent to the surface of the optical waveguide and a fourth surface away from the surface of the optical waveguide and a second surface away; the fourth surface being non-smooth to frustrate a portion of the incident light being totally internally reflected within the optical waveguide.

The first material may be a marking material.

The second material may be a marking material.

The first material may be a non-white colored marking material.

The second material may be a non-white colored marking material having a color distinct from a color of the first material.

The first material may be a first non-white colored marking material and the second material may be a second non-white colored marking material, the first non-white colored marking material having a color distinct from a color of the second non-white colored marking material.

The first material may be an ink.

The first material may be a toner.

A process for making a display device component to enable image specific illumination of an image printed on an optical wave, comprises (a) forming a first material on a portion of a surface of an optical waveguide, the first material having a first surface adjacent to the surface of the optical waveguide and a second surface away from the surface of the optical waveguide, the second surface being non-smooth to frustrate a portion of light being internally reflected within the optical waveguide.

The first material may be formed on the portion of the surface of the optical waveguide using a printing process and the non-smooth second surface being formed by printing a halftone image on the optical wave guide using the first material.

A display device comprises a first optical waveguide having a first surface, a second surface, and a first light source interface surface; a second optical waveguide having a third surface, a fourth surface, and a second light source interface surface; a light source, the light source directing light upon the first light source interface surface at an angle of incidence to provide total internal reflection of the incident light within the first optical waveguide; the light source directing light upon the second light source interface surface at an angle of incidence to provide total internal reflection of the incident light within the second optical waveguide; a first material formed on a portion of the first surface of the first optical waveguide; a second material formed on the first material; a third material formed on a portion of the second surface of the first optical waveguide; a fourth material formed on the third material; the first material having light scattering properties to frustrate a portion of the total internal reflection of the incident light within the first optical waveguide; the fourth material having light scattering properties to frustrate a portion of the total internal reflection of the incident light within the first optical waveguide; a fifth material formed on a portion of the third surface of the second optical waveguide; a sixth material formed on the fifth material; a seventh material formed on a portion of the fourth surface of the second optical waveguide; an eighth material formed on the seventh material; the fifth material having light scattering properties to frustrate a portion of the total internal reflection of the incident light within the second optical waveguide; the eighth material having light scattering properties to frustrate a portion of the total internal reflection of the incident light within the second optical waveguide.

The first optical waveguide may be spaced apart from the second optical waveguide.

A distance between the first optical waveguide and the second optical waveguide may be equal to half a thickness of the first optical waveguide.

The first optical waveguide may be parallel to the second optical waveguide.

A display device comprises a plurality of optical waveguides, each optical waveguide having a front surface, a back surface, and a light source interface surface; a light source, the light source directing light upon the light source interface surfaces of each optical waveguide at an angle of incidence to provide total internal reflection of the incident light within each optical waveguide; each optical wave guide having formed thereon a first material formed on a portion of the front surface of each optical waveguide, the first material having light scattering properties to frustrate a portion of the total internal reflection of the incident light within the optical waveguide; each optical wave guide having formed on the first material a second material; each optical wave guide having formed thereon a third material formed on a portion of the back surface of each optical waveguide; each optical wave guide having formed on the third material a fourth material, the fourth material having light scattering properties to frustrate a portion of the total internal reflection of the incident light within the optical waveguide.

A distance between each optical waveguide may be equal to a thickness of an optical waveguide divided by a number of optical waveguides.

Each optical waveguide may be parallel thereto.

A display device comprises a plurality of optical waveguides, each optical waveguide having a front surface, a back surface, and a light source interface surface; a light source, the light source directing light upon the light source interface surfaces of each optical waveguide at an angle of incidence to provide total internal reflection of the incident light within each optical waveguide; each optical wave guide having formed thereon a first material formed on a portion of the front surface of each optical waveguide, the first material having a first surface adjacent to the surface of the optical waveguide and a second surface away from the surface of the optical waveguide, the second surface being non-smooth to frustrate a portion of light being internally reflected within the optical waveguide.

A distance between each optical waveguide may be equal to a thickness of an optical waveguide divided by a number of optical waveguides.

Each optical waveguide may be parallel thereto.

A display device component comprises a first optical waveguide having a first surface and a second surface; a second optical waveguide having a third surface and a fourth surface; a first material formed on a portion of the first surface of the first optical waveguide; a second material formed on the first material; a third material formed on a portion of the second surface of the first optical waveguide; a fourth material formed on the third material; the first material having light scattering properties to frustrate a portion of the total internal reflection of the incident light within the first optical waveguide; the fourth material having light scattering properties to frustrate a portion of the total internal reflection of the incident light within the first optical waveguide; a fifth material formed on a portion of the third surface of the second optical waveguide; a sixth material formed on the fifth material; a seventh material formed on a portion of the fourth surface of the second optical waveguide; an eighth material formed on the seventh material; the fifth material having light scattering properties to frustrate a portion of the total internal reflection of the incident light within the second optical waveguide; the eighth material having light scattering properties to frustrate a portion of the total internal reflection of the incident light within the second optical waveguide.

The first optical waveguide may be spaced apart from the second optical waveguide.

A distance between the first optical waveguide and the second optical waveguide may be equal to half a thickness of the first optical waveguide.

The first optical waveguide may be parallel to the second optical waveguide.

A display device component comprises a plurality of optical waveguides, each optical waveguide having a front surface and a back surface; each optical wave guide having formed thereon a first material formed on a portion of the front surface of each optical waveguide, the first material having light scattering properties to frustrate a portion of the total internal reflection of the incident light within the optical waveguide; each optical wave guide having formed on the first material a second material; each optical wave guide having formed thereon a third material formed on a portion of the back surface of each optical waveguide; each optical wave guide having formed on the third material a fourth material, the fourth material having light scattering properties to frustrate a portion of the total internal reflection of the incident light within the optical waveguide.

A distance between each optical waveguide may be equal to a thickness of an optical waveguide divided by a number of optical waveguides.

Each optical waveguide may be parallel thereto.

A display device component comprises a plurality of optical waveguides, each optical waveguide having a front surface and a back surface; each optical wave guide having formed thereon a first material formed on a portion of the front surface of each optical waveguide, the first material having a first surface adjacent to the surface of the optical waveguide and a second surface away from the surface of the optical waveguide, the second surface being non-smooth to frustrate a portion of light being internally reflected within the optical waveguide; each optical wave guide having formed thereon a second material formed on a portion of the back surface of each optical waveguide; each optical wave guide having formed on the second material a third material, the third material having light scattering properties to frustrate a portion of the total internal reflection of the incident light within the optical waveguide.

A distance between each optical waveguide may be equal to a thickness of an optical waveguide divided by a number of optical waveguides.

Each optical waveguide may be parallel thereto.

A display device component comprises a plurality of optical waveguides, each optical waveguide having a front surface and a back surface; each optical wave guide having formed thereon a first material formed on a portion of the front surface of each optical waveguide, the first material having light scattering properties to frustrate a portion of the total internal reflection of the incident light within the optical waveguide; each optical wave guide having formed on the first material a second material.

A distance between each optical waveguide may be equal to a thickness of an optical waveguide divided by a number of optical waveguides.

Each optical waveguide may be parallel thereto.

A display device component comprises a plurality of optical waveguides, each optical waveguide having a front surface and a back surface; each optical wave guide having formed thereon a first material formed on a portion of the back surface of each optical waveguide; each optical wave guide having formed on the first material a second material, the second material having light scattering properties to frustrate a portion of the total internal reflection of the incident light within the optical waveguide.

A distance between each optical waveguide may be equal to a thickness of an optical waveguide divided by a number of optical waveguides.

Each optical waveguide may be parallel thereto.

A display device component comprises a plurality of optical waveguides, each optical waveguide having a front surface and a back surface; each optical wave guide having formed thereon a first material formed on a portion of the front surface of each optical waveguide, the first material having a first surface adjacent to the surface of the optical waveguide and a second surface away from the surface of the optical waveguide, the second surface being non-smooth to frustrate a portion of light being internally reflected within the optical waveguide.

A distance between each optical waveguide may be equal to a thickness of an optical waveguide divided by a number of optical waveguides.

Each optical waveguide may be parallel thereto.

A display device component comprises an optical waveguide having a first surface and a second surface; a first material formed on a portion of the first surface of the optical waveguide; a second material formed on a portion of the first material; and a third material formed on a portion of the second surface of the optical waveguide; the third material having a first surface adjacent to the second surface of the optical waveguide and a second surface away from the second surface of the optical waveguide; the second surface being non-smooth to frustrate a portion of light being internally reflected within the optical waveguide; the second material having light scattering properties.

The first material may be a marking material and the third material may be a marking material.

The second material may be a white marking material.

The white marking material may be ink.

The white marking material may be toner.

The first material may be a non-white colored marking material and the third material may be a non-white colored marking material.

The non-white colored marking material may be ink.

The non-white colored marking material may be toner.

A display device component comprises an optical waveguide having a first surface and a second surface; a first material formed on a portion of the first surface of the optical waveguide; a second material formed on a portion of the first material; and a third material formed on a portion of the second surface of the optical waveguide; the third material having a first surface adjacent to the second surface of the optical waveguide and a second surface away from the second surface of the optical waveguide; the second surface being non-smooth to frustrate a portion of light being internally reflected within the optical waveguide; the second material having light scattering particles embedded therein.

The first material may be a marking material and the third material may be a marking material.

The second material may be a white marking material.

The white marking material may be ink.

The white marking material may be toner.

The first material may be a non-white colored marking material and the third material may be a non-white colored marking material.

The non-white colored marking material may be ink.

The non-white colored marking material may be toner.

A display device component comprises a plurality of optical waveguides, each optical waveguide having a front surface and a back surface; each optical wave guide having formed thereon a first material formed on a portion of the front surface of each optical waveguide, the first material having a first surface adjacent to the surface of the optical waveguide and a second surface away from the surface of the optical waveguide, the second surface being non-smooth to frustrate a portion of light being internally reflected within the optical waveguide; each optical wave guide having formed thereon a second material formed on a portion of the back surface of each optical waveguide; each optical wave guide having formed on the second material a third material, the third material having light scattering properties to frustrate a portion of the total internal reflection of the incident light within the optical waveguide.

The first material may be a marking material and the second material may be a marking material.

The third material may be a white marking material.

The white marking material may be ink.

A display device component comprises an optical waveguide having a front surface and a back surface; a first material formed on a portion of the back surface of the optical waveguide; a second material formed on the first material, the second material having light scattering properties to frustrate a portion of totally internally reflected light within the optical waveguide; and a third material formed on the front surface of the optical waveguide, the third material having a first surface adjacent to the front surface of the optical waveguide and a second surface away from the front surface of the optical waveguide, the second surface being non-smooth to frustrate a portion of light being internally reflected within the optical waveguide.

The first material may be a non-white marking material.

The second material may be a white marking material.

The third material may be a non-white colored marking material.

The third material may be a non-white colored marking material having a color distinct from a color of the first material.

A display device component comprises an optical waveguide having a front surface and a back surface; a first material formed on a portion of the back surface of the optical waveguide, the first material having light scattering properties to frustrate a portion of totally internally reflected light within the optical waveguide; and a second material formed on the front surface of the optical waveguide, the second material having light scattering properties to frustrate a portion of totally internally reflected light within the optical waveguide.

The first material may be a white marking material.

The second material may be a white marking material.

A display device component comprises an optical waveguide having a front surface and a back surface; a first material formed on a portion of the front surface of the optical waveguide material, the first material having light scattering properties to frustrate a portion of totally internally reflected light within the optical waveguide; a second material formed on the first material; and a third material formed on the back surface of the optical waveguide, the third material having light scattering properties to frustrate a portion of totally internally reflected light within the optical waveguide.

The first material may be a white marking material.

The second material may be a non-white marking material.

The third material may be a white colored marking material.

A display device component comprises an optical waveguide having a front surface and a back surface; a first material formed on a portion of the front surface of the optical waveguide material; and a second material formed on the back surface of the optical waveguide, the second material having light scattering properties to frustrate a portion of totally internally reflected light within the optical waveguide.

The first material may be a non-white marking material.

The second material may be a white marking material.

A display device component comprises an optical waveguide having surface; and a first material formed, in an image-wise manner, on the surface of the optical waveguide to create a plurality of image regions having the first material, the first material having light scattering properties; the plurality of image regions including a first subset of the plurality of image regions having a first density of the first material, and a second subset of the plurality of image regions having a second density of the first material; the first density of the first material not being equal to the second density of the first material to create areas of different brightness.

The first material may be a white marking material.

The white marking material may be ink.

The white marking material may be toner.

A display device component comprises an optical waveguide having surface; and a first material formed, in an image-wise manner, on the surface of the optical waveguide to create a plurality of image regions having the first material, the first material light scattering particles embedded therein; the plurality of image regions including, a first subset of the plurality of image regions having a first density of the first material, and a second subset of the plurality of image regions having a second density of the first material; the first density of the first material not being equal to the second density of the first material to create areas of different brightness.

The first material may be a white marking material.

The white marking material may be ink.

The white marking material may be toner.

A display device component comprises an optical waveguide having surface; and a first material formed, in an image-wise manner, on the surface of the optical waveguide to create a plurality of image regions having the first material, the first material light scattering particles embedded therein, each image region having an amount of the first material formed therein; the amount of the first material being modulated for each image region to create areas of different brightness.

The first material may be a white marking material.

The white marking material may be ink.

The white marking material may be toner.

A process for creating and reusing an optical waveguide utilized in an edge lighting illuminated display, comprises (a) forming a first marking material marking on a portion of an optical waveguide having a surface, the first marking material being a UV curable ink and having light scattering properties; (b) forming a second marking material on the first marking material; and (c) cleaning the surface of the optical waveguide, with a solvent, to remove the first marking material and the second marking material.

The solvent may be acetone.

The process may further comprise (d) mechanically scrubbing the surface of the optical waveguide to assist in the removal of the first marking material and the second marking material.

A process for creating and reusing an optical waveguide utilized in an edge lighting illuminated display, comprises (a) forming a first marking material marking on a portion of an optical waveguide having a surface, the first marking material being a UV ink and having light scattering properties; and (b) cleaning the surface of the optical waveguide, with a solvent, to remove the first marking material.

The solvent may be acetone.

The process may further comprise (c) mechanically scrubbing the surface of the optical waveguide to assist in the removal of the first marking material and the second marking material.

A process for creating and reusing an optical waveguide utilized in an edge lighting illuminated display, comprises (a) forming a first marking material on a portion of a surface of the optical waveguide, the first marking material being an UV curable ink and having a first surface adjacent to the surface of the optical waveguide and a second surface away from the surface of the optical waveguide, the second surface being non-smooth to frustrate a portion of totally internally reflected light within the optical waveguide; and (b) cleaning the surface of the optical waveguide, with a solvent, to remove the first marking material.

The solvent may be acetone.

The process may further comprise (c) mechanically scrubbing the surface of the optical waveguide to assist in the removal of the first marking material and the second marking material.

A process for smoothing a rough cut edge of an optical waveguide, comprises (a) flood coating a rough cut edge of an optical waveguide with a curable fluid having an index of refraction substantially equal to an index of refraction of the optical waveguide; and (b) curing the fluid to create a smooth edge.

The curable fluid may be a clear UV curable ink. The curable fluid may be a colored UV curable ink.

A process for smoothing an engraved area of a surface of an optical waveguide, comprises (a) flood coating an engraved area of a surface of optical waveguide with a curable fluid having an index of refraction substantially equal to an index of refraction of the optical waveguide; and (b) curing the fluid to create a smooth surface.

The curable fluid may be a clear UV curable ink.

A display device component comprises an optical waveguide having a surface; a removable transparent layer adhered to the surface of the optical waveguide; a first material formed on a portion of the removable transparent layer; and a second material formed on a portion of the first material; the first material having light scattering particles embedded therein.

The first material may be a UV curable marking material and the second material may be a UV curable marking material.

The removable transparent layer may be a clear removable transparent medium having an index of refraction substantially equal to the optical waveguide to support total internal reflection or a clear removable translucent medium having an index of refraction substantially equal to the optical waveguide to support total internal reflection. The removable transparent layer may be a colored removable transparent medium having an index of refraction substantially equal to the optical waveguide to support total internal reflection or a colored removable translucent medium having an index of refraction substantially equal to the optical waveguide to support total internal reflection.

A process for making a display device component to enable image specific illumination of an image adhered to an optical waveguide, comprises (a) forming a first material on a portion of a removable transparent medium, the first material having light scattering particles embedded therein; (b) forming a second material on the first material; and (c) adhering the removable transparent medium to a surface of an optical waveguide.

The first material may be a UV curable marking material and the second material may be a UV curable marking material.

The removable transparent layer may be a clear removable transparent medium having an index of refraction substantially equal to the optical waveguide to support total internal reflection or a clear removable translucent medium having an index of refraction substantially equal to the optical waveguide to support total internal reflection. The removable transparent layer may be a colored removable transparent medium having an index of refraction substantially equal to the optical waveguide to support total internal reflection or a colored removable translucent medium having an index of refraction substantially equal to the optical waveguide to support total internal reflection.

A display device component comprises an optical waveguide having a surface; a removable transparent layer adhered to the surface of the optical waveguide; a first material formed on a portion of the removable transparent layer; and a second material formed on the first material; the second material having light scattering particles embedded therein.

The first material may be a UV curable marking material and the second material may be a UV curable marking material.

The removable transparent layer may be a clear removable transparent medium having an index of refraction substantially equal to the optical waveguide to support total internal reflection or a clear removable translucent medium having an index of refraction substantially equal to the optical waveguide to support total internal reflection. The removable transparent layer may be a colored removable transparent medium having an index of refraction substantially equal to the optical waveguide to support total internal reflection or a colored removable translucent medium having an index of refraction substantially equal to the optical waveguide to support total internal reflection.

A process for making a display device component to enable image specific illumination of an image adhered to an optical waveguide, comprises (a) forming a first material on a portion of a removable transparent medium; (b) forming a second material on the first material, the second material having light scattering particles embedded therein; and (c) adhering the removable transparent medium to a surface of an optical waveguide.

The first material may be a UV curable marking material and the second material may be a UV curable marking material.

The removable transparent layer may be a clear removable transparent medium having an index of refraction substantially equal to the optical waveguide to support total internal reflection or a clear removable translucent medium having an index of refraction substantially equal to the optical waveguide to support total internal reflection. The removable transparent layer may be a colored removable transparent medium having an index of refraction substantially equal to the optical waveguide to support total internal reflection or a colored removable translucent medium having an index of refraction substantially equal to the optical waveguide to support total internal reflection.

A display device component comprises an optical waveguide having a surface; a removable transparent layer adhered to the surface of the optical waveguide; and a first material formed on a portion of a surface of the removable transparent layer; the first material having a first surface adjacent to the surface of the removable transparent layer and a second surface away from the surface of the removable transparent layer; the second surface being non-smooth to frustrate a portion of light being internally reflected within the optical waveguide.

The first material may be a UV curable marking material and the second material may be a UV curable marking material.

The removable transparent layer may be a clear removable transparent medium having an index of refraction substantially equal to the optical waveguide to support total internal reflection or a clear removable translucent medium having an index of refraction substantially equal to the optical waveguide to support total internal reflection. The removable transparent layer may be a colored removable transparent medium having an index of refraction substantially equal to the optical waveguide to support total internal reflection or a colored removable translucent medium having an index of refraction substantially equal to the optical waveguide to support total internal reflection.

A process for making a display device component to enable image specific illumination of an image adhered to an optical waveguide, comprises (a) forming a first material on a portion of a surface of a removable transparent medium, the first material having a first surface adjacent to the surface of the removable transparent medium and a second surface away from the surface of the removable transparent medium, the second surface being non-smooth to frustrate a portion of light being internally reflected within the optical waveguide; and (b) adhering the removable transparent medium to a surface of an optical waveguide.

The first material may be a UV curable marking material and the second material may be a UV curable marking material.

The removable transparent layer may be a clear removable transparent medium having an index of refraction substantially equal to the optical waveguide to support total internal reflection or a clear removable translucent medium having an index of refraction substantially equal to the optical waveguide to support total internal reflection. The removable transparent layer may be a colored removable transparent medium having an index of refraction substantially equal to the optical waveguide to support total internal reflection or a colored removable translucent medium having an index of refraction substantially equal to the optical waveguide to support total internal reflection.

A display device component comprises an optical waveguide having a surface; a removable transparent layer adhered to the surface of the optical waveguide; and a first material formed, in an image-wise manner, on the surface of the removable transparent layer to create a plurality of image regions having the first material, the first material having light scattering particles embedded therein; the plurality of image regions including, a first subset of the plurality of image regions having a first density of the first material, and a second subset of the plurality of image regions having a second density of the first material; the first density of the first material not being equal to the second density of the first material to create areas of different brightness.

The first material may be a UV curable marking material and the second material may be a UV curable marking material.

The removable transparent layer may be a clear removable transparent medium having an index of refraction substantially equal to the optical waveguide to support total internal reflection or a clear removable translucent medium having an index of refraction substantially equal to the optical waveguide to support total internal reflection. The removable transparent layer may be a colored removable transparent medium having an index of refraction substantially equal to the optical waveguide to support total internal reflection or a colored removable translucent medium having an index of refraction substantially equal to the optical waveguide to support total internal reflection.

A display device component comprises an optical waveguide having a surface; a removable transparent layer adhered to the surface of the optical waveguide; and a first material formed, in an image-wise manner, on the surface of the removable transparent layer to create a plurality of image regions having the first material, the first material light scattering particles embedded therein, each image region having an amount of the first material formed therein; the amount of the first material being modulated for each image region to create areas of different brightness.

The first material may be a UV curable marking material and the second material may be a UV curable marking material.

The removable transparent layer may be a clear removable transparent medium having an index of refraction substantially equal to the optical waveguide to support total internal reflection or a clear removable translucent medium having an index of refraction substantially equal to the optical waveguide to support total internal reflection. The removable transparent layer may be a colored removable transparent medium having an index of refraction substantially equal to the optical waveguide to support total internal reflection or a colored removable translucent medium having an index of refraction substantially equal to the optical waveguide to support total internal reflection.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A display device component comprising:
   an optical waveguide having a smooth front surface and a smooth back surface;
   a non-white material formed on a portion of said smooth back surface of said optical waveguide, said non-white material forming a pattern on said smooth back surface of said optical waveguide, said non-white material having a first surface adjacent to said smooth back surface of said optical waveguide and a second surface away from said smooth back surface of said optical waveguide, said second surface of said non-white material being smooth;
   a first material formed on said second surface of said non-white material, said first material having light scattering properties to frustrate a portion of totally internally reflected light within said optical waveguide such that when said optical waveguide is illuminated by a light source, said pattern formed by said non-white material is visible by viewing said smooth front surface of said optical waveguide and said pattern formed by said non-white material is visible by viewing said smooth back surface of said optical waveguide; and a second material formed on said smooth front surface of said optical waveguide, said second material forming a pattern on said front smooth surface of said optical waveguide, said second material having a first surface adjacent to said smooth front surface of said optical waveguide and a second surface away from said smooth front surface of said optical waveguide, said second surface being non-smooth, said non-smooth second surface frustrating a portion of light being internally reflected within said optical waveguide.

2. The display device component as claimed in claim 1, wherein said non-white material is a non-white marking material.

3. The display device component as claimed in claim 1, wherein said first material is a white marking material.

4. The display device component as claimed in claim 1, wherein said second material is a non-white colored marking material.

5. The display device component as claimed in claim 1, wherein said second material is a non-white colored marking material having a color distinct from a color of said non-white material.

6. A display device component comprising:
an optical waveguide having a smooth front surface and a smooth back surface;
a first material formed on a portion of said smooth back surface of said optical waveguide, said first material having a smooth first surface adjacent to said smooth back surface of said optical waveguide and a smooth second surface away from said smooth back surface of said optical waveguide, said first material having light scattering particles embedded therein, said embedded light scattering particles frustrating a portion of totally internally reflected light within said optical waveguide; and a second material formed on said smooth front surface of said optical waveguide, said second material having a smooth first surface adjacent to said smooth front surface of said optical waveguide and a smooth second surface away from said smooth front surface of said optical waveguide, said second material having light scattering particles embedded therein, said embedded light scattering particles frustrating a portion of totally internally reflected light within said optical waveguide.

7. The display device component as claimed in claim 6, wherein said first material is a white marking material.

8. The display device component as claimed in claim 6, wherein said second material is a white marking material.

9. A display device component comprising:
an optical waveguide having a smooth front surface and a smooth back surface;
a first material formed on a portion of said smooth front surface of said optical waveguide material, said first material having light scattering particles embedded therein;
a non-white material formed on said first material, said non-white material forming a pattern; and
a second material formed on said smooth back surface of said optical waveguide, said second material forming a pattern, said second material having light scattering particles embedded therein, said embedded light scattering particles frustrating a portion of totally internally reflected light within said optical waveguide such that when said optical waveguide is illuminated by a light source, said pattern formed by said second material is visible by viewing said smooth front surface of said optical waveguide and said pattern formed by said second material is visible by viewing said smooth back surface of said optical waveguide;

said light scattering particles embedded in said first material frustrating a portion of totally internally reflected light within said optical waveguide such that when said optical waveguide is illuminated by a light source, said pattern formed by said non-white material is only visible by viewing said smooth front surface of said optical waveguide and said pattern formed by said non-white material is not visible by viewing said smooth back surface of said optical waveguide.

10. The display device component as claimed in claim 9, wherein said first material is a white marking material.

11. The display device component as claimed in claim 9, wherein said second material is a non-white marking material.

12. The display device component as claimed in claim 9, wherein said third material is a white colored marking material.

13. A display device component comprising:
an optical waveguide having a smooth front surface and a smooth back surface;
a non-white material formed on a portion of said smooth front surface of said optical waveguide material, said non-white material forming a pattern; and
a material formed on said smooth back surface of said optical waveguide, said material forming a pattern, said material having light scattering particles embedded therein, said embedded light scattering particles frustrating a portion of totally internally reflected light within said optical waveguide such that when said optical waveguide is illuminated by a light source, said pattern formed by said non-white material is visible by viewing said smooth front surface of said optical waveguide and said pattern formed by said material is visible by viewing said smooth back surface of said optical waveguide and by viewing said smooth front surface of said optical waveguide.

14. The display device component as claimed in claim 13, wherein said first material is a non-white marking material.

15. The display device component as claimed in claim 13, wherein said second material is a white marking material.

16. A display device component comprising:
a first optical waveguide having a smooth first surface and a smooth second surface;
a second optical waveguide having a smooth third surface and a smooth fourth surface;
a first material formed on a portion of said smooth first surface of said first optical waveguide;
a second material formed on said first material, said second material forming a pattern;
a third material formed on a portion of said smooth second surface of said first optical waveguide, said third material forming a pattern;
a fourth material formed on said third material;
said first material having light scattering particles embedded therein, said embedded light scattering particles frustrating a portion of totally internally reflected light within said first optical waveguide such that when said first optical waveguide is illuminated by a light source, said pattern formed by said second material is only visible by viewing said smooth first surface of said first optical waveguide and said pattern formed by said second material is not visible by viewing said smooth second surface of said first optical waveguide;

said fourth material having light scattering particles embedded therein, said embedded light scattering particles frustrating a portion of totally internally reflected light within said first optical waveguide such that when said first optical waveguide is illuminated by a light source, said pattern formed by said third material is visible by viewing said smooth first surface of said first optical waveguide;

a fifth material formed on a portion of said smooth third surface of said second optical waveguide;

a sixth material formed on said fifth material, said sixth material forming a pattern;

a seventh material formed on a portion of said smooth fourth surface of said second optical waveguide, said seventh material forming a pattern;

an eighth material formed on said seventh material;

said fifth material having light scattering particles embedded therein, said embedded light scattering particles frustrating a portion of totally internally reflected light within said second optical waveguide such that when said second optical waveguide is illuminated by a light source, said pattern formed by said sixth material is only visible by viewing said smooth first surface of said first optical waveguide and said pattern formed by said sixth material is not visible by viewing said smooth second surface of said second optical waveguide;

said eighth material having light scattering particles embedded therein, said embedded light scattering particles frustrating a portion of totally internally reflected light within said second optical waveguide such that when said second optical waveguide is illuminated by a light source, said pattern formed by said seventh material is visible by viewing said smooth first surface of said optical waveguide.

17. The display device component as claimed in claim 16, wherein said first optical waveguide is spaced apart from said second optical waveguide.

18. The display device component as claimed in claim 17, wherein a distance between said first optical waveguide and said second optical waveguide is equal to half a thickness of said first optical waveguide.

19. The display device component as claimed in claim 17, wherein said first optical waveguide is parallel to said second optical waveguide.

20. A display device component comprising:
a plurality of optical waveguides, each optical waveguide having a smooth front surface and a smooth back surface;
each optical waveguide guide having formed thereon a first material formed on a portion of said smooth front surface of each optical waveguide, said first material having light scattering particles embedded therein;
each optical waveguide guide having, formed on said first material, a second material, said second material forming a pattern;
each optical waveguide guide having formed thereon a third material formed on a portion of said smooth back surface of each optical waveguide, said third material forming a pattern;
each optical waveguide guide having, formed on said third material, a fourth material, said fourth material having light scattering particles embedded therein;

said light scattering particles embedded in said first material frustrating a portion of totally internally reflected light within each optical waveguide such that when each optical waveguide is illuminated by a light source, said pattern formed by said first material is only visible by viewing said smooth front surface of each optical waveguide and said pattern formed by said first material is not visible by viewing said smooth back surface of each optical waveguide;

said light scattering particles embedded in said fourth material frustrating a portion of totally internally reflected light within each optical waveguide such that when each optical waveguide is illuminated by a light source, said pattern formed by said fourth material is only visible by viewing said smooth front surface of each optical waveguide and said pattern formed by said fourth material is not visible by viewing said smooth back surface of each optical waveguide.

21. The display device component as claimed in claim 20, wherein a distance between each optical waveguide is equal to a thickness of an optical waveguide divided by a number of optical waveguides.

22. The display device component as claimed in claim 20, wherein each optical waveguide is parallel thereto.

23. A display device component comprising:
a plurality of optical waveguides, each optical waveguide having a smooth front surface and a smooth back surface;
each optical waveguide guide having formed thereon a first material formed on a portion of said smooth front surface of each optical waveguide, said first material forming a pattern, said first material having a first surface adjacent to the smooth front surface of the optical waveguide and a second surface away from the smooth front surface of the optical waveguide, the second surface being non-smooth, said non-smooth second surface frustrating a portion of light being internally reflected within said optical waveguide such that when each optical waveguide is illuminated by a light source, said pattern formed by said first material is visible by viewing said smooth front surface of each optical waveguide;
each optical waveguide guide having formed thereon a second material formed on a portion of said smooth back surface of each optical waveguide, said second material forming a pattern;
each optical waveguide guide having, formed on said second material, a third material, said third material having light scattering particles embedded therein, said embedded light scattering particles frustrating a portion of totally internally reflected light within said optical waveguide such that when each optical waveguide is illuminated by a light source, said pattern formed by said second material is visible by viewing said smooth front surface of each optical waveguide.

24. The display device as claimed in claim 23, wherein a distance between each optical waveguide is equal to a thickness of an optical waveguide divided by a number of optical waveguides.

25. The display device as claimed in claim 23, wherein each optical waveguide is parallel thereto.

* * * * *